United States Patent
Becker et al.

(10) Patent No.: US 8,586,599 B2
(45) Date of Patent: *Nov. 19, 2013

(54) POLYMORPHIC FORMS OF 6-(1-METHYL-1H-PYRAZOL-4-YL)-2-{3-[5-(2-MORPHOLIN-4-YL-ETHOXY)-PYRIMIDIN-2-YL]-BENZYL}-2H-PYRIDAZIN-3-ONE DIHYDROGENPHOSPHATE AND PROCESSES OF MANUFACTURING THEREOF

(75) Inventors: Axel Becker, Darmstadt (DE); Clemens Kuehn, Darmstadt (DE); Christoph Saal, Otzberg (DE); Oliver Schadt, Rodenbach (DE); Dieter Dorsch, Ober-Ramstadt (DE); Eva Kriegbaum, Darmstadt (DE); Frank Stieber, Heidelberg (DE); Cristina Donini, Geneva (CH)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/141,142

(22) PCT Filed: Nov. 24, 2009

(86) PCT No.: PCT/EP2009/008358
§ 371 (c)(1),
(2), (4) Date: Jun. 21, 2011

(87) PCT Pub. No.: WO2010/072295
PCT Pub. Date: Jul. 1, 2010

(65) Prior Publication Data
US 2011/0257180 A1    Oct. 20, 2011

(30) Foreign Application Priority Data
Dec. 22, 2008   (EP) .................................... 08022253

(51) Int. Cl.
A61K 31/501     (2006.01)
A61K 31/5377    (2006.01)
C07D 413/14     (2006.01)
C07D 403/14     (2006.01)

(52) U.S. Cl.
USPC .......................................... 514/269; 544/295

(58) Field of Classification Search
USPC .......................................... 544/295; 514/269
See application file for complete search history.

(56) References Cited

U.S. PATENT DOCUMENTS

| 6,242,461 | B1 | 6/2001 | Goldstein |
| 6,403,586 | B1 | 6/2002 | Ohkuchi et al. |
| 8,071,593 | B2 | 12/2011 | Schadt et al. |
| 8,173,653 | B2 | 5/2012 | Dorsch et al. |
| 8,329,692 | B2 | 12/2012 | Schadt et al. |
| 2004/0152739 | A1 | 8/2004 | Hanau |
| 2004/0259863 | A1 | 12/2004 | Eggenweiler et al. |
| 2005/0107319 | A1 | 5/2005 | Bansal |
| 2007/0015771 | A1 | 1/2007 | Matteucci et al. |
| 2007/0043057 | A1 | 2/2007 | Matteucci et al. |
| 2007/0203136 | A1 | 8/2007 | Lu et al. |
| 2007/0265272 | A1 | 11/2007 | Cheng et al. |
| 2008/0293719 | A1 | 11/2008 | Dorsch et al. |
| 2009/0098181 | A1 | 4/2009 | Lu et al. |
| 2009/0124612 | A1 | 5/2009 | Albrecht et al. |
| 2010/0197690 | A1 | 8/2010 | Schadt et al. |
| 2010/0234354 | A1 | 9/2010 | Dorsch et al. |
| 2010/0273796 | A1 | 10/2010 | Dorsch et al. |
| 2010/0280030 | A1 | 11/2010 | Schadt et al. |
| 2010/0286390 | A1 | 11/2010 | Shigeta et al. |
| 2011/0034474 | A1 | 2/2011 | Dorsch et al. |
| 2011/0092498 | A1 | 4/2011 | Dorsch et al. |
| 2011/0098269 | A1 | 4/2011 | Becknell et al. |
| 2011/0112061 | A1 | 5/2011 | Hu et al. |
| 2011/0263596 | A1 | 10/2011 | Schadt et al. |
| 2011/0269957 | A1 | 11/2011 | Fandrick et al. |
| 2012/0028988 | A1 | 2/2012 | Sakamoto et al. |
| 2012/0040949 | A1 | 2/2012 | Berthel et al. |

FOREIGN PATENT DOCUMENTS

| DE | 196 04 388 | 8/1997 |
| DE | 10 2005 057 924 | 6/2007 |
| EP | 1 061 077 | 12/2000 |
| JP | 10 259176 | 9/1998 |
| JP | 2001 192384 | 7/2001 |
| WO | WO 2009/007074 A1 | 1/2000 |
| WO | WO-03 037349 | 5/2003 |
| WO | WO-2004 058762 | 7/2004 |
| WO | WO-2005 004607 | 1/2005 |
| WO | WO-2006 015263 | 2/2006 |
| WO | WO-2007 044796 | 4/2007 |

(Continued)

OTHER PUBLICATIONS

Gould, abstract of "Salt selection for basic drugs," International J. of Pharmaceutics, vol. 33, p. 201 (1986).*
Berge, "Pharmaceutical Salts," J. Pharm. Sci., 66(1):1-19 (1977).*
Co-pending U.S. Appl. No. 12/668,491, commonly assigned.*
International Search Report of PCT/EP2009/008358 (Feb. 5, 2010).
"Cancer" MedLine Plus (2009). Accessed Mar. 17, 2009. http://www.nlm.nih.gov/medlineplus/cancer.html.
Berthou, S. et al., "The Met kinase inhibitor SU11274 exhibits a selective inhibition pattern toward different receptor mutated variants," Oncogene, 2004, vol. 23, pp. 5387-5393.

(Continued)

Primary Examiner — Kamal Saeed
Assistant Examiner — Janet L Coppins
(74) Attorney, Agent, or Firm — Millen, White, Zelano & Branigan, P.C.

(57) ABSTRACT

The present invention relates to 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate, its solvates and crystalline modifications thereof. The present invention further relates to processes of manufacturing these crystalline modifications as well as their use in the treatment and/or prophylaxis of physiological and/or pathophysiological conditions, which are caused, mediated and/or propagated by the inhibition, regulation and/or modulation of signal transduction of kinases, in particular by the inhibition of tyrosine kinases, e.g. pathophysiological conditions such as cancer.

40 Claims, 24 Drawing Sheets

(56) References Cited

FOREIGN PATENT DOCUMENTS

| | | | |
|---|---|---|---|
| WO | WO-2007 064797 | | 6/2007 |
| WO | WO-2007/065518 | * | 6/2007 |
| WO | WO 2007/065518 A1 | | 6/2007 |
| WO | WO-2007 075567 | | 7/2007 |
| WO | WO-2007 130383 | | 11/2007 |
| WO | WO-2007 132308 | | 11/2007 |
| WO | WO-2008 008539 | | 1/2008 |
| WO | WO-2008 075068 | | 6/2008 |
| WO | WO-2009 006959 | | 1/2009 |
| WO | WO-2009 050197 | | 4/2009 |
| WO | WO-2009 053737 | | 4/2009 |
| WO | WO-2009 063061 | | 5/2009 |
| WO | WO-2009 080314 | | 7/2009 |
| WO | WO-2009 080364 | | 7/2009 |
| WO | WO-2009 080533 | | 7/2009 |
| WO | WO-2009 080534 | | 7/2009 |
| WO | WO-2009 080555 | | 7/2009 |
| WO | WO-2009 080721 | | 7/2009 |
| WO | WO-2009 080725 | | 7/2009 |
| WO | WO-2009 081197 | | 7/2009 |
| WO | WO-2009 083076 | | 7/2009 |
| WO | WO-2009 083105 | | 7/2009 |
| WO | WO-2009 085659 | | 7/2009 |
| WO | WO-2009 086041 | | 7/2009 |
| WO | WO-2009 086264 | | 7/2009 |

OTHER PUBLICATIONS

Buchanan, Sean G. "SGX523 is an exquisitely selectively, ATP-competitive inhibitor of the MET receptor tyrosine kinase with antitumor activity in vivo" Molecular Cancer Therapeutics, Dec. 2009;8(12): 3181-3190.
Cancer Drug Design and Discovery, Neidle, Stephen, ed. (Elsevier/Academic Press), pp. 427-431, 2008.
Chen et al., Circulation, 2008, vol. 118, pp. 84-95.
Database Beilstein, Beilstein Institute for Organic Chemistry, Frankfurt, DE, XP002506064, 1991.
Database CA (Online) Chemical Abstracts Service, Columbus, Ohio US:2002, Dushamov, D.A.et al., Acylation of 6-halobenzoxazolin-2-ones by acid chlorides in the presence of a small quantity of iron(III) chloride hexahydrate, XP002496356.
Database CA (Online) Chemical Abstracts Service, Columbus, Ohio US:1979, Domagalina, Eugenia et al, "Acylation of benzoxazolin—2-ones and 3-hydroxyl-1, 2 benzisoxazoles," XP002496357 Polish Journal of Pharmacology and Pharmacy.
Database CA (Online) Chemical Abstracts Service, Columbus, Ohio US; 1967, Nitta, yoshihiro et al: "Benzoxazolone derivatives," XP002496358.
Databse Beilstein, Beilstein Institute for Organic Chemistry, Frankfurt, DE, XP002506065, 2008.
Ettmayer et al. "Lessons Learned from Marketed and Investigational Prodrugs" J. Med. Chem., (2004), 47(10):2393-2404.
Flouzat, Christine et al. "Synthesis and N-substitution of an uncommon heterocyclic system: oxazolo[5,4-b]pyridin-2(1H)-one," Tetrahedron Letters, Bd. 33, Nr. 32, 1992 Seiten 4571-4574, XP00249354.
Fujisawa Pharmaceut Co Ltd., "Pyrazolopyridine compound and pharmaceutical use thereof," Patent Abstracts of Japan, Publication Date: Jul. 17, 2001; English Abstract of JP-2001 192384.
Glen, H. et al., "E7080, a multi-targeted tyrosin kinase inhibitor suppresses tumor cell migration and invasion," BMC Cancer, 2011, vol. 11, No. 309.
Golub et al. "Molecular Classification of Cancer: Class Discovery and Class Prediction by Gene Expression Monitoring" Science (1999), 286:521-537.
Guessous, Fadila et al. "An orally Bioavailable c-Met Kinase Inhibitor Potently Inhibits Brain Tumor Malignancy and Growth", Anti-Cancer in Medicinal Chemistry, 2010, 10(1):28-35.
H. Refaat et al., "Synthesis and Anti-Inflammatory Activity of Certain Piperazinylthienylpyridazine Derivatives," Arch Pharm Res., vol. 30, No. 7 (2007) pp. 803-811.
Hackh's Chem Dict., 3$^{rd}$. Ed 1944, p. 18.

Hawley's Condensed Chem Dict., 14$^{th}$ Ed., 2002.
Hill, K. S. et al., "Met Receptor Tyrosine Kinase Signaling Induces Secretion of the Angiogenic Chemokine Interleukin-8/CXCL8 in Pancreatic Cancer," PLoS ONE, Jul. 1, 2012, vol. 7, No. 7, e40420.
http://www.iupac.org/goldbook/A00123.pdf, downloaded Oct. 29, 2010.
http://www.uspto.gov/wb/offices/pac/dapp/1pecba.htm#7 last accessed on Nov. 22, 2011.
International Search Report "International Application No. PCT/EP2008/003696," Date of Completion Sep. 18, 2008, Date of Mailing Oct. 1, 2008, 4 pages.
International Search Report for PCT/EP2008/003473 dated Jul. 28, 2008.
International Search Report for PCT/EP2008/005928 dated Dec. 11, 2008.
International Search Report of PCT/EP2008/009970 dated Jan. 28, 2009.
International Search Report of PCT/EP2009/002137 (Jun. 4, 2009).
International Search Report of PCT/EP2009/003675 (Aug. 26, 2009).
International Search Report of PCT/EP2009/005172 dated Jan. 26, 2010.
Japan Tobacco Inc., "New Amide derivative having vascularization inhibiting action and its use," Patent Abstracts of Japan, Publication Date: Sep. 29, 1998; English Abstracts of JP-10 259176.
Jin et al., Mol. Cancer Ther., Jul. 2006, vol. 5, pp. 1754-1763.
Jin, Hongkui et al. "MetMAb, the One-Armed 5D5 Anti-c-Met Antibody, Inhibits Orthotopic Pancreatic Tumor Growth and Improves Survival", Cancer Res 2008;68(11):4360-4368; Jun. 1, 2008. www.aacrjournals.org.
Johnson et al. "Relationships between drug activity in NCI preclinical in vitro and in vivo models and early clinical trials." British Journal of Cancer (2001) 84(10):1424-1431.
Knowles, Lynn M. et al. "HGF and c-Met Participate in Paracrine Tumorigenic Pathways in Head and Neck Squamous Cell Cancer", Clin Cancer Res, Jun. 1, 2009; 15(11):3740-3750. www.aacrjournals.org.
Lala et al. "Role of nitric oxide in tumor progression: Lessons from experimental tumors." Cancer and Metastasis Review (1998), 17(1), 91-106.
Lima, L. M. et al., "Bioisosterism: a useful strategy for molecular modification and drug design," Current Medicinal Chemistry, 2005, vol. 12, No. 1, pp. 23-49.
Liu, Xiangdong et al. "A novel kinase inhibitor INCB28060 blocks c-MET-dependent signaling, neoplastic activities, and crosstalk with EGFR and HER-3", Clin Cancer Res (45 pages); Published: Sep. 14, 2011.
Locatelli et al., J. Biol. Chem., Jun. 17, 2011, vol. 286, No. 24, pp. 21062-21072.
M. Goekce et al., "Synthesis of New Mannich Bases of Arylpyridazinones as Analgesic and Anti-Inflammatory Agents," Drug Research, vol. 55, No. 6 (2005) pp. 318-325.
Merck Patent GMBH, "New Aryl-alkyl diazinone derivatives," Espacenet, Publication Date: Aug. 14, 1997; English Abstract of DE-196 04 388.
Morissette et al. "High-throughput crystallization: polymorphs, salts, co-crystals and solvates of pharmaceutical solids." Advanced Drug Deliver Reviews 2004, 56 275-300.
Office Action for Related Columbian Patent Application No. 09-138245 dated Sep. 21, 2012.
Qian, Fawn et al. "Inhibition of Tumor Cell Growth, Invasion, and Metastasis by EXEL-2880 (XL880, GSK1363089), a Novel Inhibitor of HGF and VEGF Receptor Tyrosine Kinases", Cancer Res 2009;69(20):8009-8016. Dated: Oct. 15, 2009. www.aacrjournals.org.
Samlowski et al., BJU INT., 2008, vol. 102, No. 2, pp. 162-165, Abstract.
Sampson, Erik R. et al. "The Orally Bioavailable Met Inhibitor PF-2341066 Inhibits Osteosarcoma Growth and Osteolysis/Matrix Production in a Xenograft Model", Journal of Bone and Mineral Research, 26(6):1283-1294; Dated: Jun. 2011.
Sausville et al. "Contributions of Human Tumor Xenografts to Anti-cancer Drug Development" Cancer Res. 2006, 66(7), Apr. 1, 2006.

(56) References Cited

OTHER PUBLICATIONS

Search Report for Chilean Patent Application No. 3854-08 filed Dec. 19, 2008.
Singapore Written Opinion for Application No. 201007486-2 (Sep. 26, 2011).
Smolen et al., Proc. Natl Acad Sci USA, Feb. 2006, vol. 103, No. 7, pp. 2316-2321.
Souillac et al. Characterization of Delivery Systems, Differential Scanning Calorimetry, pp. 217-218 (in Encyclopedia of Controlled Drug Delivery, 1999, John Wiley & Sons, pp. 212-227).
Stella, V. "Prodrugs as therapeutics" Expert Opin. Ther. Patents (2004), 14(3):277-280.
Testa, B. "Prodrug research: futile or fertile?" Biochemical Pharmacology, 68 (2004): 2097-2106.
Tuynman et al., Br. J. Cancer, 2008, vol. 98, No. 6, pp. 1102-1108, Abstract.
Ucar, Huseyin et al., "Fries Like" Rearragement: a novel and efficient metod for the sythesis of 6-acyl-2(3H)-benzoxazolones and 6-acyl-2(3H)-benzothiazolones Tetrahedron, Bd. 54, Nr. 9, 1998, Seiten 1763-1772 XP002496355.
Underiner et al., Anti-Cancer Agents in Medicinal Chemistry, 2010, vol. 10, pp. 7-27.
Vippagunta, S.R. "Crystalline Solids" Advanced Drug Delivery Reviews 48(2001):3-26.
Wang et al., Clin Cancer Res., Mar. 15, 2012, vol. 18, No. 6 , pp. 1663-1671.
Wolff et al. Burger's Medicinal Chemistry and Drug Discovery. $5^{th}$ Ed. vol. 1 Principles and Practice, 1995, pp. 975-977.
Ziegler, D. S. et al., "Resistance of human glioblastoma multiforme cells to growth factor inhibitors is overcome by blockade of inhibitors of apoptosis proteins," Journal of Clinical Investigation, Sep. 9, 2008, vol. 118, pp. 3109-3122.
Zillhardt, Marion et al. "Foretinib (GSK1363089), an Orally Available Multikinase Inhibitor of c-Met and VEGFR-2, Blocks Proliferation, Induces Anoikis, and Impairs Ovarian Cancer Metastasis", Clin Cancer Res 2011;17:4042-4051. Published: May 6, 2011. www.aacrjournals.org.
Zou, Helen Y. et al. "An Orally Available Small-Molecule Inhibitor of c-Met, PF-2341066, Exhibits Cytoreductive Antitumor Efficacy through Antiproliferative and Antiangiogenic Mechanisms", Cancer Res 2007; 67:(9)4408-4417. Dated: May 1, 2007. www.aacrjournals.org.
Zou, Helen Y. et al. "Sensitivity of Selected Human tumor Models to PF-04217903, a Novel Selective c-Met Kinase Inhibitor", Molecular Cancer Therapeutics, American Association for Cancer Research. 32 pages. Published: Mar. 2, 2012.

\* cited by examiner

POLYMORPHIC FORMS OF 6-(1-METHYL-1H-PYRAZOL-4-YL)-2-{3-[5-(2-MORPHOLIN-4-YL-ETHOXY)-PYRIMIDIN-2-YL]-BENZYL}-2H-PYRIDAZIN-3-ONE DIHYDROGENPHOSPHATE AND PROCESSES OF MANUFACTURING THEREOF

TECHNICAL FIELD

The present invention relates to 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate, its solvates and crystalline modifications thereof as well as their medical uses and processes of manufacturing.

PRIOR ART 6-(1-methyl-1H-pyrazol-4-yl)-2-{3-[5-(2-morpholin-4-yl-ethoxy)-pyrimidin-2-yl]-benzyl}-2H-pyridazin-3-one (I)

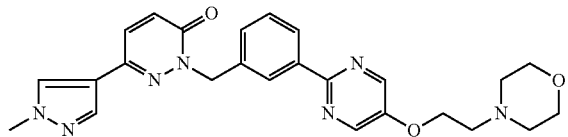

was first described in international patent applications PCT/EP2008/003473, filed on 29 Apr. 2008, and PCT/EP2008/005508, filed on 4 Jul. 2008.

In PCT/EP2008/003473 6-(1-methyl-1H-pyrazol-4-yl)-2-{3-[5-(2-morpholin-4-yl-ethoxy)-pyrimidin-2-yl]-benzyl}-2H-pyridazin-3-one is referred to as compound "A229". Example 38 of PCT/EP2008/003473 describes a first way of synthesizing 6-(1-methyl-1H-pyrazol-4-yl)-2-{3-[5-(2-morpholin-4-yl-ethoxy)-pyrimidin-2-yl]-benzyl}-2H-pyridazin-3-one. p-Toluenesulfonate and phosphate are mentioned as possible salt forms. Besides, example 39 of PCT/EP2008/003473 describes an alternative way of synthesizing 6-(1-methyl-1H-pyrazol-4-yl)-2-{3-[5-(2-morpholin-4-yl-ethoxy)-pyrimidin-2-yl]-benzyl}-2H-pyridazin-3-one. Example 1 of PCT/EP2008/005508 describes the same first way of synthesizing 6-(1-methyl-1H-pyrazol-4-yl)-2-{3-[5-(2-morpholin-4-yl-ethoxy)-pyrimidin-2-yl]-benzyl}-2H-pyridazin-3-one and also mentions p-toluenesulfonate and phosphate as possible salt forms. Example 2 of PCT/EP2008/005508 refers to sulfate, mesylate, besylate, tosylate, fumarate and maleate as additional salt forms.

Both prior art documents are silent about 6-(1-methyl-1H-pyrazol-4-yl)-2-{3-[5-(2-morpholin-4-yl-ethoxy)-pyrimidin-2-yl]-benzyl}-2H-pyridazin-3-one as a dihydrogenphosphate salt and further do not mention polymorphic forms, crystal modifications or the like of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate.

Certain crystalline, i.e. morphological or polymorphic forms of pharmaceutical compounds may be of interest to those involved in the development of suitable pharmaceutical dosage forms. This is because if a certain polymorphic form is not held constant during clinical and stability studies, the exact dosage used or measured may not be comparable from one batch to the other. Once a pharmaceutical compound is produced for use, it is important to verify the morphological or polymorphic form delivered in each dosage form to assure that the production process delivers the same form and that the same amount of drug is included in each dosage. Therefore, it is imperative to assure that either a single morphological or polymorphic form or a known combination of morphological or polymorphic forms is present. In addition, certain morphological or polymorphic forms may exhibit enhanced thermodynamic stability and may be more suitable than other morphological or polymorphic forms for inclusion in pharmaceutical formulations.

The citation of any reference in this application is not an admission that the reference is relevant prior art to this application.

DESCRIPTION OF THE INVENTION

The present invention has the object to provide novel salt forms of 6-(1-methyl-1H-pyrazol-4-yl)-2-{3-[5-(2-morpholin-4-yl-ethoxy)-pyrimidin-2-yl]-benzyl}-2H-pyridazin-3-one as well as novel polymorphic forms thereof.

The object of the present invention has surprisingly been solved in one aspect by providing 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate.

The object of the present invention has surprisingly been solved in another aspect by providing 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate solvate, preferably 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate.

It has been found that 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate is able to form solvates in crystalline modifications. Examples of such solvates include solvates from water, solvates from alcohols such as methanol, ethanol, propan-1-ol or propan-2-ol; solvates from organic esters such as ethyl acetate; solvates from nitriles such as acetonitrile; solvates from ketones such as acetone and butanone; solvates from ethers such as tetrahydrofuran (THF) and solvates from chlorinated hydrocarbons such as chloroform and solvates of hydrocarbons such as n-heptane or toluene. Preferred solvates are formed with polar solvents, preferably water, alcohols, organic esters, nitriles, ketones and ethers.

Preferably, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate forms anhydrates and solvates with water, acetone, tetrahydrofuran, methanol, ethyl acetate or n-heptane in crystalline modifications that means the bound solvent together with 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate build the crystal structure. The molar ratio of the solvent to 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate could vary as known to skilled persons in the art. Preferably, the molar ratio is between 0.25:1 to 2.5:1, more preferably between 0.5:1 to 1:1, most preferably 1:1 (n-heptane solvate ⅕:1). It should be understood that the present anhydrates and solvates of the invention may contain unbound water that is to say water which is other than water of crystallization.

Hence, in a preferred embodiment, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate solvate, preferably -(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate, is provided in its crystalline modifications.

The object of the present invention has surprisingly been solved in another aspect by providing 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate.

In a preferred embodiment, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate is provided in its crystalline modification A1, which is characterized by XRD peaks comprising 3.2°, 6.5°, 9.8°, and 13.1° 2θ (all 0.1° 2θ, using Cu-Kα₁ radiation).

In a preferred embodiment, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate is provided in its crystalline modification A1, which is characterized by XRD peaks comprising 18.4°, 18.8°, 23.7°, 24.2°, 26.4°, and 28.2° 2θ (all ±0.1° 2θ, using Cu-Kα₁ radiation).

In a preferred embodiment, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate is provided in its crystalline modification A1, which is characterized by XRD peaks comprising 14.4°, 15.8°, 17.5°, 19.5°, and 21.9° 2θ (all ±0.1° 2θ, using Cu-Kα₁ radiation).

In a preferred embodiment, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate is provided in its crystalline modification A1, which is characterized by the following XRD data:

Form A1:

| Peak No. | d/Å | °2θ (Cu—Kα₁ radiation) ± 0.1° | Indexing (h, k, l) |
|---|---|---|---|
| 1 | 27.45 | 3.2 | (2, 0, 0) |
| 2 | 13.62 | 6.5 | (4, 0, 0) |
| 3 | 9.02 | 9.8 | (6, 0, 0) |
| 4 | 6.75 | 13.1 | (8, 0, 0) |
| 5 | 6.15 | 14.4 | (−2, 0, 2) |
| 6 | 5.59 | 15.8 | (−6, 0, 2) |
| 7 | 5.07 | 17.5 | (−8, 0, 2) |
| 8 | 4.81 | 18.4 | (9, 1, 0) |
| 9 | 4.72 | 18.8 | (−9, 1, 1) |
| 10 | 4.55 | 19.5 | (6, 0, 2) |
| 11 | 4.06 | 21.9 | (8, 0, 2) |
| 12 | 3.75 | 23.7 | (11, 1, 1) |
| 13 | 3.68 | 24.2 | (2, 2, 1) |
| 14 | 3.37 | 26.4 | (3, 1 3) |
| 15 | 3.16 | 28.2 | (−15, 1, 2) |

The object of the present invention has surprisingly been solved in another aspect by providing 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate.

In a preferred embodiment, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate is provided in its crystalline modification H1, which is characterized by XRD peaks comprising 3.1°, 9.4°, and 18.8° 2θ (all ±0.1° 2θ, using Cu-Kα₁ radiation).

In a preferred embodiment, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate is provided in its crystalline modification H1, which is characterized by XRD peaks comprising 19.1°, 22.8°, and 26.4°2θ (all ±0.1° 2θ, using Cu-Kα₁ radiation).

In a preferred embodiment, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate is provided in its crystalline modification H1, which is characterized by XRD peaks comprising 14.4°, 15.0°, and 17.8° 2θ (all ±0.1° 2θ, using Cu-Kα₁ radiation).

In a preferred embodiment, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate is provided in its crystalline modification H1, which is characterized by XRD peaks comprising 14.7°, 18.6°, 23.2°, 23.8°, 26.8°, and 27.6° 2θ (all ±0.1° 2θ, using Cu-Kα₁ radiation).

In a preferred embodiment, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate is provided in its crystalline modification H1, which is characterized by the following XRD data:

Form H1:

| Peak No. | d/Å | °2θ (Cu—Kα₁ radiation) ± 0.1° | Indexing (h, k, l) |
|---|---|---|---|
| 1 | 28.42 | 3.1 | (1, 0, 0) |
| 2 | 9.40 | 9.4 | (3, 0, 0) |
| 3 | 6.13 | 14.4 | (0, 0, 2) |
| 4 | 6.01 | 14.7 | (2, 1, 1) |
| 5 | 5.89 | 15.0 | (1, 0, 2) |
| 6 | 4.97 | 17.8 | (3, 0, 2) |
| 7 | 4.77 | 18.6 | (4, 1, 1) |
| 8 | 4.71 | 18.8 | (6, 0, 0) |
| 9 | 4.64 | 19.1 | (5, 1, 0) |
| 10 | 3.89 | 22.8 | (2, 2, 0) |
| 11 | 3.83 | 23.2 | (−1, 2, 1) |
| 12 | 3.73 | 23.8 | (−2, 2, 1) |
| 13 | 3.38 | 26.4 | (0, 2, 2) |
| 14 | 3.33 | 26.8 | (−4, 1, 3) |
| 15 | 3.22 | 27.6 | (−3, 2, 2) |

The object of the present invention has surprisingly been solved in another aspect by providing 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate in its crystalline modification NF3 (crystalline modification NF3 can be a hydrate or an anhydrate), which is characterized by XRD peaks comprising 15.3°, 16.7°, 21.6°, and 23.1° 2θ (all ±0.1° 2θ, using Cu-Kα₁ radiation).

In a preferred embodiment, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate is provided in its crystalline modification NF3, which is characterized by the following XRD data:

Form NF3:

| Peak No. | d/Å | °2θ (Cu—Kα₁ radiation) ± 0.1° |
|---|---|---|
| 1 | 27.30 | 3.2 |
| 2 | 13.62 | 6.5 |
| 3 | 9.02 | 9.8 |
| 4 | 6.71 | 13.2 |
| 5 | 6.11 | 14.5 |
| 6 | 5.79 | 15.3 |
| 7 | 5.57 | 15.9 |
| 9 | 5.32 | 16.7 |
| 9 | 5.05 | 17.5 |
| 10 | 4.81 | 18.4 |
| 11 | 4.58 | 19.4 |

-continued

| Peak No. | d/Å | °2θ (Cu—Kα$_1$ radiation) ± 0.1° |
|---|---|---|
| 12 | 4.12 | 21.6 |
| 13 | 4.04 | 22.0 |
| 14 | 3.84 | 23.1 |
| 15 | 3.75 | 23.7 |
| 16 | 3.69 | 24.1 |
| 17 | 3.37 | 26.4 |
| 18 | 3.16 | 28.3 |

The object of the present invention has surprisingly been solved in another aspect by providing 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate in its crystalline modification NF5, which is characterized by XRD peaks comprising 13.9°, 15.7°, 16.6°, 17.3°, 19.8°, and 22.1° 2θ (all ±0.1° 2θ, using Cu-Kα$_1$ radiation).

In a preferred embodiment, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate is provided in its crystalline modification NF5, which is characterized by the following XRD data:

| Peak No. | d/Å | °2θ (Cu—Kα$_1$ radiation) ± 0.1° |
|---|---|---|
| 1 | 28.54 | 3.1 |
| 2 | 9.41 | 9.4 |
| 3 | 6.37 | 13.9 |
| 4 | 6.10 | 14.5 |
| 5 | 5.98 | 14.8 |
| 6 | 5.82 | 15.2 |
| 7 | 5.62 | 15.7 |
| 9 | 5.32 | 16.6 |
| 9 | 5.13 | 17.3 |
| 10 | 4.96 | 17.9 |
| 11 | 4.80 | 18.5 |
| 12 | 4.69 | 18.9 |
| 13 | 4.63 | 19.2 |
| 14 | 4.48 | 19.8 |
| 15 | 4.02 | 22.1 |
| 16 | 3.90 | 22.8 |
| 17 | 3.85 | 23.1 |
| 18 | 3.73 | 23.9 |
| 19 | 3.38 | 26.3 |
| 20 | 3.32 | 26.8 |
| 21 | 3.23 | 27.6 |

In the course of the present invention, the term "crystalline modification" is used as a synonym for terms "crystalline form", "polymorphic form", "polymorphic modification", "morphological form" and the like.

The crystalline modifications of the present invention, in particular crystalline modification A1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate, crystalline modification H1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate, crystalline modification NF3 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate (crystalline modification NF3 can be a hydrate or an anhydrate) and crystalline modification NF5 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate are surprisingly characterized by, among others, a reduced hygroscopicity, a better compressibility during the tableting process, a prolonged shelf life, a better thermodynamic stability, i.e. stability against heat and humidity, a better resistance to sunlight, i.e. UV-light, an increased bulk density, an improved solubility, bioavailability characteristics which are constant from one batch to the other, better flow and handling properties in the tableting process, an improved colour stability and better filtration properties in the production process. Therefore, by use of the crystalline modifications of the present invention, it is possible to obtain pharmaceutical formulations with improved homogeneity, stability, purity and uniformity from one batch to the other.

Furthermore, crystalline modification A1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate shows superior properties for drying purposes (no loss of hydrate water can occur) and exhibits a superior behavior in terms of physical stability over varying relative humidity (RH) conditions (physical stable form in the humidity range 0% up to at least 70% RH) as compared to crystalline modification H1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate and crystalline modification NF5 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate. Furthermore, crystalline modification A1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate can be considered the thermodynamically more stable form in comparison with crystalline modification NF3 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate, as shown by competitive slurry conversion experiments with binary mixtures of forms A1 and NF3 in several organic solvents at 25° C. and at 50° C., respectively (see example 10).

In comparison, crystalline modification NF3 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate also shows superior properties for drying purposes (no loss of hydrate water can occur) and exhibits a superior behavior in terms of physical stability over varying relative humidity (RH) conditions (physical stable form in the humidity range 0% up to at least 70% RH) as compared to crystalline modification H1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate and crystalline modification NF5 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate. Furthermore, crystalline modification NF3 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate exhibits a lower kinetic solubility in a mixture of water: acetone (30:70, v:v, after 2 hours) in comparison with crystalline modification A1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate, which enables a higher yield from crystallization processes in this process-relevant solvent mixture (see example 14).

On the other hand, crystalline modification NF5 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate represents a more stable form at high water activity and hence is beneficial in aqueous dispersion systems compared to crystalline modification A1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate, as shown by a competitive slurry conversion experiment with a binary mixture of forms NF5 and A1 in DI water at 25° C. (see example 11)

Furthermore, crystalline modification H1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate represents a stable form at high water activity and hence is beneficial in aqueous dispersion systems compared to crystalline modification NF5 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate, as shown by a competitive slurry conversion experiment and with a binary mixture of forms NF5 and H1 in DI water at 25° C., resulting in form H1 over time (see example 12). Also, crystalline modification H1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate is beneficial in aqueous dispersion systems compared to crystalline modification NF3 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate, as shown by a competitive slurry conversion experiment and with a binary mixture of forms H1 and NF3 in DI water at 25° C., resulting in form H1 over time (see example 13).

With regard to 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate as compared to 6-(1-methyl-1H-pyrazol-4-yl)-2-{3-[5-(2-morpholin-4-yl-ethoxy)-pyrimidin-2-yl]-benzyl}-2H-pyridazin-3-one (free base), the dihydrogenphosphate salt shows a significantly superior stability in aqueous solution and an improved active pharmaceutical ingredient (API) stability in solution.

The crystalline modifications of the present invention can be characterized according to standard methods which can be found e.g. in Rolf Hilfiker, 'Polymorphism in the Pharmaceutical Industry', Wiley-VCH, Weinheim 2006, and references therein, e.g. X-Ray diffraction (XRD; chapter 6), IR and Raman spectroscopy (chapter 5), Differential Scanning Calorimetry (DSC) and Thermogravimetric Analysis (TGA) (chapter 3), Water Vapour Sorption Studies (chapter 9), or which can be found e.g. in H. G. Brittain (editor), Polymorphism in Pharmaceutical Solids, Vol. 95, Marcel Dekker Inc., New York 1999 (chapter 6: all there mentioned techniques).

6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate solvate, preferably 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate, preferably 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate in its crystalline modification, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate in its crystalline modification NF5, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate in its crystalline modification, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate in its crystalline modification A1, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate in its crystalline modification, 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate in its crystalline modification H1 and 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate in its crystalline modification NF3 are hereinafter referred to as "product(s) of the (present) invention".

6-(1-methyl-1H-pyrazol-4-yl)-2-{3-[5-(2-morpholin-4-yl-ethoxy)-pyrimidin-2-yl]-benzyl}-2H-pyridazin-3-one (free base) can be synthesized as described in PCT/EP2008/003473, example 38, and PCT/EP2008/005508, example 1, as follows:

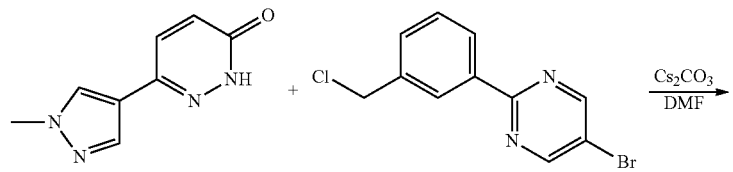

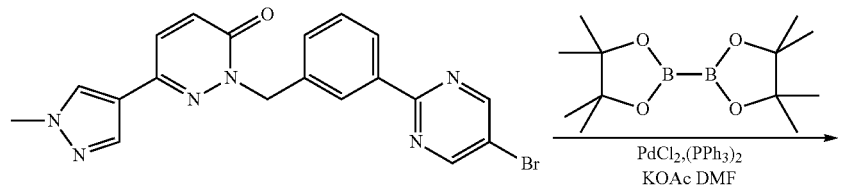

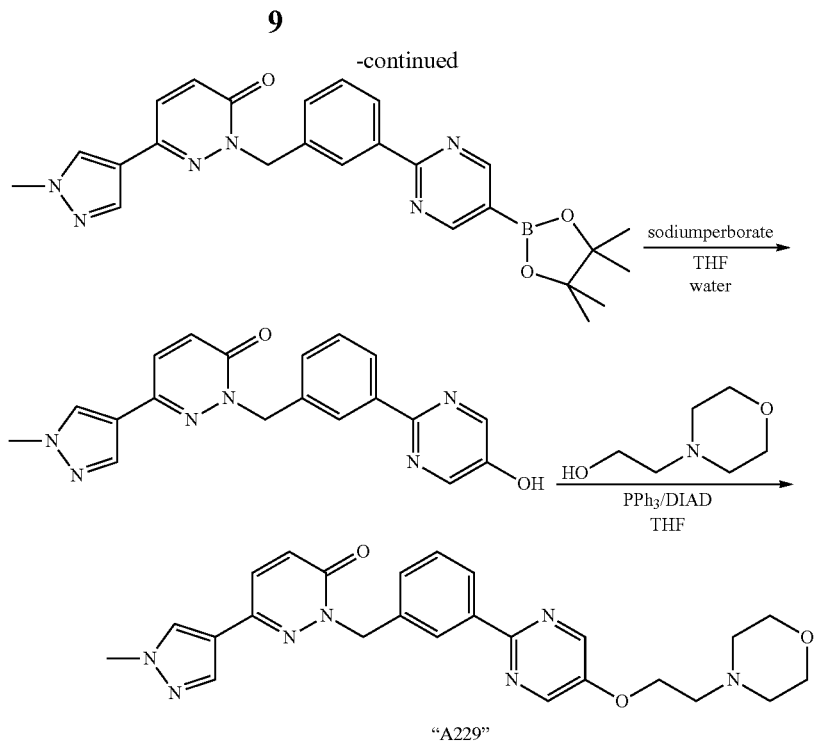

"A229"

A suspension of 7.68 g (43.6 mmol) of 6-(1-methyl-1H-pyrazol-4-yl)-2H-pyridazin-3-one in 90 ml DMF is reacted with 12.4 g (43.6 mmol) of 5-bromo-2-(3-chloromethyl-phenyl)-pyrimidine and 14.2 g (43.6 mmol) of caesium carbonate for 24 hours at room temperature under stirring. The reaction mixture is given to 400 ml water. The resulting precipitate of 2-[3-(5-bromopyrimidin-2-yl)-benzyl]-6-(1-methyl-1H-pyrazol-4-yl)-2H-pyridazin-3-one is sucked off, washed with water and dried in vacuo.

A suspension of 14.0 g (33.0 mmol) of 2-[3-(5-bromopyrimidin-2-yl)-benzyl]-6-(1-methyl-1H-pyrazol-4-yl)-2H-pyridazin-3-one in 65 ml DMF is reacted with 10.9 g (42.9 g) of bis(pinacolato)diboron and 9.72 g (99.0 mmol) of potassium acetate and heated up under nitrogen to 70° C. After 15 minutes of stirring at this temperature 695 mg (0.99 mmol) of bis(triphenylphosphine)-palladium(II)-chloride are added and the reaction mixture is stirred for 18 hours at 70° C. under nitrogen. Subsequently, the reaction mixture is allowed to cool down to room temperature, water and dichloromethane are added, and the reaction mixture is filtrated over diatomite/kieselguhr before the organic phase is separated. The organic phase is then dried over sodium sulfate, concentrated and the residue is re-crystallized from 2-propanol to yield 6-(1-methyl-1H-pyrazol-4-yl)-2-{3-[5-(4,4,5,5-tetramethyl-[1,3,2]dioxaborolan-2-yl)-pyrimidin-2-yl]-benzyl}-2H-pyridazin-3-one.

To a suspension of 13.4 g (28.4 mmol) of 6-(1-methyl-1H-pyrazol-4-yl)-2-{3-[5-(4,4,5,5-tetramethyl-[1,3,2]dioxaborolan-2-yl)-pyrimidin-2-yl]-benzyl}-2H-pyridazin-3-one in 55 ml THF and 55 ml water 8.50 g (85.1 mmol) of sodium perborate is given in portions under ice cooling. The reaction mixture is stirred for two hours at room temperature prior to being sucked off over diatomite/kieselguhr. The filtrate is concentrated in vacuo to approximately half of the original volume and titrated to pH 1 with 2N hydrochloric acid. The resulting precipitate of 2-[3-(5-hydroxy-pyrimidin-2-yl)-benzyl]-6-(1-methyl-1H-pyrazol-4-yl)-2H-pyridazin-3-one is sucked off, washed with water and dried in vacuo.

To a suspension of 360 mg (1.00 mmol) of 2-[3-(5-hydroxy-pyrimidin-2-yl)-benzyl]-6-(1-methyl-1H-pyrazol-4-yl)-2H-pyridazin-3-one in 2 ml THF 394 mg (1.50 mmol) of triphenylphosphine and 242 µl (2.00 mmol) of 4-(2-hydroxyethyl)morpholine are added one after the other. Under ice cooling 294 µl (1.50 mmol) of diisopropylazodicarboxylate are slowly added dropwise. The resulting solution is stirred for 18 hours at room temperature. The reaction mixture is then concentrated in vacuo and the oily residue is dissolved in 2-propanol. The resulting solid of 6-(1-methyl-1H-pyrazol-4-yl)-2-{3-[5-(2-morpholin-4-yl-ethoxy)-pyrimidin-2-yl]-benzyl}-2H-pyridazin-3-one resulted after some time is sucked off, washed with 2-propanol and tert-butylmethylether and dried in vacuo.

Starting product 6-(1-methyl-1H-pyrazol-4-yl)-2H-pyridazin-3-one can be synthesized as described in PCT/EP2008/003473 (pages 65 to 66) as follows:

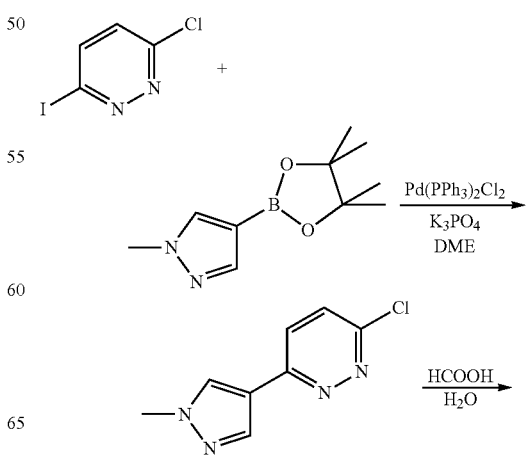

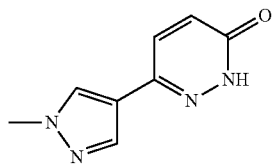

A solution of 815 g (3.39 mol) of 3-chloro-6-iodo-pyridazine in 3.8 l of 1,2-dimethoxyethane is reacted with 705 g (3.39 mol) of 1-methyl-1H-pyrazol-4-boronic acid pinacolester and 1.44 kg tripotassiumphosphate trihydrate. The resulting suspension is heated up to 80° C. under nitrogen and under stirring and 59.5 g (85 mmol) of bis(triphenylphosphine)-palladium(II)-chloride are added. The reaction mixture is stirred for 3 hours at 80° C. Subsequently, the reaction mixture is allowed to cool down to room temperature and 9 l water are added. The resulting precipitate of 3-chloro-6-(1-methyl-1H-pyrazol-4-yl)-pyridazine is sucked off, washed with water and dried in vacuo. A suspension of 615 g (2.90 mol) of 3-chloro-6-(1-methyl-1H-pyrazol-4-yl)-pyridazine in a mixture of 1.86 l formic acid and 2.61 l water is heated up to 80° C. under stirring and is continued to be stirred for 28 hours at this temperature. The reaction mixture is cooled down to room temperature, active coal (activated charcoal) is added, and the mixture is sucked off. The filtrate is titrated under ice cooling with 40% aqueous caustic soda solution to a pH of 7 and subsequently incubated for 16 hours at 6° C. The resulting precipitate of 6-(1-methyl-1H-pyrazol-4-yl)-2H-pyridazin-3-one is sucked off, washed with water and dried in vacuo.

Starting product 5-bromo-2-(3-chloromethyl-phenyl)-pyrimidine can be synthesized as described in PCT/EP2008/003473, example 36, as follows:

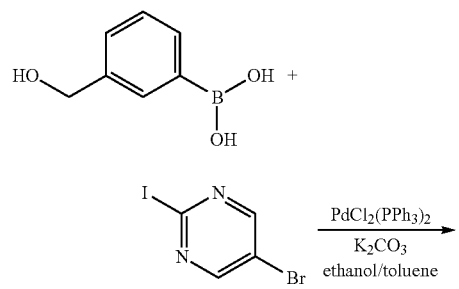

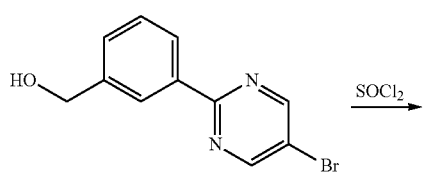

A solution of 95.0 g (332 mmol) of 5-bromo-2-iodopyrimidine in 325 ml toluene kept under nitrogen is reacted with a solution of 70.0 g (660 mmol) of sodium carbonate in 325 ml water the mixture being heated up to 80° C. 2.3 g (3.3 mmol) of bis(triphenylphosphine)-palladium(II)-chloride are added to the reaction mixture and subsequently a solution of 50.0 g (329 mmol) of 3-(hydroxymethyl)-benzeneboronic acid in 650 ml ethanol are added dropwise. The reaction mixture is stirred for 18 hours at 80° C. The reaction mixture is cooled down to room temperature and filtrated. The filtrate is reacted with 1 l ethylacetate and 1 l water. The organic phase is separated, dried over sodiumsulfate and concentrated. The residue of [3-(5-bromopyrimidin-2-yl)-phenyl]-methanol is re-crystallized from 2-propanol.

To 159 ml (2.19 mol) of thionylchloride kept at 30° C. 116 g (438 mmol) of [3-(5-bromopyrimidin-2-yl)-phenyl]-methanol are given in portions under stirring. The reaction mixture is stirred for 18 hours at room temperature. Subsequently, the reaction mixture is concentrated. The remainder is dissolved in toluene and again concentrated. The procedure is repeated three-times. The final remainder of 5-brom-2-(3-chloromethyl-phenyl)-pyrimidine is re-crystallized from toluene.

Alternatively, 6-(1-methyl-1H-pyrazol-4-yl)-2-{3-[5-(2-morpholin-4-yl-ethoxy)-pyrimidin-2-yl]-benzyl}-2H-pyridazin-3-one (free base) can be synthesized as described in PCT/EP2008/003473, example 39, as follows:

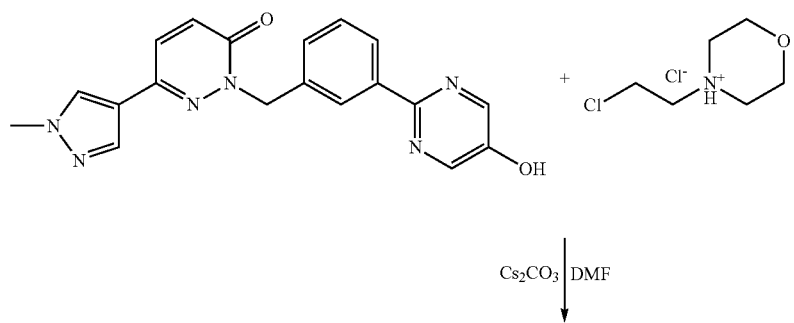

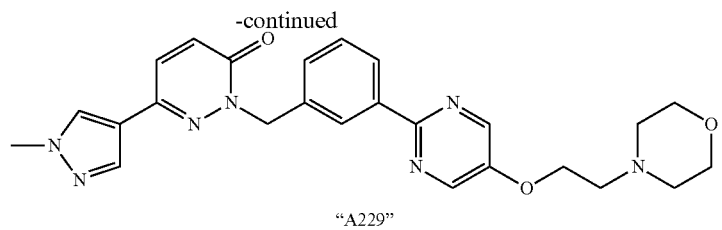

"A229"

A suspension of 360 mg (1.00 mmol) of 2-[3-(5-hydroxy-pyrimidin-2-yl)-benzyl]-6-(1-methyl-1H-pyrazol-4-yl)-2H-pyridazin-3-one, 195 mg (1.05 mmol) of N-(2-chloroethyl)-morpholiniumchloride and 521 mg (1.60 mmol) of caesium carbonate in 2 ml DMF is heated up to 80° C. under stirring and is continued to be stirred for 6 hours at this temperature. Subsequently, the reaction mixture is allowed to cool down and 50 ml water are added. The resulting precipitate of 6-(1-methyl-1H-pyrazol-4-yl)-2-{3-[5-(2-morpholin-4-yl-ethoxy)-pyrimidin-2-yl]-benzyl}-2H-pyridazin-3-one is sucked off, washed with water and dried in vacuo.

In another aspect of the invention, a pharmaceutical composition comprising a therapeutically effective amount of at least one product of the invention is provided.

In a preferred embodiment, the pharmaceutical composition further comprises at least one additional compound selected from the group consisting of physiologically acceptable excipients, auxiliaries, adjuvants, diluents, carriers and/or additional pharmaceutically active substances other than the products of the invention.

A further embodiment of the present invention is a process for the manufacture of said pharmaceutical compositions, characterized in that one or more products of the invention and one or more compounds selected from the group consisting of solid, liquid or semiliquid excipients, auxiliaries, adjuvants, diluents, carriers and pharmaceutically active substances other than the products of the invention, are converted in a suitable dosage form.

As used herein, the term "effective amount" refers to any amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

In another aspect of the invention, a medicament comprising at least one product of the invention or a pharmaceutical composition as described herein is provided.

In a further aspect of the invention, a medicament as described herein for use in the treatment and/or prophylaxis of physiological and/or pathophysiological conditions, which are caused, mediated and/or propagated by the inhibition, regulation and/or modulation of signal transduction of kinases, in particular by the inhibition of tyrosine kinases, preferably Met-kinase, is provided. A corresponding use for the preparation of a medicament for the treatment and/or prophylaxis of the aforementioned conditions is intended to be comprised.

In a further aspect of the invention, a medicament as described herein for use in the treatment and/or prophylaxis of physiological and/or pathophysiological conditions selected from the group consisting of: "cancer, tumour, malignant tumours, benign tumours, solid tumours, sarcomas, carcinomas, hyperproliferative disorders, carcinoids, Ewing sarcomas, Kaposi sarcomas, brain tumours, tumours originating from the brain and/or the nervous system and/or the meninges, gliomas, glioblastomas, neuroblastomas, stomach cancer, kidney cancer, kidney cell carcinomas, prostate cancer, prostate carcinomas, connective tissue tumours, soft tissue sarcomas, pancreas tumours, liver tumours, head tumours, neck tumours, laryngeal cancer, oesophageal cancer, thyroid cancer, osteosarcomas, retinoblastomas, thymoma, testicular cancer, lung cancer, lung adenocarcinoma, small cell lung carcinoma, bronchial carcinomas, breast cancer, mamma carcinomas, intestinal cancer, colorectal tumours, colon carcinomas, rectum carcinomas, gynaecological tumours, ovary tumours/ovarian tumours, uterine cancer, cervical cancer, cervix carcinomas, cancer of body of uterus, corpus carcinomas, endometrial carcinomas, urinary bladder cancer, urogenital tract cancer, bladder cancer, skin cancer, epithelial tumours, squamous epithelial carcinoma, basaliomas, spinaliomas, melanomas, intraocular melanomas, leukaemias, monocyte leukaemia, chronic leukaemias, chronic myelotic leukaemia, chronic lymphatic leukemia, acute leukaemias, acute myelotic leukaemia, acute lymphatic leukaemia and/or lymphomas" is provided. A corresponding use for the preparation of a medicament for the treatment and/or prophylaxis of the aforementioned conditions is intended to be comprised.

In another aspect of the invention, a medicament as described herein is provided, wherein in such medicament comprises at least one additional pharmacologically active substance (drug, ingredient).

In a preferred embodiment the at least one pharmacologically active substance is a substance as described herein.

In another aspect of the invention, a medicament as described herein is provided, wherein the medicament is applied before and/or during and/or after treatment with at least one additional pharmacologically active substance.

In a preferred embodiment the at least one pharmacologically active substance is a substance as described herein.

In a further aspect of the invention, a kit comprising a therapeutically effective amount of at least one product of the invention and/or at least one pharmaceutical composition as described herein and a therapeutically effective amount of at least one further pharmacologically active substance other than the products of the invention is provided.

Products of the invention may be used in combination with one or more other pharmacologically active substances (ingredients, drugs) in the treatment, prevention, suppression or amelioration of diseases or conditions for which products of the invention or the other substances have utility. Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a product of the invention. When a product of the invention is used contemporaneously with one or more other drugs, a combination product containing such other drug(s) and the product of the invention is preferred. However, combination therapy also includes therapies in which the product of the invention and one or more other drugs are administered on different overlapping schedules. It is contemplated that when used in combination with other active ingredients, the product of the present invention or the other active ingredient or both may be used effectively in lower doses than when each is used alone. Accordingly, the pharmaceutical compositions of the present invention (pharmaceutical compositions as described herein) include those that contain one or more other active ingredients, in addition to a product of the invention.

Examples of other pharmacologically active substances (ingredients, drugs) that may be administered in combination with a product of the invention, and either administered separately or in the same pharmaceutical composition, include, but are not limited to the compounds classes and specific compounds listed in Table 1:

TABLE 1

| | | |
|---|---|---|
| Alkylating agents | Cyclophosphamide | Lomustine |
| | Busulfane | Procarbazine |
| | Ifosfamide | Altretamine |
| | Melphalane | Estramustinphosphate |
| | Hexamethylmelamine | Mechlorethamine |
| | Thiotepa | Streptozocine |
| | Chlorambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (AeternaZentaris) |
| | Carboxyphthalatoplatinum | Satraplatin (Johnson Matthey) |
| | Tetraplatin | BBR-3464 (Hoffmann-La |
| | Ormiplatin | Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycine |
| | 5-Fluoruracil | Fludarabine |
| | Floxuridine | Pentostatine |
| | 2-Chlordesoxyadenosine | Raltitrexede |
| | 6-Mercaptopurine | Hydroxyurea |
| | 6-Thioguanine | Decitabine (SuperGen) |
| | Cytarabine | Clofarabine (Bioenvision) |
| | 2-Fluordesoxycytidine | Irofulven (MGI Pharma) |
| | Methotrexate | DMDC (Hoffmann-La Roche) |
| | Idatrexate | Ethinylcytidine (Taiho) |
| Topoisomerase inhibitors | Amsacrine | Rubitecane (SuperGen) |
| | Epirubicine | Exatecanmesylate (Daiichi) |
| | Etoposide | Quinamed (ChemGenex) |
| | Teniposide or Mitoxantrone | Gimatecane (Sigma-Tau) |
| | Irinotecane (CPT-11) | Diflomotecane (Beaufour-|
| | 7-Ethyl-10- | Ipsen) |
| | hydroxycamptothecine | TAS-103 (Taiho) |
| | Topotecane | Elsamitrucine (Spectrum) |
| | Dexrazoxanet (TopoTarget) | J-107088 (Merck & Co) |
| | Pixantrone (Novuspharrna) | BNP-1350 (BioNumerik) |
| | Rebeccamycin-Analogue | CKD-602 (Chong Kun Dang) |
| | (Exelixis) | KW-2170 (Kyowa Hakko) |
| | BBR-3576 (Novuspharrna) | |
| Antitumor antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycinsulfate (Blenoxan) |
| | Epirubicin | Bleomycinacid |
| | Therarubicin | Bleomycin A |
| | Idarubicin | Bleomycin B |
| | Rubidazone | Mitomycin C |
| | Plicamycinp | MEN-10755 (Menarini) |
| | Porfiromycin | GPX-100 (Gem |
| | Cyanomorpholinodoxorubicin | Pharmaceuticals) |
| | Mitoxantron (Novantron) | |
| Antimitotic agents | Paclitaxel | SB 408075 (GlaxoSmithKline) |
| | Docetaxel | E7010 (Abbott) |
| | Colchicin | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatine 10 (NCI) | D 24851 (ASTA Medica) |

TABLE 1-continued

| | | |
|---|---|---|
| | Rhizoxine (Fujisawa) | ER-86526 (Eisai) |
| | Mivobuline (Warner-Lambert) | Combretastatine A4 (BMS) |
| | Cemadotine (BASF) | Isohomohalichondrin-B |
| | RPR 109881A (Aventis) | (PharmaMar) |
| | TXD 258 (Aventis) | ZD 6126 (AstraZeneca) |
| | Epothilon B (Novartis) | PEG-Paclitaxel (Enzon) |
| | T 900607 (Tularik) | AZ10992 (Asahi) |
| | T 138067 (Tularik) | !DN-5109 (Indena) |
| | Cryptophycin 52 (Eli Lilly) | AVLB (Prescient NeuroPharma) |
| | Vinflunine (Fabre) | Azaepothilon B (BMS) |
| | Auristatine PE (Teikoku Hormone) | BNP-7787 (BioNumerik) |
| | BMS 247550 (BMS) | CA-4-Prodrug (OXiGENE) |
| | BMS 184476 (BMS) | Dolastatin-10 (NrH) |
| | BMS 188797 (BMS) | CA-4 (OXiGENE) |
| | Taxoprexine (Protarga) | |
| Aromatase inhibitors | Aminoglutethimide | Exemestane |
| | Letrozole | Atamestane (BioMedicines) |
| | Anastrazole | YM-511 (Yamanouchi) |
| | Formestane | |
| Thymidylatesynthase inhibitors | Pemetrexed (Eli Lilly) | Nolatrexed (Eximias) |
| | ZD-9331 (BTG) | CoFactor™ (BioKeys) |
| DNA antagonists | Trabectedine (PharmaMar) | Mafosfamide (Baxter International) |
| | Glufosfamide (Baxter International) | Apaziquone (Spectrum |
| | Albumin + 32P (Isotope Solutions) | Pharmaceuticals) |
| | Thymectacine (NewBiotics) | O6-Benzylguanine (Paligent) |
| | Edotreotide (Novartis) | |
| Farnesyltransferase inhibitors | Arglabine (NuOncology Labs) | Tipifarnibe (Johnson & Johnson) |
| | Ionafarnibe (Schering-Plough) | Perillylalcohol (DOR Bio-Pharma) |
| | BAY-43-9006 (Bayer) | |
| Pump inhibitors | CBT-1 (CBA Pharma) | Zosuquidar-Trihydrochloride |
| | Tariquidar (Xenova) | (Eli Lilly) |
| | MS-209 (Schering AG) | Biricodar-Dicitrate (Vertex) |
| Histoneacetyltransferase inhibitors | Tacedinaline (Pfizer) | Pivaloyloxymethylbutyrate |
| | SAHA (Aton Pharma) | (Titan) |
| | MS-275 (Schering AG) | Depsipeptide (Fujisawa) |
| Metalloproteinase inhibitors/ | Neovastat (Aeterna Laboratories) | CMT-3 (CollaGenex) |
| | | BMS-275291 (Celltech) |
| Ribonucleosidereduktase inhibitors | Marimastat (British Biotech) | Tezacitabine (Aventis) |
| | Galliummaltolate (Titan) | Didox (Molecules for Health) |
| | Triapine (Vion) | |
| TNF-alpha agonists/ antagonists | Virulizine (Lorus Therapeutics) | Revimide (Celgene) |
| | CDC-394 (Celgene) | |
| Endotheline-A receptor antagonists | Atrasentane (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | Pentrix (Australian Cancer Technology) |
| | GMK (Progenics) | |
| | Adenocarzinoma vaccine (Biomira) | JSF-154 (Tragen) |
| | | Cancer vaccine (Intercell) |
| | CTP-37 (AVI BioPharma) | Noreline (Biostar) |
| | JRX-2 (Immuno-Rx) | BLP-25 (Biomira) |
| | PEP-005 (Peplin Biotech) | MGV (Progenics) |
| | Synchrovax vaccine (CTL Immuno) | 13-Alethine (Dovetail) |
| | | CLL-Thera (Vasogen) |
| | Melanoma vaccine (CTL Immuno) | |
| | p21-RAS vaccine (GemVax) | |
| Hormonal and anti-hormonal agents | Estrogens | Prednisone |
| | Conjugated Estrogens | Methylprednisolone |
| | Ethinylestradiole | Prednisolone |
| | Chlorotrianisen | Aminoglutethimide |
| | Idenestrole | Leuprolide |
| | Hydroxyprogesteroncaproate | Goserelin |
| | Medroxyprogesterone | Leuporelin |
| | Testosterone | Cetrorelix |
| | Testosteronpropionate | Bicalutamide |
| | Fluoxymesterone | Flutamide |
| | Methyltestosterone | Octreotide |
| | Diethylstilbestrole | Nilutamide |
| | Megestrole | Mitotane |
| | Tamoxifen | P-04 (Novogen) |
| | Toremofine | 2-Methoxyestradiol (EntreMed) |
| | Dexamethasone | |
| | | Arzoxifen (Eli Lilly) |
| Photodynamic agents | Talaporfine (Light Sciences) | Pd-Bacteriopheophorbide (Yeda) |
| | Theralux (Theratechnologies) | |
| | Motexafin Gadolinium | Lutetium-Texaphyrine |

TABLE 1-continued

| | | |
|---|---|---|
| | (Pharmacyclics) | (Pharmacyclics) |
| | | Hypericine |
| Tyrosinkinase inhibitors | Imatinib (Novartis) | Kahalid F (PharmaMar) |
| | Leflunomid | CEP-701 (Cephalon) |
| | (Sugen/Pharmacia) | CEP-751 (Cephalon) |
| | ZDI839 (AstraZeneca) | MLN518 (Millenium) |
| | Erlotinib (Oncogene Science) | PKC412 (Novartis) |
| | Canertjnib (Pfizer) | Phenoxodiol O |
| | Squalamin (Genaera) | Trastuzumab (Genentech) |
| | SU5416 (Pharmacia) | C225 (ImClone) |
| | SU6668 (Pharmacia) | rhu-Mab (Genentech) |
| | ZD4190 (AstraZeneca) | MDX-H210 (Medarex) |
| | ZD6474 (AstraZeneca) | 2C4 (Genentech) |
| | Vatalanib (Novartis) | MDX-447 (Medarex) |
| | PKI166 (Novartis) | ABX-EGF (Abgenix) |
| | GW2016 (GlaxoSmithKline) | IMC-1C11 (ImClone) |
| | EKB-509 (Wyeth) | |
| | EKB-569 (Wyeth) | |
| Different agents | SR-27897 (CCK-A inhibitor, Sanofi-Synthelabo) | BCX-1777 (PNP inhibitor, BioCryst) |
| | Tocladesine (cyclic-AMP agonist, Ribapharm) | Ranpirnase (Ribonuclease stimulans, Alfacell) |
| | Alvocidib (CDK inhibitor, Aventis) | Galarubicin (RNA synthesis inhibitor, Dong-A) |
| | CV-247 (COX-2-Inhibitor, Ivy Medical) | Tirapazamin (reducing agent, SRI International) |
| | P54 (COX-2 inhibitor, Phytopharm) | N-Acetylcystein (reducing agent, Zambon) |
| | CapCell ™ (CYP450 stimulans, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (Gastrin inhibitor, Aphton) | Seocalcitol (Vitamin-D receptor agonist, Leo) |
| | Efaproxiral (Oxygenator, Allos Therapeutics) | 131-I-TM-601 (DNA antagonist, TransMolecular) |
| | PI-88 (Heparanase inhibitor, Progen) | Eflornithin (ODC inhibitor, ILEX Oncology) |
| | Tesmilifen (Histamine antagonist, YM BioSciences) | Minodronic acid (Osteoclasts inhibitor, Yamanouchi) |
| | Histamine (Histamine-H2 receptor agonist, Maxim) | Indisulam (p53 stimulans, Eisai) |
| | Tiazofurin (IMPDH inhibitor, Ribapharm) | Aplidin (PPT inhibitor, PharmaMar) |
| | Cilengitide (Integrine antagonist, Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (Hematopoesis enhancer, Pharmagenesis) |
| | Exisulind (PDE-V inhibitor, Cell Pathways) | Immunol ™ (Triclosan oral irrigation, Endo) |
| | CP-461 (PDE-V inhibitor, Cell Pathways) | Triacetyluridine (Uridine prodrug, Wellstat) |
| | AG-2037 (GART inhibitor, Pfizer) | SN-4071 (sarcoma agent, Signature BioScience) |
| | WX-UK1 (Plasminogen activator inhibitor, Wilex) | TransMID-107 ™ (Immunotoxine, KS Biomedix) |
| | PBI-1402 (PMN stimulans, ProMetic LifeSciences) | PCK-3145 (Apoptosis enhancer, Procyon) |
| | Bortezomib (Proteasome inhibitor, Millennium) | Doranidazole (Apoptosis enhancer, Pola) |
| | SRL-172 (T-cell stimulans, SR Pharma) | CHS-828 (cytotoxic agent, Leo) |
| | TLK-286 (Glutathione-S-transferase inhibitor, Telik) | trans-Retinoic acid (Differentiator, NIH) |
| | PT-100 (Growth factor agonist, Point Therapeutics) | MX6 (Apoptosis enhancer, MAXIA) |
| | Midostaurin (PKC inhibitor, Novartis) | Apomin (Apoptosis enhancer, ILEX Oncology) |
| | Bryostatin-1 (PKC stimulans, GPC Biotech) | Urocidine (Apoptosis enhancer, Bioniche) |
| | CDA-II (Apoptosis enhancer, Everlife) | Ro-31-7453 (Apoptosis enhancer, La Roche) |
| | SDX-101 (Apoptosis enhancer Salmedix) | Brostallicin (Apoptosis enhancer, Pharmacia) |
| | Ceflatonin (Apoptosis enhancer, ChemGenex) | |

In a preferred embodiment, a product of the invention is administered in combination with one or more known antitumor agents, such as the following: estrogen receptor modulators, androgen receptor modulators, retinoid receptor modulators, cytotoxics, antiproliferative agents, prenyl proteintransferase inhibitors, HMG-CoA-reductase inhibitors, HIV protease inhibitors, reverse transcriptase inhibitors, angiogenesis inhibitors.

The products of the invention are in particular well suited for administration in combination with radiotherapy. The synergistic effects of VEGF inhibition in combination with radiotherapy are known to the skilled artisan (WO 00/61186).

The term "estrogen receptor modulators" in the course of the present invention refers to compounds that interfere with or inhibit the binding of estrogen to estrogen receptor—independently from the mode of action. Non-limiting examples of estrogen receptor modulators are tamoxifen, raloxifen, idoxifen, LY353381, LY 117081, toremifen, fulvestrant, 4-[7-(2, 2-Dimethyl-1-oxopropoxy-4-methyl-2-[4-[2-(1-piperidinyl) ethoxy]phenyl]-2H-1-benzopyran-3-yl]phenyl-2,2-dimethyl-propanoate, 4,4'-Dihydroxybenzophenone-2,4-dinitrophenylhydrazone and SH646.

The term "androgen receptor modulators" in the course of the present invention refers to compounds that interfere with or inhibit the binding of androgens to androgen receptor—independently from the mode of action. Non-limiting examples of androgen receptor modulators are finasteride and other 5alpha-reductase inhibitors, nilutamide, flutamide, bicalutamide, liarozole and abirateron acetate.

The term "retinoid receptor modulators" in the course of the present invention refers to compounds that interfere with or inhibit the binding of retinoids to retinoid receptor—independently from the mode of action. Non-limiting examples of retinoid receptor modulators are bexaroten, tretinoin, 13-cis-retinoic acid, 9-cis-retinoic acid, alpha-difluoromethylornithine, ILX23-7553, trans-N-(4'-Hydroxyphenyl)retinamide and N-4-carboxyphenylretinamide.

The term "cytotoxics" in the course of the present invention refers to compounds that primarily trigger cell death through direct action on cell function(s) or which interfere with or inhibit cell myosis, such as alkylating agents, tumor necrosis factors, intercalating agents, microtubule inhibitors and topoisomerase inhibitors. Non-limiting examples of cytotoxics are tirapazimin, sertenef, cachectine, ifosfamide, tasonermine, lonidamine, carboplatin, altretamine, prednimustine, dibromodulcit, ranimustine, fotemustine, nedaplatin, oxaliplatin, temozolomide, heptaplatin, estramustin, improsulfantosylate, trofosfamide, nimustine, dibrospidium-chloride, pumitepa, lobaplatin, satraplatin, profiromycin, cisplatin, irofulven, dexifosfamide, cis-amindichloro(2-methylpyridine)platin, benzylguanine, glufosfamide, GPX100, (trans, trans,trans)-bis-mu-(hexane-1,6-diamine)-mu-[diamine-platin(II)]bis-[diamine(chloro)platin(II)]-tetrachloride, diarizidinylspermine, arsenium trioxide, 1-(11-Dodecylamino-10-hydroxyundecyl)-3,7-dimethylxanthine, zorubicin, idarubicin, daunorubicin, bisantren, mitoxantron, pirarubicin, pinafide, valrubicine, amrubicine, antineoplaston, 3'-desamino-3'-morpholino-13-desoxo-10-hydroxycaminomycin, annamycin, galarubicin, elinafide, MEN10755 and 4-desmethoxy-3-desamino-3-aziridinyl-4-methylsulfonyl-daunorubicin (WO 00/50032).

Non-limiting examples of microtubule inhibitors are paclitaxel, vindesine-sulfate, 3',4'-dideshydro-4'-desoxy-8'-norvincaleukoblastine, docetaxol, rhizoxine, dolastatine, mivobuline-isethionate, auristatine, cemadotine, RPR109881, BMS184476, vinflunine, cryptophycine, 2,3,4,5,6-pentafluoro-N-(3-fluoro-4-methoxyphenyl)-benzenesulfonamide, anhydrovinblastine, N,N-dimethyl-L-valyl-L-valyl-N-methyl-L-valyl-L-prolyl-L-proline-t-butylamide, TDX258 and BMS188797.

Non-limiting examples of topoisomerase inhibitors are topotecane, hycaptamine, irinotecane, rubitecane, 6-ethoxypropionyl-3',4'-O-exo-benzylidene-chartreusine, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo-[de]-pyrano-[3',4':b,7] indolizino[1,2b]quinoline-10,13(9H,15H)-dione, lurtotecane, 7-[2-(N-isopropylamino)ethyl]-(20S)camptothecine, BNP1350, BNPI1100, BN80915, BN80942, etoposide-phosphate, teniposide, sobuzoxane, 2'-dimethylamino-2'-desoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-aminoethyl)amino]-benzo[g]isoquinoline-5,10-dione, 5-(3-aminopropylamino)-7,10-dihydroxy-2-(2-hydroxyethylaminomethyl)-6H-pyrazolo[4,5,1-de]-acridine-6-one, N-[1-[2(diethylamino) ethylamino]-7-methoxy-9-oxo-9H-thioxane-then-4-ylmethyl]formamide, N-(2-(dimethyl-amino)-ethyl) acridine-4-carboxamide, 6-[[2-(dimethylamino)-ethyl] amino]-3-hydroxy-7H-indeno[2,1-c]quinolin-7-one and dimesna.

Non-limiting examples of antiproliferative agents are anti-sense RNA- and anti-sense-DNA oligonucleotides, such as G3139, ODN698, RVASKRAS, GEM231 and INX3001, as well as antimetabolites such as enocitabine, carmofur, tegafur, pentostatine, doxifluridine, trimetrexate, fludarabine, capecitabine, galocitabine, cytarabinocfosfate, fosteabine sodiumhydrate, raltitrexed, paltitrexide, emitefur, tiazofurine, decitabine, nolatrexed, pemetrexed, nelzarabine, 2'-desoxy-2'-methylidencytidine, 2'-fluoromethylen-2'-desoxycytidine, N-[5-(2,3-dihydrobenzofuryl)sulfonyl]-N'-(3,4-dichlorophenyl)urea, N6-[4-desoxy-4-[N2-[2(E),4(E)-tetradecadienoyl]glycylamino]-L-glycero-B-L-manno-heptopyranosyl]adenine, aplidine, ecteinascidine, troxacitabine, 4-[2-amino-4-oxo-4,6,7,8-tetrahydro-3H-pyrimidino[5,4-b][1,4]thiazine-6-yl-(S)-ethyl]-2,5-thienoyl-L-glutaminic acid, aminopterine, 5-fluorouracil, alanosine, 11-acetyl-8-(carbamoyloxymethyl)-4-formyl-6-methoxy-14-oxa-1,11-diaza-tetracyclo-(7.4.1.0.0)-tetradeca-2,4,6-trien-9-ylacetic acid ester, swainsonine, lometrexol, dexrazoxane, methioninase, 2'-cyan-2'-desoxy-N4-palmitoyl-1-B-D-arabinofuranosylcytosine and 3-aminopyridine-2-carboxaldehyde-thiosemicarbazone.

"Antiproliferative agents" also comprises monoclonal antibodies against growth factors that have not been listed under "angiogenesis inhibitors", such as trastuzumab, as well as tumor suppressor genes, such as p53.

The pharmaceutical compositions of the present invention (as described herein) may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

tablets: mixing of active ingredient/s and auxiliaries, compression of said mixture into tablets (direct compression), optionally granulation of part of mixture before compression.

capsules: mixing of active ingredient/s and auxiliaries to obtain a flowable powder, optionally granulating powder, filling powders/granulate into opened capsules, capping of capsules.

semi-solids (ointments, gels, creams): dissolving/dispersing active ingredient/s in an aqueous or fatty carrier; subsequent mixing of aqueous/fatty phase with complementary fatty/aqueous phase, homogenization (creams only).

suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more products of the invention into a dosage form suitable for administration to a patient in need of such a treatment. Usually, the transfer of one or more products of the invention into such a dosage form comprises the addition of one or more compounds, selected from the group consisting of carriers, excipients, auxiliaries and pharmaceutical active ingredients other than the products of the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition. In this respect, active ingredients are preferably at least one product of the invention and one or more additional compounds other than the products of the invention, which show valuable pharmaceutical properties, preferably those pharmaceutical active agents other than the products of the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The products of the invention may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the products of the invention, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The products of the invention can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the products of the present invention will be in the form of pharmaceutically acceptable salts. Other salts may, however, be useful in the preparation of the products of the invention or of their pharmaceutically acceptable salts. Suitable pharmaceutically acceptable salts of the products of the invention include acid addition salts which may, for example be formed by mixing a solution of the product of the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the products of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the products of the invention is known to the skilled artisan or can be easily determined by standard methods known in the art.

The products of the invention and the additional pharmacologically active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For the purpose of the present invention, all mammalian species are regarded as being comprised. In a preferred embodiment, such mammals are selected from the group consisting of "primate, human, rodent, equine, bovine, canine, feline, domestic animals, cattle, livestock, pets, cow, sheep, pig, goat, horse, pony, donkey, hinny, mule, hare, rabbit, cat, dog, guinea pig, hamster, rat, mouse". More preferably, such mammals are humans. Animal models are of interest for experimental investigations, providing a model for treatment of human diseases.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of many disorders, the susceptibility of a particular cell to treatment with the subject compounds may be determined by in vitro testing. Typically a culture of the cell is combined with a subject compound at varying concentrations for a period of time sufficient to allow the active agents to show a relevant reaction, usually between about one hour and one week. For in vitro testing, cultured cells from a biopsy sample may be used.

The object of the present invention has surprisingly been solved in another aspect by providing a process for manufacturing crystalline modification A1 of 6-(1-methyl-1H-pyrazol-4-yl)-2-{3-[5-(2-morpholin-4-yl-ethoxy)-pyrimidin-2- yl]-benzyl}-2H-pyridazin-3-one dihydrogenphosphate anhydrate comprising the steps:
- (a) dissolving or dispersing 6-(1-methyl-1H-pyrazol-4-yl)-2-{3-[5-(2-morpholin-4-yl-ethoxy)-pyrimidin-2-yl]-benzyl}-2H-pyridazin-3-one (free base) or one or more salts thereof in a solvent or a solvent mixture, preferably 2-propanol or chloroform, optionally under stirring,
- (b) converting 6-(1-methyl-1H-pyrazol-4-yl)-2-{3-[5-(2-morpholin-4-yl-ethoxy)-pyrimidin-2-yl]-benzyl}-2H-pyridazin-3-one (free base) or one or more salts thereof into the corresponding dihydrogenphosphate salt by addition of aqueous or ethanolic phosphoric acid solution, optionally under stirring,
- (c) stirring the resulting dispersion of step (b) at room temperature for one or more hours or days, preferably for 1 or 2 hours,
- (d) recovering precipitated 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate by filtration, optionally subsequent washing with a solvent or a solvent mixture, and optionally subsequent drying, preferably in vacuo, optionally at elevated temperature T, preferably 30° C. to 95° C., more preferably 70° C.

In the course of the present invention, the terms "elevated temperature" and "elevated temperature T or $T_x$" (with x=1, 2, 3 etc.)" refer to an individual specific temperature for a given process step or sub-step that is independent from any other "elevated temperature" and that can be any temperature within the temperature range from "above room temperature" to "boiling temperature" of a given solvent or solvent mixture and/or "melting temperature" of a given solid, educt, intermediate or product or mixture thereof, whatever applies.

In the course of the present invention, the term "one or more salts of 6-(1-methyl-1H-pyrazol-4-yl)-2-{3-[5-(2-morpholin-4-yl-ethoxy)-pyrimidin-2-yl]-benzyl}-2H-pyridazin-3-one (free base)" refers to any and all salts, preferably pharmaceutically acceptable salts, of 6-(1-methyl-1H-pyrazol-4-yl)-2-{3-[5-(2-morpholin-4-yl-ethoxy)-pyrimidin-2-yl]-benzyl}-2H-pyridazin-3-one (free base), which include, but are not limited to, acetate, adipate, alginate, arginate, aspartate, benzoate, benzolsulphonate (besylate), bisulphate, bisulphite, bromide, butyrate, bampforat, campforsulphonate, caprylate, chloride, chlorobenzoate, citrate, cyclopentanpropionate, digluconate, dihydrogenphosphate, dinitrobenzoate, dodecylsulphate, ethanesulphonate, fumarate, galacterate, galacturonate, glucoheptanoate, gluconate, glutamate, glycerophosphate, hemisuccinate, hemisulphate, heptanoate, hexanoate, hippurate, hydrochloride, hydrobromide, hydroiodide, 2-hydroxyethansulphonate, iodide, isothionate, isobutyrate, lactate, lactobionate, malate, maleate, malonate, mandelate, metaphosphate, methansulphonate, methylbenzoate, monohydrogenphosphate, 2-naphthalinsulphonate, nicotinate, nitrate, oxalate, oleate, pamoate, pectinate, persulphate, phenylacetate, 3-phenylpropionate, phosphate, phosphonate, and phthalate.

In the course of the present invention, the term "a solvent or a solvent mixture" refers to any and all solvents, preferably organic solvents and water, more preferably pharmaceutically acceptable organic solvents and water, which include, but are not limited to, methanol, ethanol, 2-propanol, n-butanol, iso-butanol, acetone, methylethylketone, ethylacetate, 1,4-dioxane, diethylether, MTBE, THF, acetonitrile, dichloromethane, chloroform, DMF, cyclohexane, cyclopentane, n-hexane, n-heptane, n-pentane, toluene, o-xylene, p-xylene, DMSO, pyridine, acetic acid, anisole, butylacetate, cumene, ethylformate, formic acid, iso-butylacetate, iso-propylacetate, methylacetate, 3-methyl-1-butanol, methylisobutylketone, 2-methyl-1-propanol, 1-pentanol, propylacetate, ethyleneglycol, and 1-methyl-2-pyrrolidone, as well as any and all mixtures of two or more such solvents, preferably binary mixtures, more preferably binary mixtures of water and a pharmaceutically acceptable organic solvent.

The object of the present invention has surprisingly been solved in another aspect by providing a process for manufacturing crystalline modification A1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate comprising the steps:
- (a) dispersing 6-(1-methyl-1H-pyrazol-4-yl)-2-{3-[5-(2-morpholin-4-yl-ethoxy)-pyrimidin-2-yl]-benzyl}-2H-pyridazin-3-one (free base) or one or more salts thereof in a solvent or a solvent mixture, preferably in water, and addition of aqueous phosphoric acid solution, optionally under stirring,
- (b) heating the resulting dispersion of step (a) up to elevated temperature T1, preferably 30° C. to 95° C., more preferably 50° C., optionally under stirring, and cooling down the resulting solution, preferably to 0° C. to 40° C., more preferably to 20° C., optionally under stirring, before diluting it with a solvent or a solvent mixture, preferably acetone, optionally under stirring,
- (c) stirring the resulting dispersion of step (b) at 0° C. to 40° C., preferably 10° C., until crystallization is complete and/or incubating it at room temperature for one or more hours or days, optionally under stirring,
- (d) recovering precipitated 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate by filtration, optionally cooling down the resulting dispersion of step (c) to 0° C. to 20° C., preferably 5° C., prior to filtration optionally under stirring, optionally subsequent washing with a solvent or a solvent mixture, preferably acetone, and optionally subsequent drying, preferably in vacuo, optionally at elevated temperature T2, preferably 30° C. to 95° C., more preferably 70° C.,
- (e) optionally, boiling the resulting dried crystals of step (d) in a solvent or a solvent mixture, preferably ethanol, as dispersion for one or more minutes, preferably 30 minutes, and recovering them by filtration from the hot dispersion.

The object of the present invention has surprisingly been solved in another aspect by providing a process for manufacturing crystalline modification A1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate comprising the steps:
- (a) dispersing 6-(1-methyl-1H-pyrazol-4-yl)-2-{3-[5-(2-morpholin-4-yl-ethoxy)-pyrimidin-2-yl]-benzyl}-2H-pyridazin-3-one (free base) or one or more salts thereof in a solvent mixture, preferably in water:acetone mixtures, and addition of aqueous phosphoric acid solution, optionally under stirring,
- (b) heating the resulting dispersion of step (a) up to elevated temperature T1, preferably 30° C. to 95° C., more preferably 55° C., optionally under stirring, and cooling down the resulting solution, preferably to 0° C. to 50° C., optionally under stirring, with a defined cooling rate, preferably 0.1-1 K/min, more preferably 0.1-0.3 K/min, optionally under stirring, until crystallization sets in, (c) further cooling the resulting dispersion of step (b) preferably to −20° C. to 0° C., more preferably to −10° C., optionally under stirring, with a defined cooling rate, preferably 0.1-1 K/min, more preferably 0.1-0.3 K/min, optionally under stirring, (d) stirring the resulting dispersion of step (c) at −20° C. to 40° C., preferably −10° C., until crystallization is complete, (e) recovering crystallized 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate by filtration, optionally subsequent washing with a solvent or a solvent mixture, preferably acetone, and optionally subsequent drying, preferably in vacuo, optionally at elevated temperature T2, preferably 30° C. to 95° C., more preferably 70° C.

The object of the present invention has surprisingly been solved in another aspect by providing a process for manufacturing crystalline modification H1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate comprising the steps:

(a) spreading 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate crystalline modification A1 onto a surface, preferably a bordered surface of a container, more preferably of a Petri dish, and subsequently incubating it in a sealed desiccator over water or aqueous salt solutions with defined relative humidity (RH), preferably 80-100% RH, more preferably 90-100% RH, for one or more days or weeks.

The object of the present invention has surprisingly been solved in another aspect by providing a process for manufacturing crystalline modification H1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate comprising the steps:

(a) dispersing 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate crystalline modification A1 in a mixture of two or more solvents, preferably a binary mixture of water and an organic solvent, where preferably the organic solvent is selected from the group consisting of: "methanol, ethanol, 2-propanol, acetone, TFH and acetonitrile", optionally under stirring, and stirring the resulting dispersion at elevated temperature T1, preferably 30° C. to 95° C., more preferably 50° C., for one or more days or weeks, (b) recovering precipitated 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate by filtration, optionally subsequent washing with a solvent or a solvent mixture, and optionally subsequent drying, preferably in vacuo, optionally at elevated temperature T2, preferably 30° C. to 95° C., more preferably 70° C.

The object of the present invention has surprisingly been solved in another aspect by providing a process for manufacturing crystalline modification NF3 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate comprising the steps:

(a) dispersing or dissolving 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate crystalline modification A1 in a mixture of two or more solvents, preferably a binary mixture, where preferably the solvents are selected from the group consisting of: "water, methanol, ethanol, 2-propanol, acetone, TFH, acetonitrile and 1,4-dioxane", optionally under stirring, and subsequently evaporating the mixture of two or more solvents at room temperature or elevated temperature T1, preferably 30° C. to 95° C., more preferably 50° C. until crystallization occurs, (b) recovering precipitated 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate by filtration, optionally subsequent washing with a solvent or a solvent mixture, and optionally subsequent drying, preferably in vacuo, optionally at elevated temperature T2, preferably 30° C. to 95° C., more preferably 70° C.

The object of the present invention has surprisingly been solved in another aspect by providing a process for manufacturing crystalline modification NF5 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate comprising the steps:

(a) dissolving 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate crystalline modification A1 into a binary solvent mixture, preferably water:methanol, most preferably in a ratio of 1:1 (v:v), and quickly evaporating the solvent mixture at elevated temperature, preferably 40-80° C., most preferably 60° C., under vacuum until a precipitate is obtained, (b) optionally further spreading the precipitate obtained from step (a) as a powder onto a surface, preferably a bordered surface of a container, more preferably of a Petri dish, and subsequently incubating it in a sealed desiccator over water or aqueous salt solutions with defined relative humidity (RH), preferably 80-100% RH, more preferably 90-100% RH, for one or more days or weeks.

The object of the present invention has surprisingly been solved in another aspect by providing a process for manufacturing crystalline modification NF5 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate comprising the step:

(a) spreading 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate crystalline form NF3 as a powder onto a surface, preferably a bordered surface of a container, more preferably of a Petri dish, and subsequently incubating it in a sealed desiccator over water or aqueous salt solutions with defined relative humidity (RH), preferably 80-100% RH, more preferably 90-100% RH, for one or more days or weeks.

Figure 1:
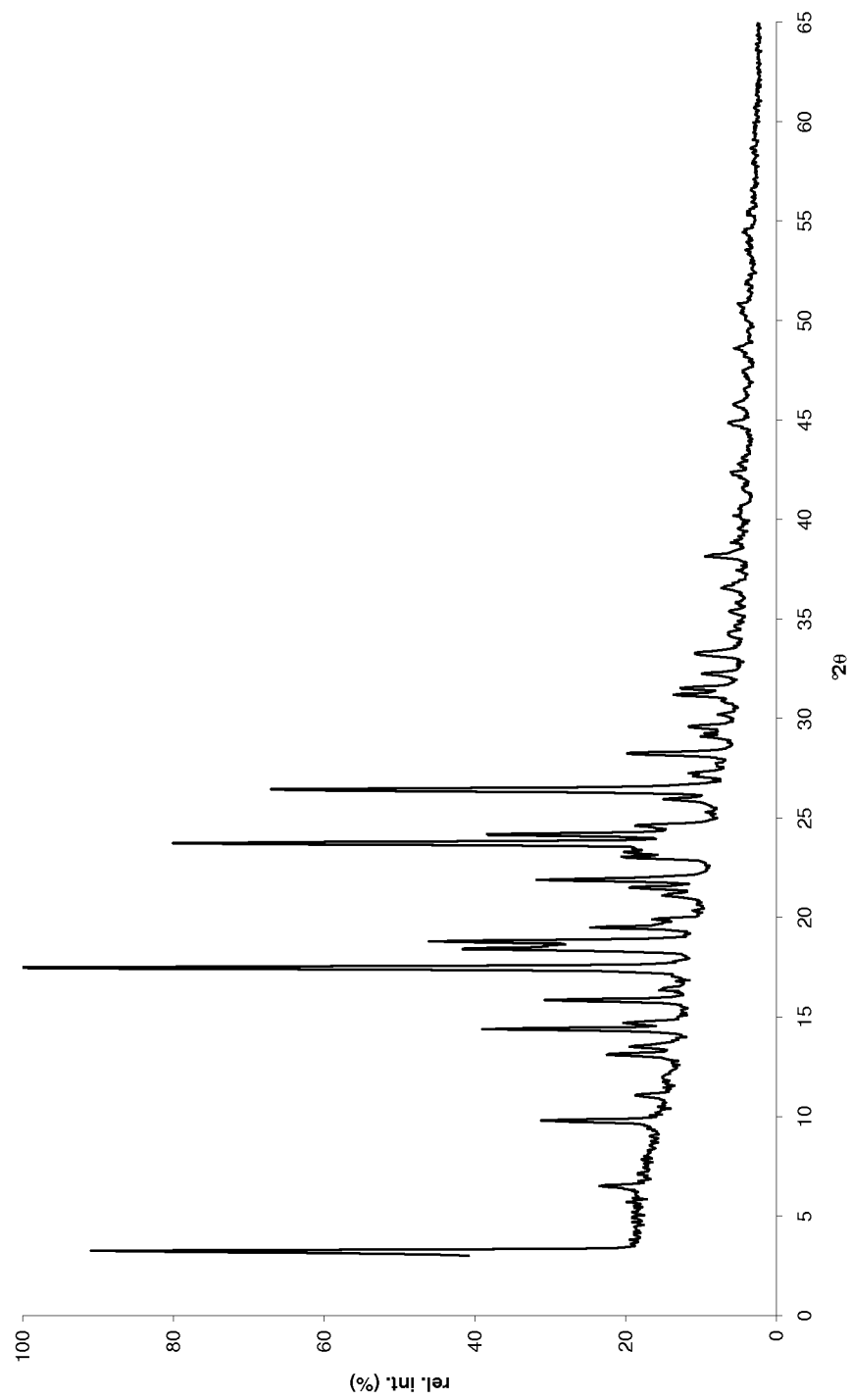
FIG. 1 depicts the powder X-ray diffractogram of crystalline modification A1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate.

Even without further details, it is assumed that a person skilled in the art will be able to utilise the above description in the broadest scope. The preferred embodiments should therefore merely be regarded as descriptive disclosure, which is absolutely not limiting in any way.

The contents of all cited references are hereby incorporated by reference in their entirety. The invention is explained in more detail by means of the following examples without, however, being restricted thereto.

EXAMPLES

Example 1

Production of 6-(1-methyl-1H-pyrazol-4-yl)-2-{3-[5-(2-morpholin-4-yl-ethoxy)-pyrimidin-2-yl]-benzyl}-2H-pyridazin-3-one Dihydrogenphosphate Anhydrate in its Crystalline Modification A1

Method 1

Approx. 118 mg of 6-(1-methyl-1H-pyrazol-4-yl)-2-{3-[5-(2-morpholin-4-yl-ethoxy)-pyrimidin-2-yl]-benzyl}-2H-pyridazin-3-one (free base) were dissolved in approx. 7 mL warm 2-propanol. After addition of approx. 0.017 mL aqueous phosphoric acid solution (85%), precipitation occurred. The dispersion was agitated for 2 hours at room temperature, and subsequently filtered. The resulting crystals were dried under vacuum at 70° C.

¹H-NMR (d₆-DMSO): δ [ppm]=2.50 (m, 4H+DMSO), 2.75 (t, 2H), 3.57 (t, 4H), 3.87 (s, 3H), 4.30 (t, 2H), 5.34 (s, 2H), 7.05 (d, 1H), 7.44 (m, 2H), 7.80 (d, 1H), 7.89 (s, 1H), 8.21 (m, 2H), 8.28 (m, 1H), 8.65 (s, 2H).

Ion Chromatography: 19.3 wt % Phosphate (equivalent to molar acid:base ratio of 1.14)

Method 2

Approx. 500 mg of 6-(1-methyl-1H-pyrazol-4-yl)-2-{3-[5-(2-morpholin-4-yl-ethoxy)-pyrimidin-2-yl]-benzyl}-2H-pyridazin-3-one (free base) were dissolved in approx. 10 mL chloroform. After addition of approx. 2.1 mL ethanolic phosphoric acid solution (0.5 mmol/L), the dispersion was agitated for 1 h at room temperature. The resulting precipitate was filtered and the harvested crystals were dried under vacuum at 70° C.

¹H-NMR (d₆-DMSO): δ [ppm]=2.55 (m, 4H), 2.80 (t, 2H), 3.60 (m, 4H), 3.88 (s, 3H), 4.33 (t, 2H), 5.35 (s, 2H), 7.07 (d, 1H), 7.46 (m, 2H), 7.82 (d, 1H), 7.90 (s, 1H), 8.23 (m, 2H), 8.30 (m, 1H), 8.65 (s, 2H).

Ion Chromatography: 14.9 wt % Phosphate (equivalent to molar acid:base ratio of 0.88)

Method 3

Approx. 354 g of 6-(1-methyl-1H-pyrazol-4-yl)-2-{3-[5-(2-morpholin-4-yl-ethoxy)-pyrimidin-2-yl]-benzyl}-2H-pyridazin-3-one (free base) were dispersed in approx. 450 mL DI water at 23° C. After addition of approx. 57.3 mL aqueous phosphoric acid solution (85%), the dispersion was heated to 50° C., resulting in a clear solution. The solution was cooled down to 20° C., and diluted with approx. 1.2 L acetone, resulting in crystallisation. The dispersion was agitated at 10° C. until the crystallisation was completed. The dispersion was left at room temperature for several days and subsequently cooled down to 5° C. and filtered. The resulting crystals were washed with acetone and dried under vacuum at 70° C. The dried crystals were subsequently boiled in ethanol as dispersion for 30 minutes, and filtrated from the hot dispersion.

¹H-NMR (d₆-DMSO): δ [ppm]=2.50 (m, 4H+DMSO), 2.74 (t, 2H), 3.58 (m, 4H), 3.87 (s, 3H), 4.32 (t, 2H), 5.34 (s, 2H), 7.05 (d, 1H), 7.45 (m, 2H), 7.82 (d, 1H), 7.89 (s, 1H), 8.22 (m, 2H), 8.28 (m, 1H), 8.65 (s, 2H).

Ion Chromatography: 19.5 wt % Phosphate (equivalent to molar acid:base ratio of 1.15)

Method 4

Approx. 1.1 kg of 6-(1-methyl-1H-pyrazol-4-yl)-2-{3-[5-(2-morpholin-4-yl-ethoxy)-pyrimidin-2-yl]-benzyl}-2H-pyridazin-3-one (free base) were dispersed in approx. 1.37 L DI water at 23° C. After addition of approx. 240 mL aqueous phosphoric acid solution (85%), the dispersion was heated to 50° C., resulting in a clear solution. The solution was cooled down to 20° C., and slowly diluted with approx. 1 L acetone under agitation, resulting in beginning crystallisation. Another approx. 3 L acetone were slowly added, resulting in a white dispersion, which was agitated at room temperature over night. The dispersion was filtered, and resulting crystals were washed with Acetone and dried under vacuum at 70° C.

¹H-NMR (d₆-DMSO): δ [ppm]=2.50 (m, 4H+DMSO), 2.74 (t, 2H), 3.57 (m, 4H), 3.87 (s, 3H), 4.30 (t, 2H), 5.34 (s, 2H), 7.05 (d, 1H), 7.45 (m, 2H), 7.82 (d, 1H), 7.89 (s, 1H), 8.22 (m, 2H), 8.28 (m, 1H), 8.64 (s, 2H).

Ion Chromatography: 16.8 wt % Phosphate (equivalent to molar acid:base ratio of 0.99)

Method 5

Approx. 100 g of 6-(1-methyl-1H-pyrazol-4-yl)-2-{3-[5-(2-morpholin-4-yl-ethoxy)-pyrimidin-2-yl]-benzyl}-2H-pyridazin-3-one (free base) were dispersed in approx. 171.4 g DI water at 23° C. After addition of approx. 36.55 g aqueous phosphoric acid solution (85%), the solution was filtered. The resulting filtrate was diluted with approx. 331.05 g acetone, resulting in a dispersion. The dispersion was heated to 55° C., resulting in a clear solution. The solution was cooled down to −10° C. with a defined cooling rate of 0.3 K/min, resulting in a dispersion, which was post-slurried at −10° C. for one hour. The dispersion was filtered, and resulting crystals were washed with acetone and dried under vacuum at 70° C.

¹H NMR (500 MHz, DMSO) δ=8.64 (s, 2H), 8.31-8.26 (m, 1H), 8.25-8.19 (m, 2H), 7.89 (s, 1H), 7.81 (d, J=9.6, 1H), 7.53-7.38 (m, 2H), 7.05 (d, J=9.6, 1H), 5.33 (s, 2H), 4.31 (t, J=5.6, 2H), 3.87 (s, 3H), 3.65-3.52 (m, 4H), 2.75 (t, J=5.6, 2H), 2.50 (m, 4H)

Ion Chromatography: 17.7 wt % Phosphate (equivalent to molar acid:base ratio of 1.04)

Method 6

Approx. 15.2 kg of 6-(1-methyl-1H-pyrazol-4-yl)-2-{3-[5-(2-morpholin-4-yl-ethoxy)-pyrimidin-2-yl]-benzyl}-2H-pyridazin-3-one (free base) were dispersed in approx. 31 kg DI water at T<30° C. After addition of approx. 5.5 kg aqueous phosphoric acid solution (85%), the solution was slurried for 30 minutes, and subsequently filtered. The resulting filtrate was diluted at 25° C. with approx. 55.8 kg acetone, resulting in a dispersion. The dispersion was heated to 62° C., resulting in a clear solution. The solution was cooled down to 50° C. (thermostat jacket temperature) with a defined cooling rate of 0.1 K/min, and slurried for approx. 6.5 hours, until a turbid dispersion was resulting. The dispersion was further cooled down to −10° C. (thermostat jacket temperature) with a defined cooling rate of 0.1 K/min, and post-slurried for approx. 1 hour at this temperature. The dispersion was filtered, and resulting crystals were washed with acetone and dried under vacuum at 70° C.

¹H NMR (500 MHz, DMSO) δ=8.65 (s, 2H), 8.35-8.26 (m, 1H), 8.25-8.19 (m, 2H), 7.89 (s, 1H), 7.81 (d, J=9.6, 1H), 7.53-7.38 (m, 2H), 7.06 (d, J=9.6, 1H), 5.34 (s, 2H), 4.33 (t, J=5.5, 2H), 3.87 (s, 3H), 3.69-3.52 (m, 4H), 2.82 (t, J=5.4, 2H), 2.64-2.53 (m, 4H).

Ion Chromatography: 17.1 wt % Phosphate (equivalent to molar acid:base ratio of 1.01)

Example 2

Production of 6-(1-methyl-1H-pyrazol-4-yl)-2-{3-[5-(2-morpholin-4-yl-ethoxy)-pyrimidin-2-yl]-benzyl}-2H-pyridazin-3-one Dihydrogenphosphate Dihydrate in its Crystalline Modification H1

Method 1

Approx. 400 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate in its crystalline modification A1 were spread onto a Petri dish and stored in a closed desiccator over pure DI water (100% relative humidity atmosphere) for 2 weeks.

¹H-NMR (d₆-DMSO): δ [ppm]=2.50 (m, 4H+DMSO), 2.74 (t, 2H), 3.57 (m, 4H), 3.87 (s, 3H), 4.30 (t, 2H), 5.34 (s, 2H), 7.05 (d, 1H), 7.45 (m, 2H), 7.82 (d, 1H), 7.89 (s, 1H), 8.22 (m, 2H), 8.29 (m, 1H), 8.65 (s, 2H).

Ion Chromatography: 17.1 wt % Phosphate (equivalent to molar acid:base ratio of 1.08 based on phosphate salt with observed water content as specified below).

Karl-Fischer-Titration: 6.5 wt % water.

Method 2

Approx. 45 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate in its crystalline modification A1 were dispersed in approx. 0.2 mL of a binary mixture DI water/ethanol (1:1, v/v), and shaken as slurry at 50° C. at 1000 rpm for 7 days. The dispersion was then filtered and resulting crystals were dried at ambient conditions on the filter.

Method 3

Approx. 45 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate in its crystalline modification A1 were dispersed in approx. 0.2 mL of a binary mixture DI water/methanol (1:1, v/v), and shaken as slurry at 50° C. at 1000 rpm for 7 days. The dispersion was then filtered and resulting crystals were dried at ambient conditions on the filter.

Method 4

Approx. 50 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate in its crystalline modification A1 were dispersed in approx. 0.2 mL of a binary mixture DI water/2-propanol (1:1, v/v), and shaken as slurry at 50° C. at 1000 rpm for 7 days. The dispersion was then filtered and resulting crystals were dried at ambient conditions on the filter.

Method 5

Approx. 30 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate in its crystalline modification A1 were dispersed in approx. 0.2 mL of a binary mixture DI water/acetone (1:1, v/v), and shaken as slurry at 50° C. at 1000 rpm for 7 days. The dispersion was then filtered and resulting crystals were dried at ambient conditions on the filter.

Method 6

Approx. 65 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate in its crystalline modification A1 were dispersed in approx. 0.2 mL of a binary mixture DI water/THF (1:1, v/v), and shaken as slurry at 50° C. at 1000 rpm for 7 days. The dispersion was then filtered and resulting crystals were dried at ambient conditions on the filter.

Method 7

Approx. 50 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate in its crystalline modification A1 were dispersed in approx. 0.15 mL of a binary mixture DI water/acetonitrile (1:1, v/v), and shaken as slurry at 50° C. at 1000 rpm for 7 days. The dispersion was then filtered and resulting crystals were dried at ambient conditions on the filter.

Example 3

Production of 6-(1-methyl-1H-pyrazol-4-yl)-2-{3-[5-(2-morpholin-4-yl-ethoxy)-pyrimidin-2-yl]-benzyl}-2H-pyridazin-3-one Dihydrogenphosphate in its Crystalline Modification NF3

Method 1

Approx. 30 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate in its crystalline modification A1 were dissolved in approx. 3 ml of a binary mixture DI water/ethanol (1:1, v/v). Crystallization occurred on evaporation of the solvent at ambient conditions. The crystals were isolated by filtration and dried at ambient conditions on the filter.

Method 2

Approx. 155 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate in its crystalline modification A1 were dissolved in approx. 15 ml of a binary mixture DI water/1,4-dioxane (1:1, v/v). Crystallization occurred on evaporation of the solvent at 50° C. The crystals were isolated by filtration and dried at ambient conditions on the filter.

$^1$H NMR (500 MHz, DMSO) d=8.63 (s, 2H), 8.31-8.26 (m, 1H), 8.25-8.18 (m, 2H), 7.89 (s, 1H), 7.80 (d, J=9.6, 1H), 7.55-7.40 (m, 2H), 7.05 (d, J=9.6, 1H), 5.34 (s, 2H), 4.31 (t, J=5.6, 2H), 3.87 (s, 3H), 3.80-3.30 (m, 4H) 2.74 (t, J=5.5, 2H), 2.50 (m, 4H)

Ion Chromatography: 16.0 wt % Phosphate (equivalent to molar acid:base ratio of 0.94).

Example 4

Production of 6-(1-methyl-1H-pyrazol-4-yl)-2-{3-[5-(2-morpholin-4-yl-ethoxy)-pyrimidin-2-yl]-benzyl}-2H-pyridazin-3-one Dihydrogenphosphate Hydrate in its Crystalline Modification NF5

Method 1

Approx. 100 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate in its crystalline modification A1 were dissolved in approx. 1 ml of a binary mixture DI water/methanol (1:1, v:v). The solution was heated to 60° C., and simultaneously evacuated for fast solvent evaporation. The resulting precipitate was spread as a powder onto a Petri dish, and subsequently incubated in a sealed desiccator over saturated salt solution of $KNO_3$ (94% RH) for several days.

$^1$H NMR (500 MHz, DMSO) d=8.64 (s, 2H), 8.31-8.25 (m, 1H), 8.25-8.19 (m, 2H), 7.88 (s, 1H), 7.80 (d, J=9.6, 1H), 7.52-7.38 (m, 2H), 7.04 (d, J=9.6, 1H), 5.33 (s, 2H), 4.30 (t, J=5.6, 2H), 3.87 (s, 3H), 3.66-3.50 (m, 4H), 2.73 (t, J=5.6, 2H), 2.50 (m, 4H)

Ion Chromatography: 14.8 wt % Phosphate (equivalent to molar acid:base ratio of 0.94 based on phosphate salt with observed water content as specified below).

Karl-Fischer-Titration: 7.3 wt % water.

Method 2:

Approx. 100 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate in its crystalline modification NF3 were spread as a powder onto a Petri dish, and subsequently incubated in a sealed desiccator over saturated salt solution of $KNO_3$ (94% RH) for several days.

Example 5

Structural and Physico-Chemical Characterization of 6-(1-methyl-1H-pyrazol-4-yl)-2-{3-[5-(2-morpholin-4-yl-ethoxy)-pyrimidin-2-yl]-benzyl}-2H-pyridazin-3-one Dihydrogenphosphate Anhydrate in its Crystalline Modification A1

A Powder X-Ray Diffraction (XRD) pattern of crystalline modification A1 was obtained by standard techniques as described in European Pharmacopeia, 6$^{th}$ Edition, chapter 2.9.33. Crystalline modification A1 is characterized by the X-ray powder diffractogram (Cu-K$\alpha_1$ radiation, $\lambda$=1.5406 Å, Stoe StadiP 611 KL diffractometer.) depicted in FIG. 1.

Crystalline modification A1 is characterized by the following XRD data:
Powder X-Ray Diffractogram Peak List:

| Peak No. | d/Å | °2θ (Cu—Kα$_1$ radiation) ± 0.1° | Indexing (h, k, l) |
|---|---|---|---|
| 1 | 27.45 | 3.2 | (2, 0, 0) |
| 2 | 13.62 | 6.5 | (4, 0, 0) |
| 3 | 9.02 | 9.8 | (6, 0, 0) |
| 4 | 6.75 | 13.1 | (8, 0, 0) |
| 5 | 6.15 | 14.4 | (−2, 0, 2) |
| 6 | 5.59 | 15.8 | (−6, 0, 2) |
| 7 | 5.07 | 17.5 | (−8, 0, 2) |
| 8 | 4.81 | 18.4 | (9, 1, 0) |
| 9 | 4.72 | 18.8 | (−9, 1, 1) |
| 10 | 4.55 | 19.5 | (6, 0, 2) |
| 11 | 4.06 | 21.9 | (8, 0, 2) |
| 12 | 3.75 | 23.7 | (11, 1, 1) |
| 13 | 3.68 | 24.2 | (2, 2, 1) |
| 14 | 3.37 | 26.4 | (3, 1 3) |
| 15 | 3.16 | 28.2 | (−15, 1, 2) |

Figure 2:
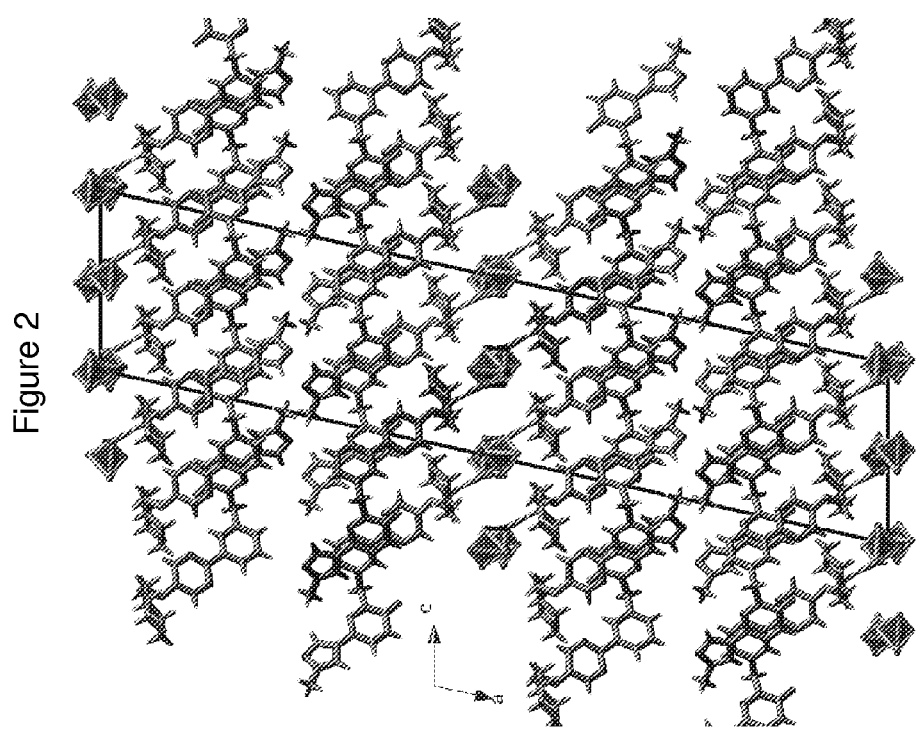
FIG. 2 depicts single crystal X-Ray Structure data of crystalline modification A1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate viewed along b-axis.

Single crystal X-Ray Structure data were obtained on crystalline modification A1 as well (XCalibur diffractometer from Oxford Diffraction equipped with graphite monochromator and CCD Detector using Mo K$_\alpha$ radiation at 301 K). The single crystal structure of crystalline modification A1 viewed along b-axis is depicted in FIG. 2.

Crystalline modification A1 crystallizes in the monoclinic space group C2/c with the lattice parameters a=55.1 Å, b=7.9 Å, c=12.2 Å, and β=102.2° (with α=γ=90°). From the single crystal structure it is obvious that crystalline modification A1 represents an anhydrous form.

Crystalline modification A1 was further characterized by IR- and Raman-spectroscopy. FT-Raman and FT-IR spectra were obtained by standard techniques as described in the European Pharmacopeia, 6$^{th}$ Edition, chapter 2.02.24 and 2.02.48. For measurement of the FT-IR and FT-Raman-spectra a Bruker Vector 22 and a Bruker RFS 100 spectrometer were used. FT-IR spectra were base-line corrected using Bruker OPUS software. FT-Raman spectra were vector normalized using the same software.

Figure 3:
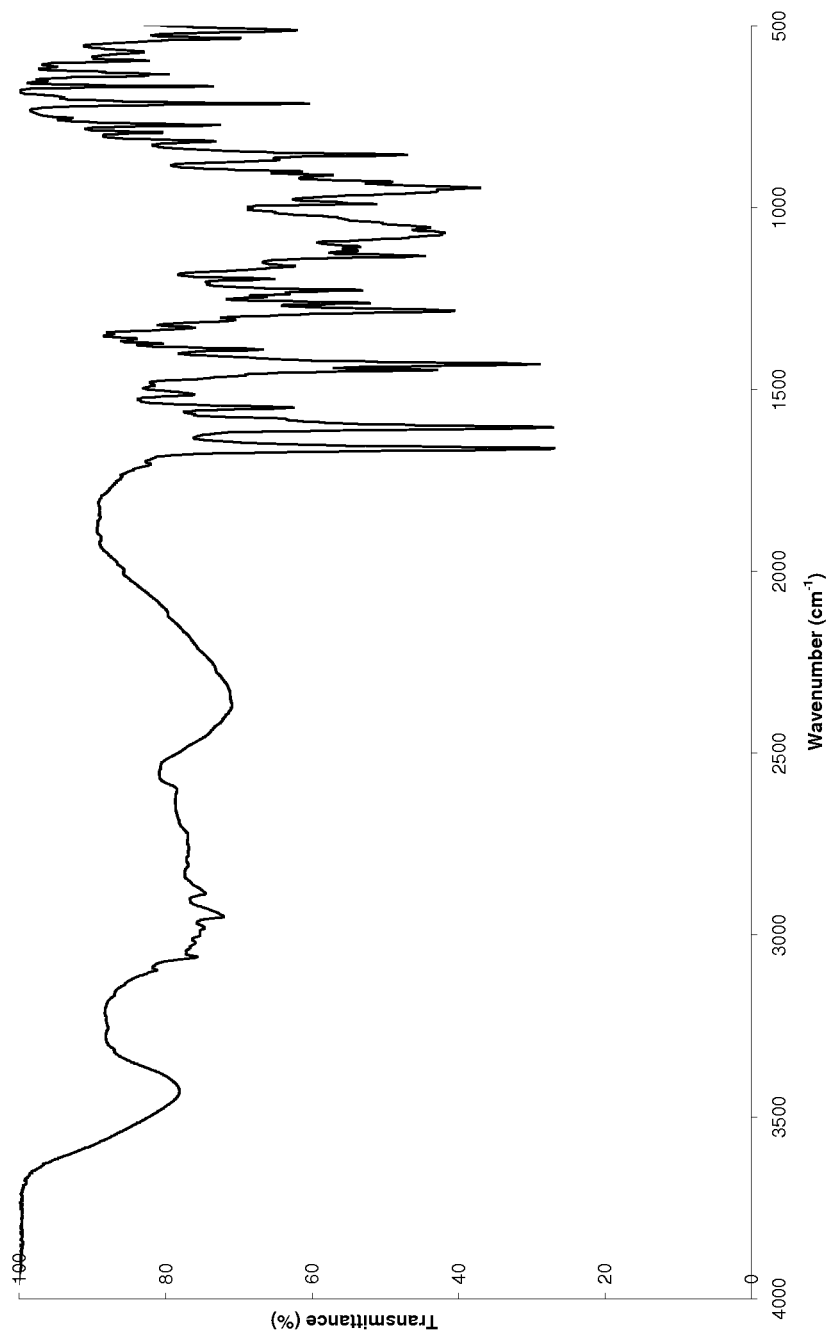
FIG. 3 depicts the FT-IR spectrum of crystalline modification A1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate.

An FT-IR spectrum was obtained using a KBr pellet as sample preparation technique. The FT-IR spectrum is depicted in FIG. 3 and the band positions are given below.

Crystalline modification A1 IR band positions ±2 cm$^{-1}$ (relative intensity*) 2949 cm$^{-1}$ (w), 2885 cm$^{-1}$ (w), 2368 cm$^{-1}$ (w, broad), 1661 cm$^{-1}$ (s), 1603 cm$^{-1}$ (s), 1549 cm$^{-1}$ (m), 1446 cm$^{-1}$ (s), 1429 cm$^{-1}$ (s), 1283 cm$^{-1}$ (s), 1261 cm$^{-1}$ (m), 1226 cm$^{-1}$ (m), 1132 cm$^{-1}$ (s), 1068 cm$^{-1}$ (s), 945 cm$^{-1}$ (s), 854 cm$^{-1}$ (s), 713 cm$^{-1}$ (m)

*"s"=strong (transmittance≤50%), "m"=medium (50%<transmittance≤70%), "w"=weak (transmittance>70%)

Figure 4:
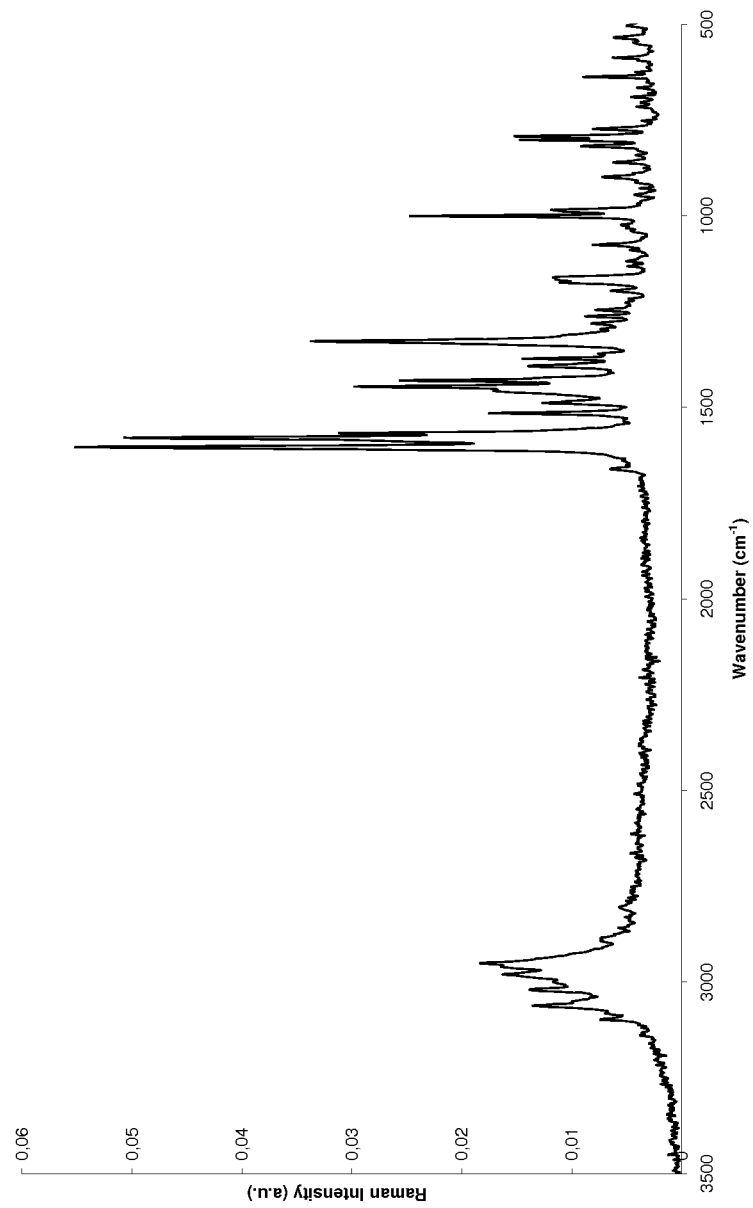
FIG. 4 depicts the FT-Raman spectrum of crystalline modification A1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate.

An FT-Raman spectrum is depicted in FIG. 4 and the band positions are given below.

Crystalline modification A1 Raman band positions ±2 cm$^{-1}$ (relative intensity*): 3061 cm$^{-1}$ (w), 2951 cm$^{-1}$ (w), 1604 cm$^{-1}$ (s), 1579 cm$^{-1}$ (s), 1568 cm$^{-1}$ (m), 1515 cm$^{-1}$ (w), 1446 cm$^{-1}$ (m), 1430 cm$^{-1}$ (m), 1327 cm$^{-1}$ (m), 1161 cm$^{-1}$ (w), 1001 cm$^{-1}$ (m), 802 cm$^{-1}$ (w), 793 cm$^{-1}$ (w)

*"s"=strong (relative Raman intensity≥0.04), "m"=medium (0.04>relative Raman intensity≥0.02), "w"=weak (relative Raman intensity<0.02)

Figure 5:
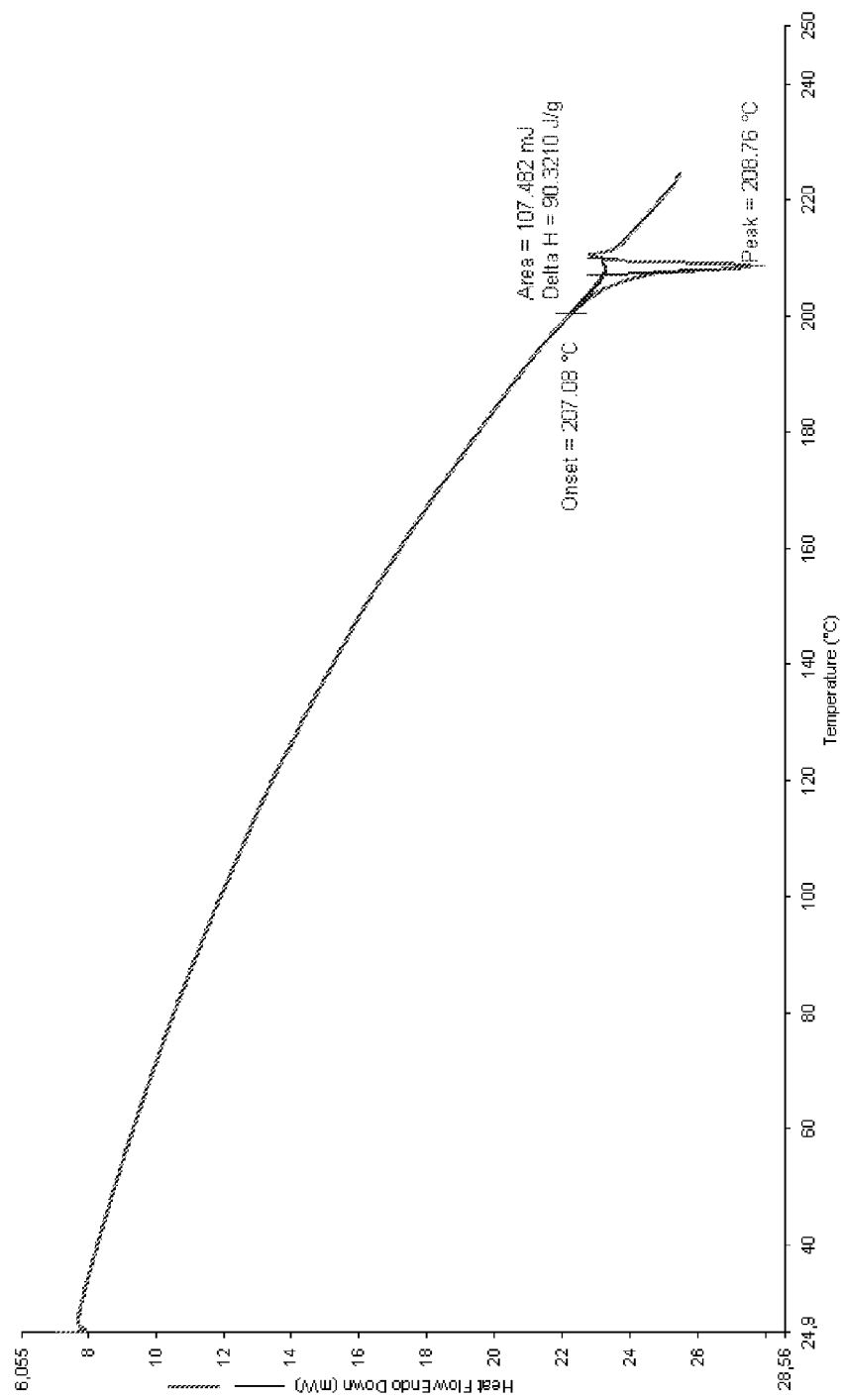
FIG. 5 depicts the DSC scan profile (Perkin-Elmer Diamond DSC, 5 K/min, nitrogen purge gas 50 mL/min) of crystalline modification A1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate.
Figure 6:
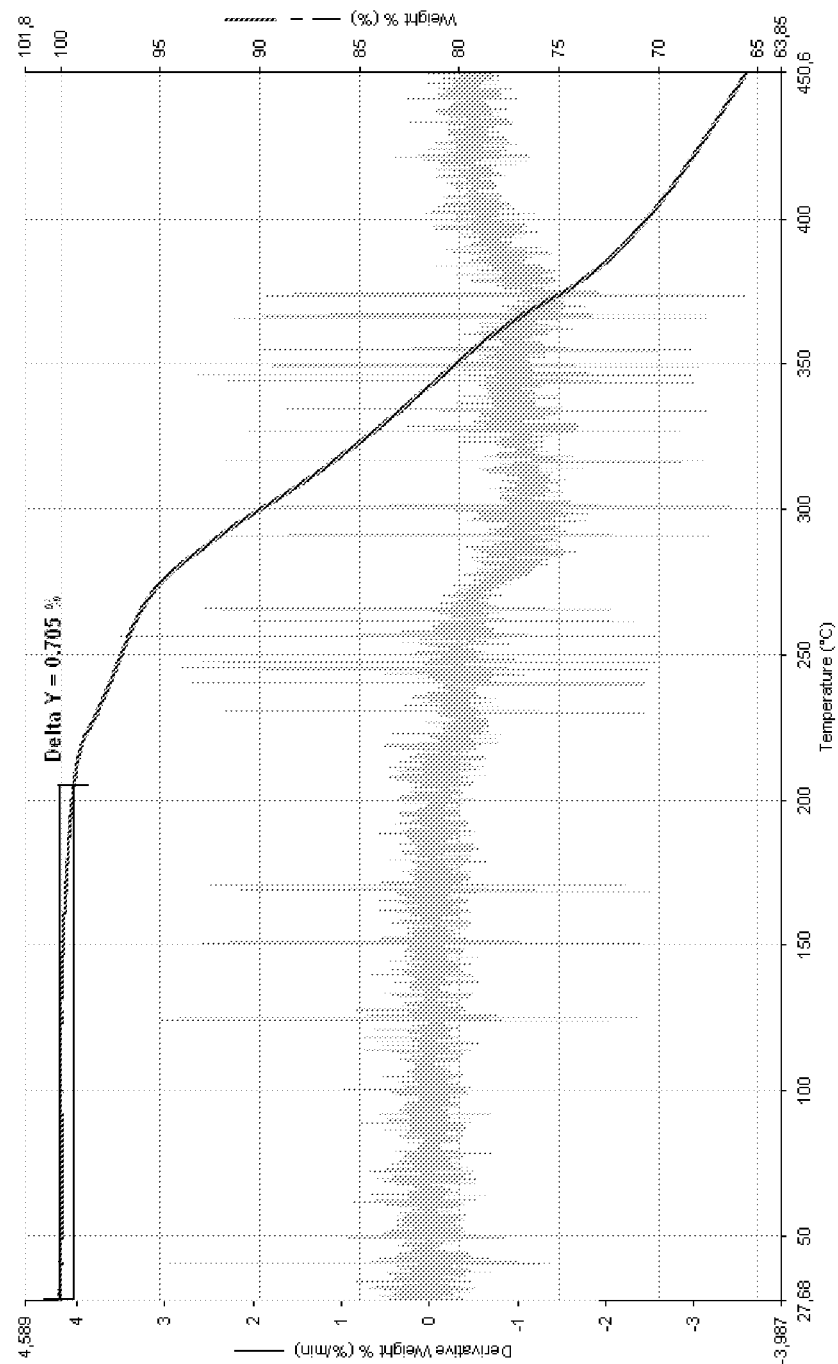
FIG. 6 depicts the TGA scan profile (Perkin-Elmer Pyris TGA1, 5 K/min, nitrogen purge gas 50 mL/min) of crystalline modification A1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate.

Crystalline modification A1 is a crystalline anhydrous form, which is further characterized by the following physical properties:

Thermal behavior shows a melting peak at approx. 207° C., with a very small mass loss up to the melting temperature. DSC profile (Perkin-Elmer Diamond DSC, 5 K/min, nitrogen purge gas 50 mL/min) and TGA profile (Perkin-Elmer Pyris TGA1, 5 K/min, nitrogen purge gas 50 mL/min) are displayed in FIGS. 5 and 6, respectively.

Figure 7:
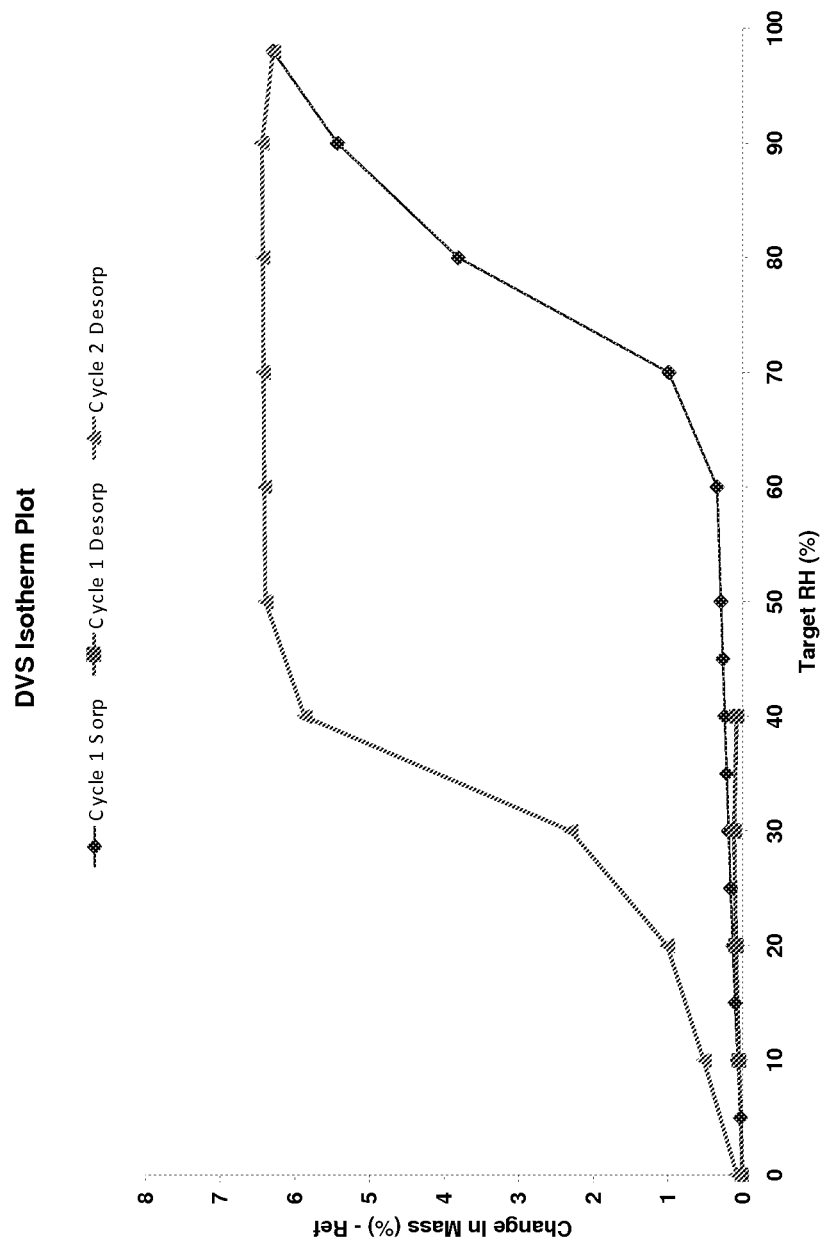
FIG. 7 depicts the Water Vapour Sorption Isotherm (25° C.) (SMS DVS 1) of crystalline modification A1, type a, of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate.
Figure 8:
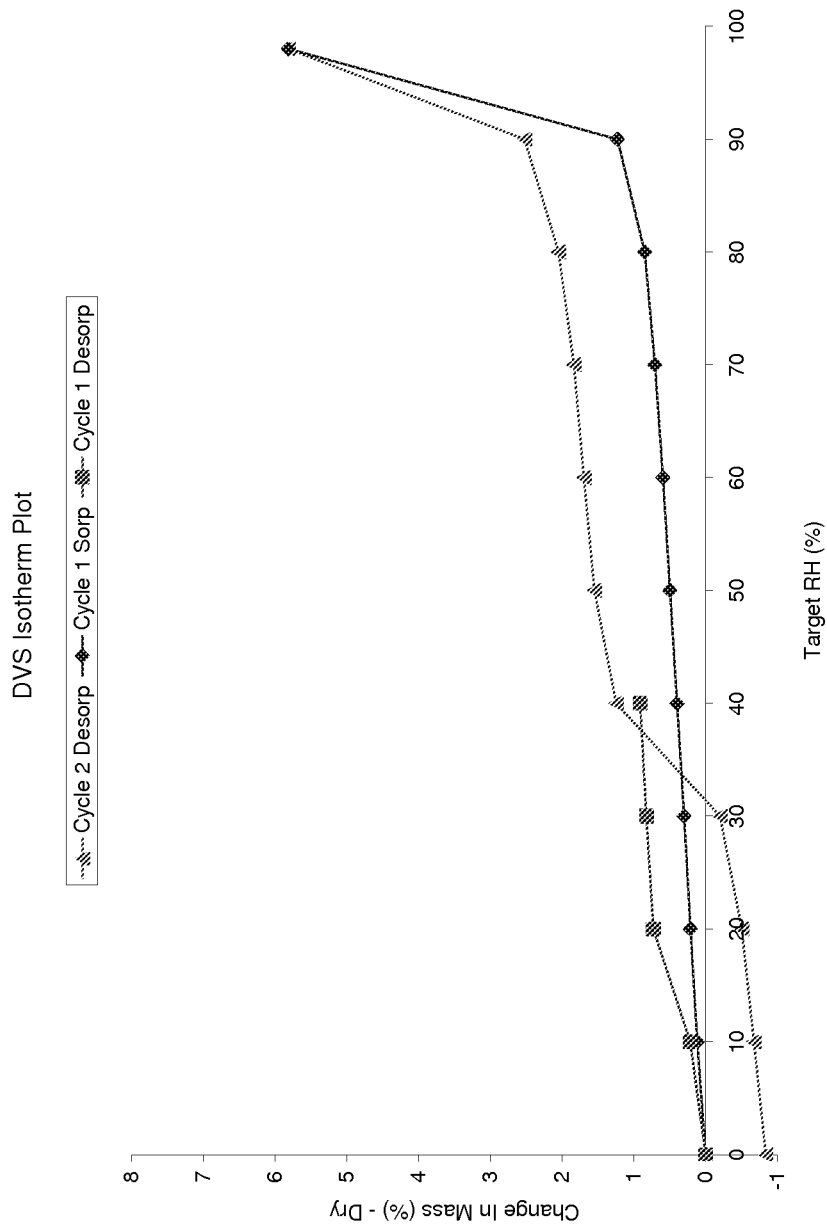
FIG. 8 depicts the Water Vapour Sorption Isotherm (25° C.) (SMS DVS 1) of crystalline modification A1, type b, of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate.

Water Vapor Sorption behavior shows small water uptake levels upon adsorption in the range 0-70% relative humidity (RH) (crystalline modification A, type a) and 0-90% RH (crystalline modification A, type b), respectively. Pronounced water uptake levels are observed above 70% RH (crystalline modification A type a) and above 90% RH (crystalline modification A type b), respectively, which results in formation of dihydrate crystalline modification H1 (water uptake levels of approx. 6 wt %) at elevated relative humidity (RH). Water Vapor Sorption isotherms [Water Vapour Sorption Isotherm (25° C.) (SMS DVS 1)] of crystalline modification A1 (types a and b) are displayed in FIGS. 7 and 8, respectively.

Example 6

Structural and Physico-Chemical Characterization of 6-(1-methyl-1H-pyrazol-4-yl)-2-{3-[5-(2-morpholin-4-yl-ethoxy)-pyrimidin-2-yl]-benzyl}-2H-pyridazin-3-one Dihydrogenphosphate Dihydrate in its Crystalline Modification H1

Figure 9:
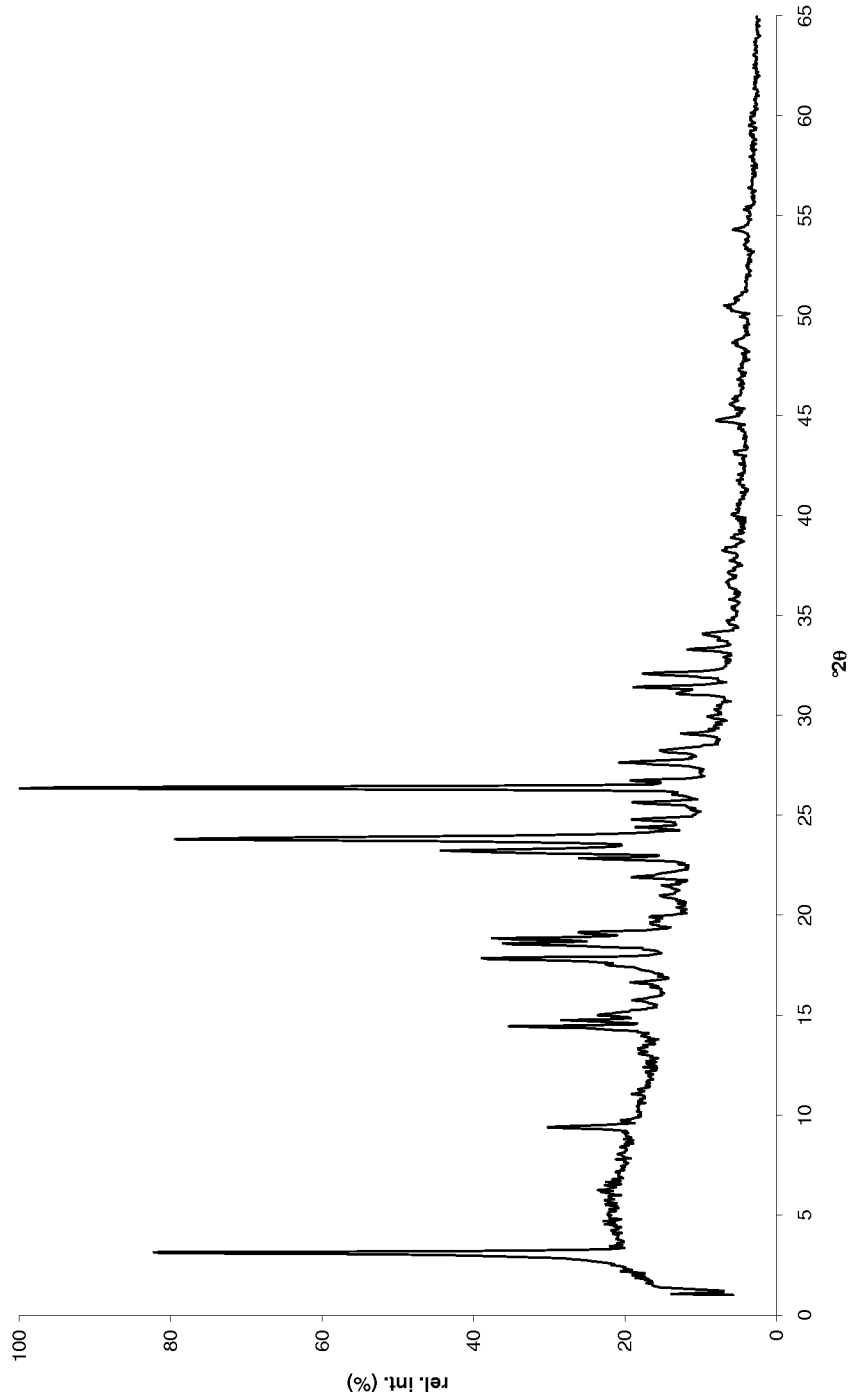
FIG. 9 depicts the powder X-ray diffractogram of crystalline modification H1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate.

A Powder X-Ray Diffraction (XRD) pattern of crystalline modification H1 was obtained by standard techniques as described in European Pharmacopeia, 6$^{th}$ Edition, chapter 2.9.33. Crystalline modification H1 is characterized by the X-ray powder diffractogram (Cu-Kα$_1$ radiation, λ=1.5406 Å, Stoe StadiP 611 KL diffractometer.) depicted in FIG. 9.

Crystalline modification H1 is characterized by the following XRD data:
Powder X-Ray Diffractogram Peak List:

| Peak No. | d/Å | °2θ (Cu—Kα$_1$ radiation) ± 0.1° | Indexing (h, k, l) |
|---|---|---|---|
| 1 | 28.42 | 3.1 | (1, 0, 0) |
| 2 | 9.40 | 9.4 | (3, 0, 0) |
| 3 | 6.13 | 14.4 | (0, 0, 2) |
| 4 | 6.01 | 14.7 | (2, 1, 1) |
| 5 | 5.89 | 15.0 | (1, 0, 2) |
| 6 | 4.97 | 17.8 | (3, 0, 2) |
| 7 | 4.77 | 18.6 | (4, 1, 1) |
| 8 | 4.71 | 18.8 | (6, 0, 0) |
| 9 | 4.64 | 19.1 | (5, 1, 0) |
| 10 | 3.89 | 22.8 | (2, 2, 0) |
| 11 | 3.83 | 23.2 | (−1, 2, 1) |
| 12 | 3.73 | 23.8 | (−2, 2, 1) |
| 13 | 3.38 | 26.4 | (0, 2, 2) |
| 14 | 3.33 | 26.8 | (−4, 1, 3) |
| 15 | 3.22 | 27.6 | (−3, 2, 2) |

Figure 10:
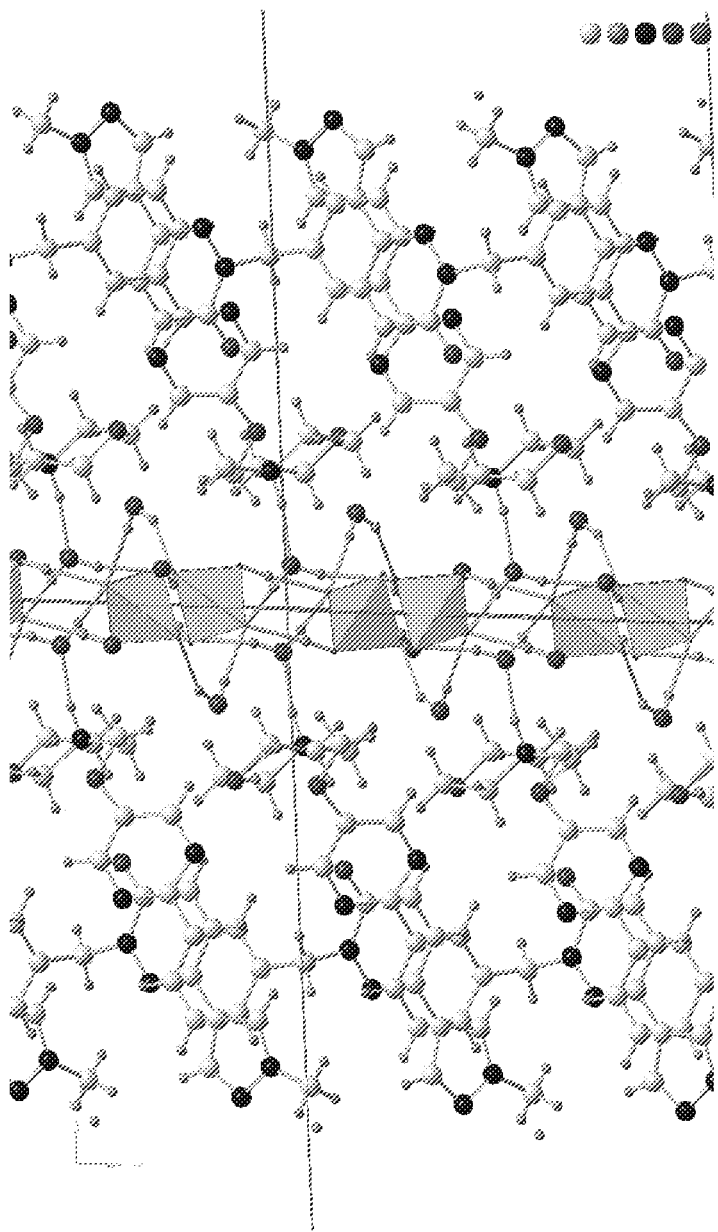
FIG. 10 depicts single crystal X-Ray Structure data of crystalline modification H1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate.

Single crystal X-Ray Structure data were obtained on crystalline modification H1 as well (XCalibur diffractometer from Oxford Diffraction equipped with graphite monochromator and CCD Detector using Mo K, radiation at 301 K). The single crystal structure of crystalline modification H1 is depicted in FIG. 10.

Crystalline modification H1 crystallizes in the monoclinic space group P2$_1$/C with the lattice parameters a=28.2 Å, b=8.1 Å, c=12.3 Å, and β=94.1° (with α=γ=90°). From the single crystal structure it is obvious that crystalline modification H1 represents a stoichiometric dihydrate.

Crystalline modification H1 was further characterized by IR-spectroscopy. FT-IR spectra were obtained by standard techniques as described in the European Pharmacopeia, 6$^{th}$ Edition, chapter 2.02.24 and 2.02.48. For measurement of the FT-IR spectra a Bruker Vector 22 spectrometer was used. FT-IR spectra were base-line corrected using Bruker OPUS software.

Figure 11:
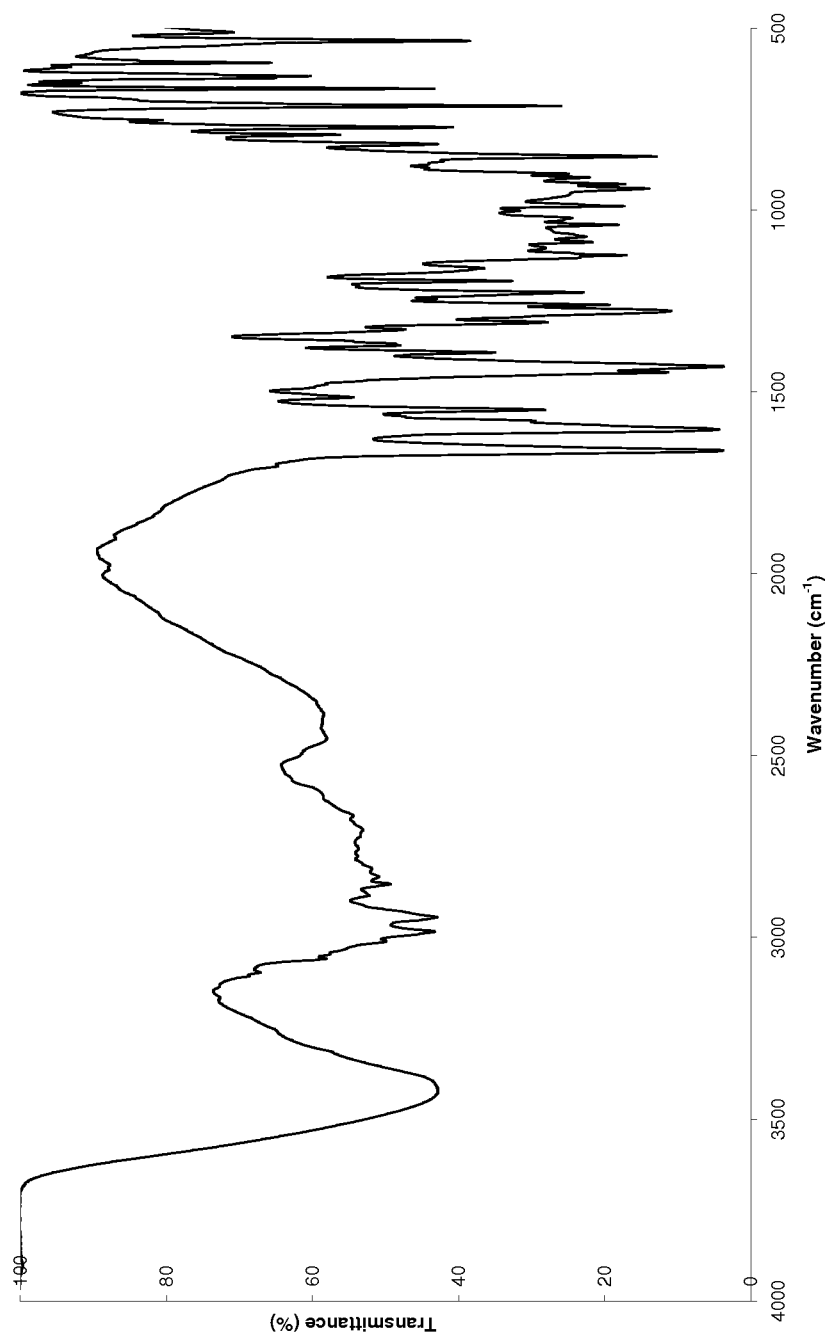
FIG. 11 depicts the FT-IR spectrum of crystalline modification H1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate.

An FT-IR spectrum was obtained using a KBr pellet as sample preparation technique. The FT-IR spectrum is depicted in FIG. 11 and the band positions are given below.

Crystalline modification H1 IR band positions ±2 cm$^{-1}$ (relative intensity*) 2984 cm$^{-1}$ (s), 2944 cm$^{-1}$ (s), 2451 cm$^{-1}$ (m, broad), 1661 cm$^{-1}$ (s), 1603 cm$^{-1}$ (s), 1548 cm$^{-1}$ (s), 1446 cm$^{-1}$ (s), 1430 cm$^{-1}$ (s), 1277 cm$^{-1}$ (s), 1260 cm$^{-1}$ (s), 1226 cm$^{-1}$ (s), 1124 cm$^{-1}$ (s), 1040 cm$^{-1}$ (s), 940 cm$^{-1}$ (s), 852 cm$^{-1}$ (s), 713 cm$^{-1}$ (s)

*"s"=strong (transmittance≤50%), "m"=medium (50%<transmittance≤70%), "w"=weak (transmittance>70%)

FT-Raman spectroscopy of crystalline modification H1 shows an identical spectrum to crystalline modification A1, since dehydration of hydrate water occurs as a consequence of the laser excitation.

Figure 12:
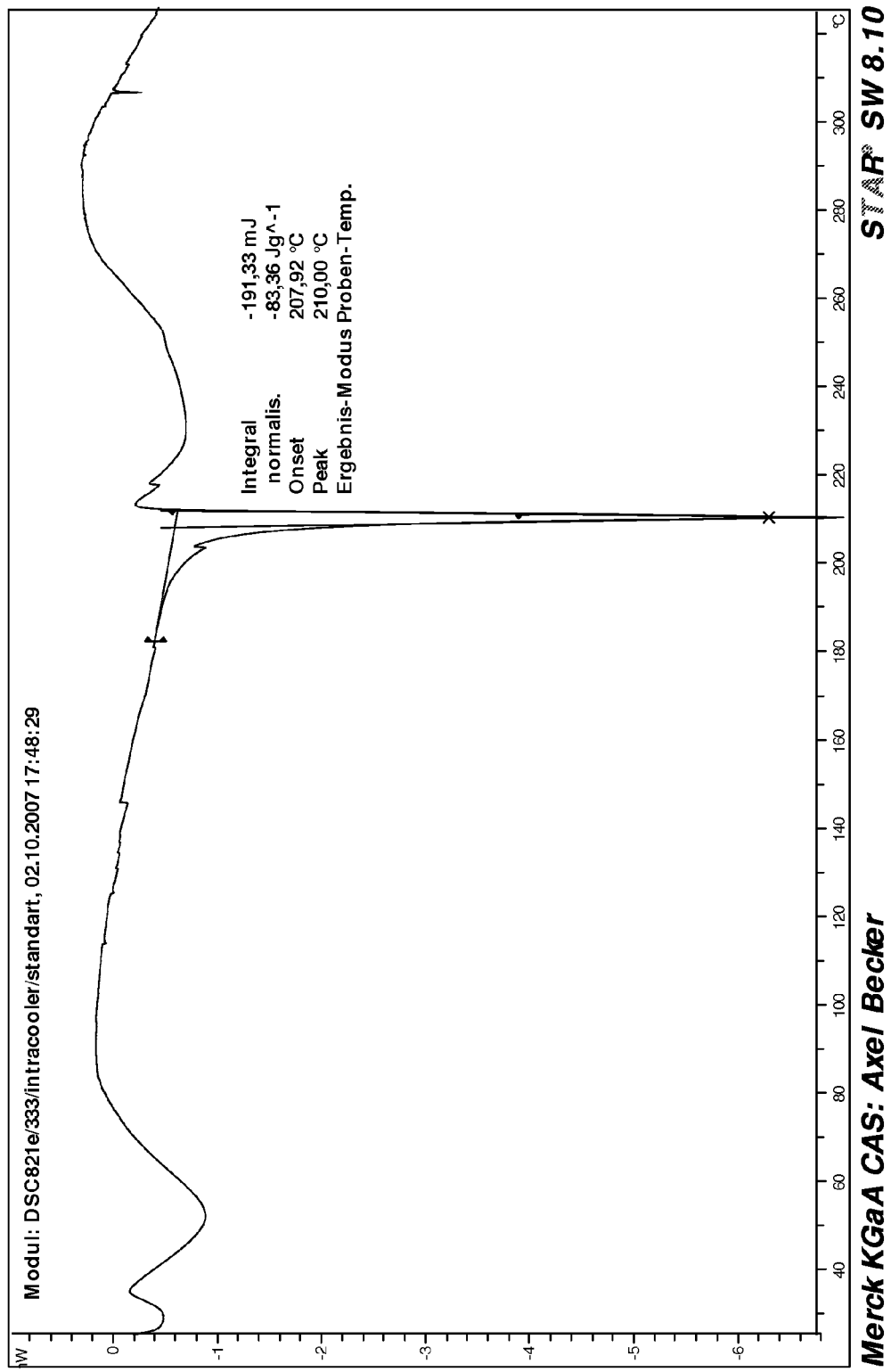
FIG. 12 depicts the DSC scan profile (Perkin-Elmer Diamond DSC, 5 K/min, nitrogen purge gas 50 mL/min) of crystalline modification H1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate.
Figure 13:
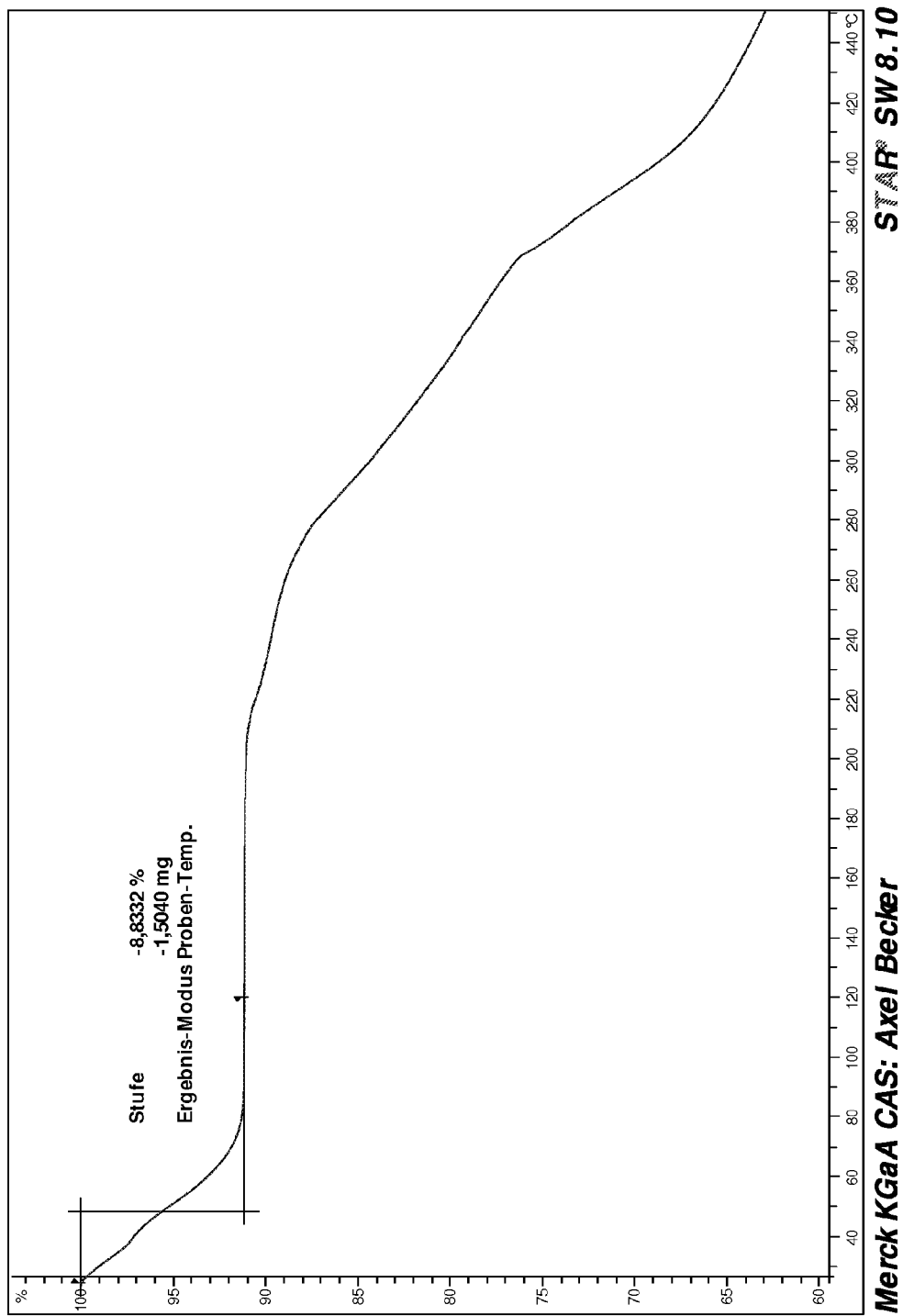
FIG. 13 depicts the TGA scan profile (Perkin-Elmer Pyris TGA1, 5 K/min, nitrogen purge gas 50 mL/min) of crystalline modification H1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate.

Crystalline modification H1 is a crystalline dihydrate form, which is further characterized by the following physical properties:

Thermal behavior shows dehydration of hydrate water from approx. 30-120° C. upon heating, with subsequent melting of the anhydrous form at approx. 208° C. DSC profile (Perkin-Elmer Diamond DSC, 5 K/min, nitrogen purge gas 50 mL/min) and TGA profile (Perkin-Elmer Pyris TGA1, 5 K/min, nitrogen purge gas 50 mL/min) are displayed in FIGS. 12 and 13, respectively.

Figure 14:
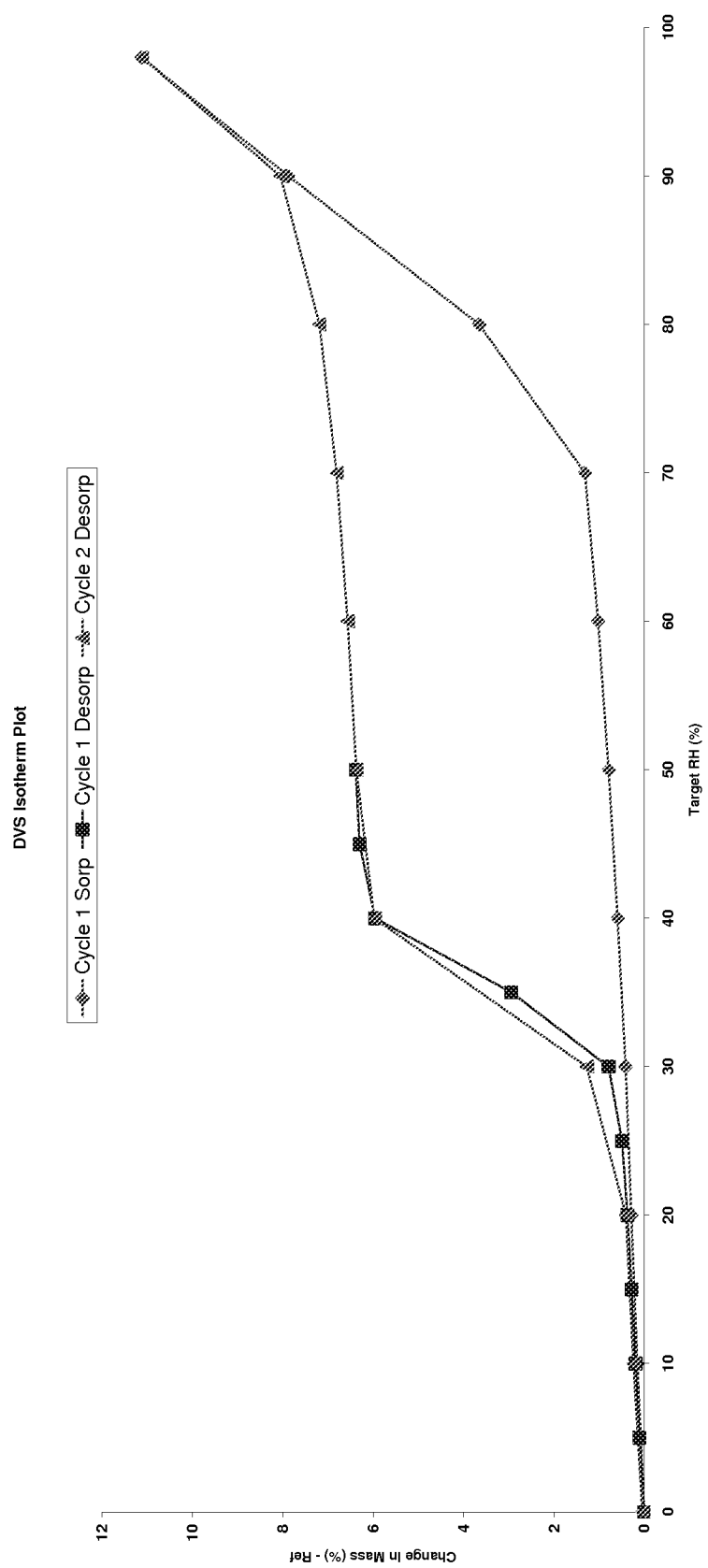
FIG. 14 depicts the Water Vapour Sorption Isotherm (25° C.) (SMS DVS Intrinsic) of crystalline modification H1 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate.

Water Vapor Sorption behavior shows loss of hydrate water <40% relative humidity (RH), with re-conversion to dihydrate crystalline modification H1 upon adsorption >70% RH. Water Vapor Sorption isotherm (25° C.) of Form H1 is displayed below. Water Vapor Sorption isotherm [Water Vapour Sorption Isotherm (25° C.) (SMS DVS Intrinsic)] of crystalline modification H1 is displayed in FIG. 14.

Example 7

Structural and Physico-Chemical Characterization of 6-(1-methyl-1H-pyrazol-4-yl)-2-{3-[5-(2-morpholin-4-yl-ethoxy)-pyrimidin-2-yl]-benzyl}-2H-pyridazin-3-one Dihydrogenphosphate in its Crystalline Modification NF3

Figure 15:
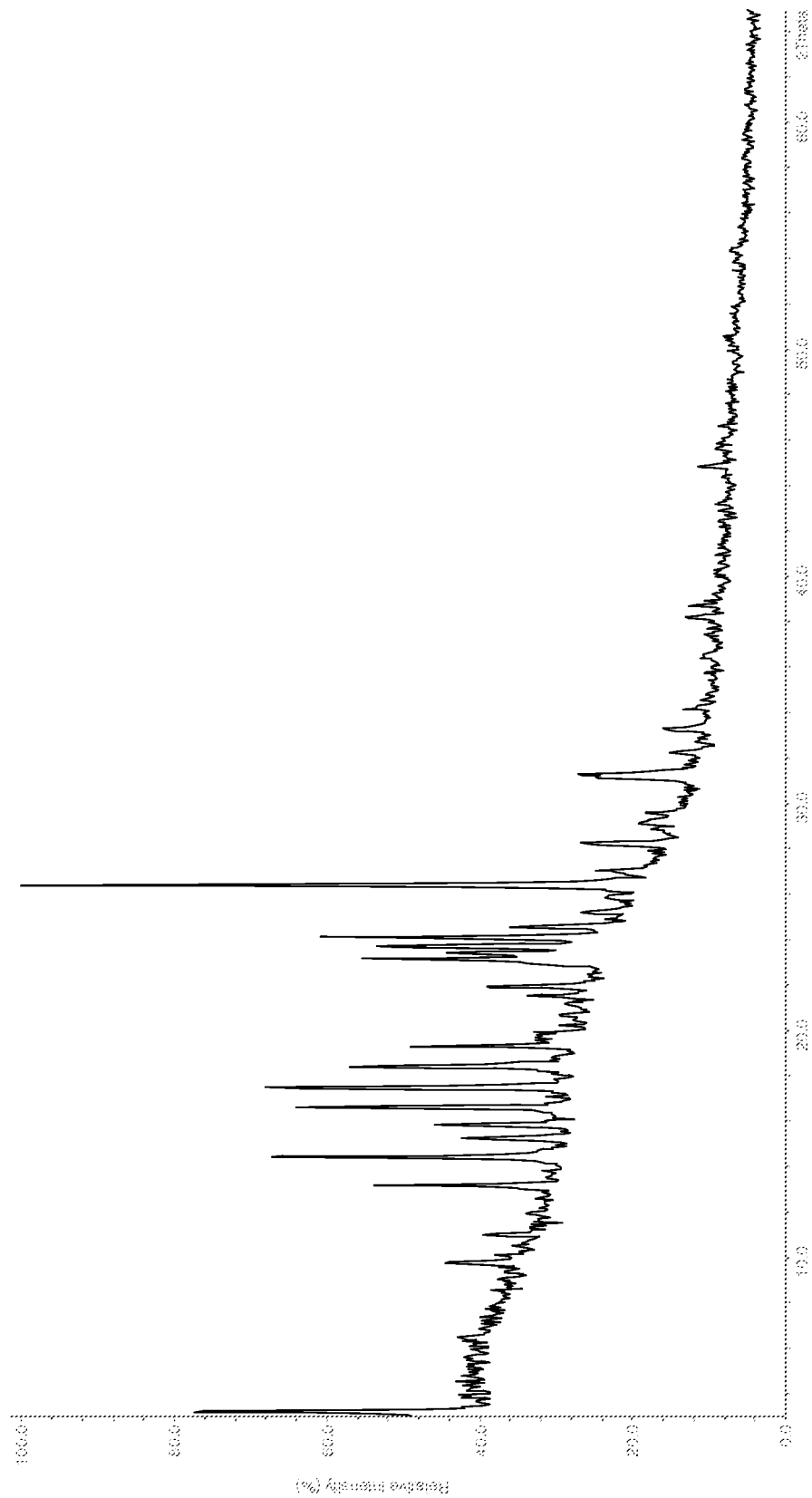
FIG. 15 depicts the powder X-ray diffractogram of crystalline modification NF3 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate.

A Powder X-Ray Diffraction (XRD) pattern of crystalline modification NF3 was obtained by standard techniques as described in European Pharmacopeia, 6$^{th}$ Edition, chapter 2.9.33. Crystalline modification NF3 is characterized by the X-ray powder diffractogram (Cu-K$\alpha_1$ radiation, $\lambda$=1.5406 Å, Stoe StadiP 611 KL diffractometer.) depicted in FIG. 15.

Crystalline modification NF3 is characterized by the following XRD data:

Powder X-Ray Diffractogram Peak List:

| Peak No. | d/Å | °2θ (Cu—K$\alpha_1$ radiation) ± 0.1° |
|---|---|---|
| 1 | 27.30 | 3.2 |
| 2 | 13.62 | 6.5 |
| 3 | 9.02 | 9.8 |
| 4 | 6.71 | 13.2 |
| 5 | 6.11 | 14.5 |
| 6 | 5.79 | 15.3 |
| 7 | 5.57 | 15.9 |
| 9 | 5.32 | 16.7 |
| 9 | 5.05 | 17.5 |
| 10 | 4.81 | 18.4 |
| 11 | 4.58 | 19.4 |
| 12 | 4.12 | 21.6 |
| 13 | 4.04 | 22.0 |
| 14 | 3.84 | 23.1 |
| 15 | 3.75 | 23.7 |
| 16 | 3.69 | 24.1 |
| 17 | 3.37 | 26.4 |
| 18 | 3.16 | 28.3 |

Crystalline modification NF3 was further characterized by IR- and Raman-spectroscopy. FT-Raman and FT-IR spectra were obtained by standard techniques as described in the European Pharmacopeia, 6$^{th}$ Edition, chapter 2.02.24 and 2.02.48. For measurement of the FT-IR and FT-Raman-spectra a Bruker Vector 22 and a Bruker RFS 100 spectrometer were used. FT-IR spectra were base-line corrected using Bruker OPUS software. FT-Raman spectra were vector normalized using the same software.

Figure 16:
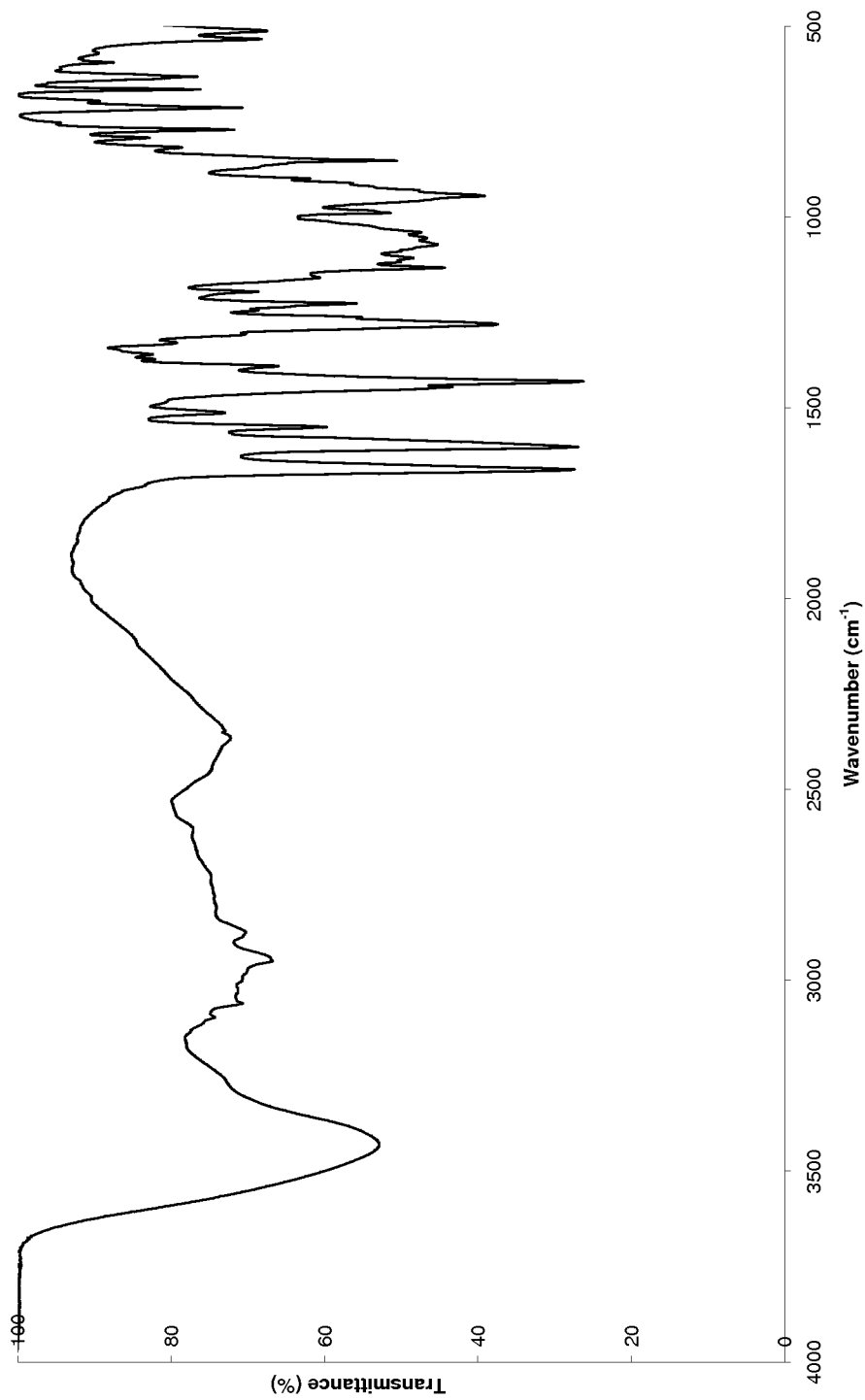
FIG. 16 depicts the FT-IR spectrum of crystalline modification NF3 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate.

An FT-IR spectrum was obtained using a KBr pellet as sample preparation technique. The FT-IR spectrum is depicted in FIG. 16 and the band positions are given below.

Crystalline modification NF3 IR band positions ±2 cm$^{-1}$ (relative intensity*) 2949 cm$^{-1}$ (m), 2873 cm$^{-1}$ (w), 2365 cm$^{-1}$ (w, broad), 1661 cm$^{-1}$ (s), 1602 cm$^{-1}$ (s), 1549 cm$^{-1}$ (m), 1445 cm$^{-1}$ (s), 1430 cm$^{-1}$ (s), 1280 cm$^{-1}$ (s), 1262 cm$^{-1}$ (m), 1226 cm$^{-1}$ (m), 1132 cm$^{-1}$ (s), 1072 cm$^{-1}$ (s), 944 cm$^{-1}$ (s), 851 cm$^{-1}$ (s), 713 cm$^{-1}$ (m)

*"s"=strong (transmittance≤50%), "m"=medium (50%<transmittance≤70%), "w"=weak (transmittance>70%)

Figure 17:
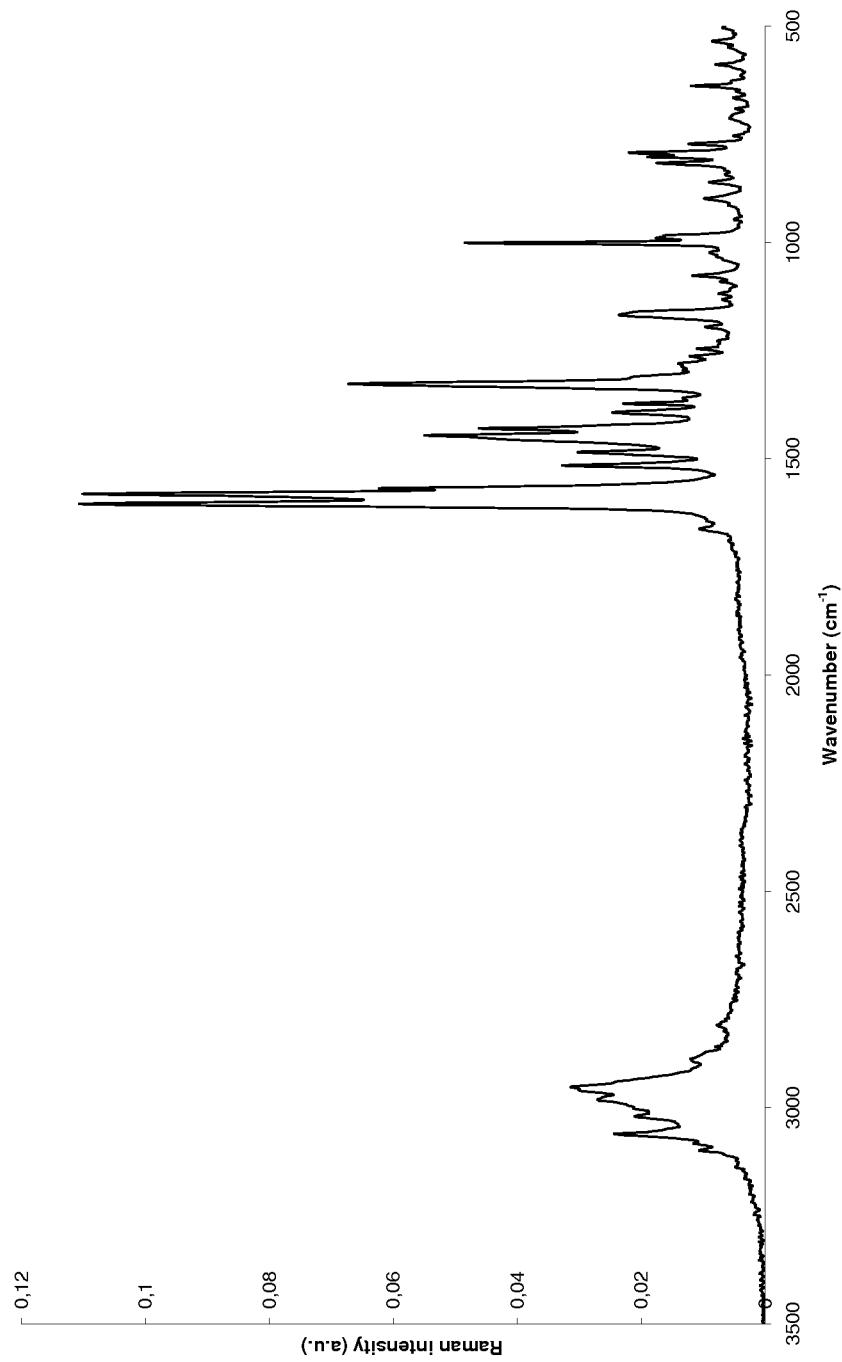
FIG. 17 depicts the FT-Raman spectrum of crystalline modification NF3 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate.

An FT-Raman spectrum is depicted in FIG. 17 and the band positions are given below.

Crystalline modification NF3 Raman band positions ±2 cm$^{-1}$ (relative intensity*): 3061 cm$^{-1}$ (m), 2952 cm$^{-1}$ (m), 1604 cm$^{-1}$ (s), 1581 cm$^{-1}$ (s), 1568 cm$^{-1}$ (s), 1515 cm$^{-1}$ (m), 1446 cm$^{-1}$ (s), 1430 cm$^{-1}$ (s), 1327 cm$^{-1}$ (s), 1167 cm$^{-1}$ (m), 1001 cm$^{-1}$ (s), 802 cm$^{-1}$ (w), 793 cm$^{-1}$ (w)

*"s"=strong (relative Raman intensity≥0.04), "m"=medium (0.04>relative Raman intensity≥0.02), "w"=weak (relative Raman intensity<0.02)

Figure 18:
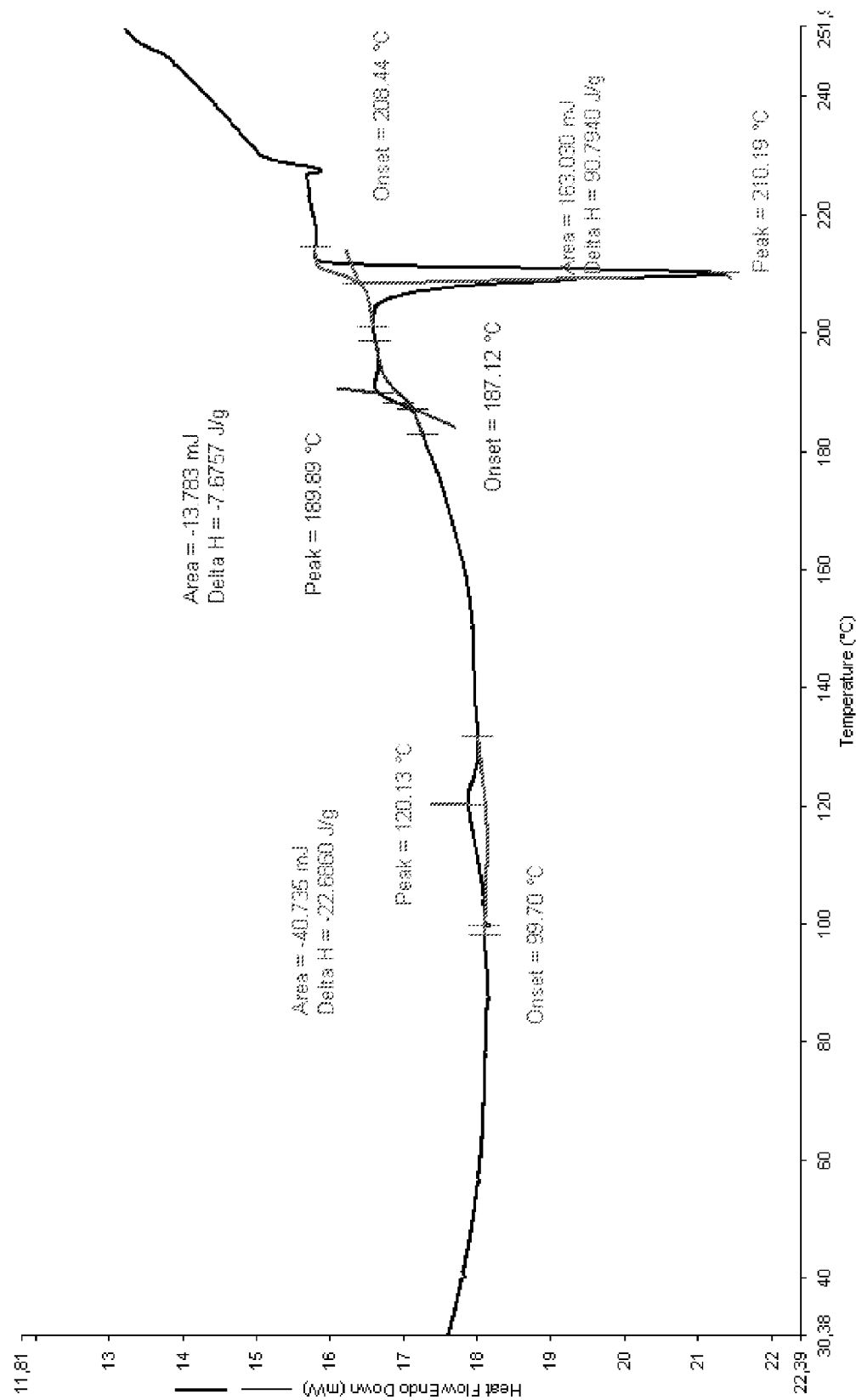
FIG. 18 depicts the DSC scan profile (Perkin-Elmer Diamond DSC, 5 K/min, nitrogen purge gas 50 mL/min) of crystalline modification NF3 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate.
Figure 19:
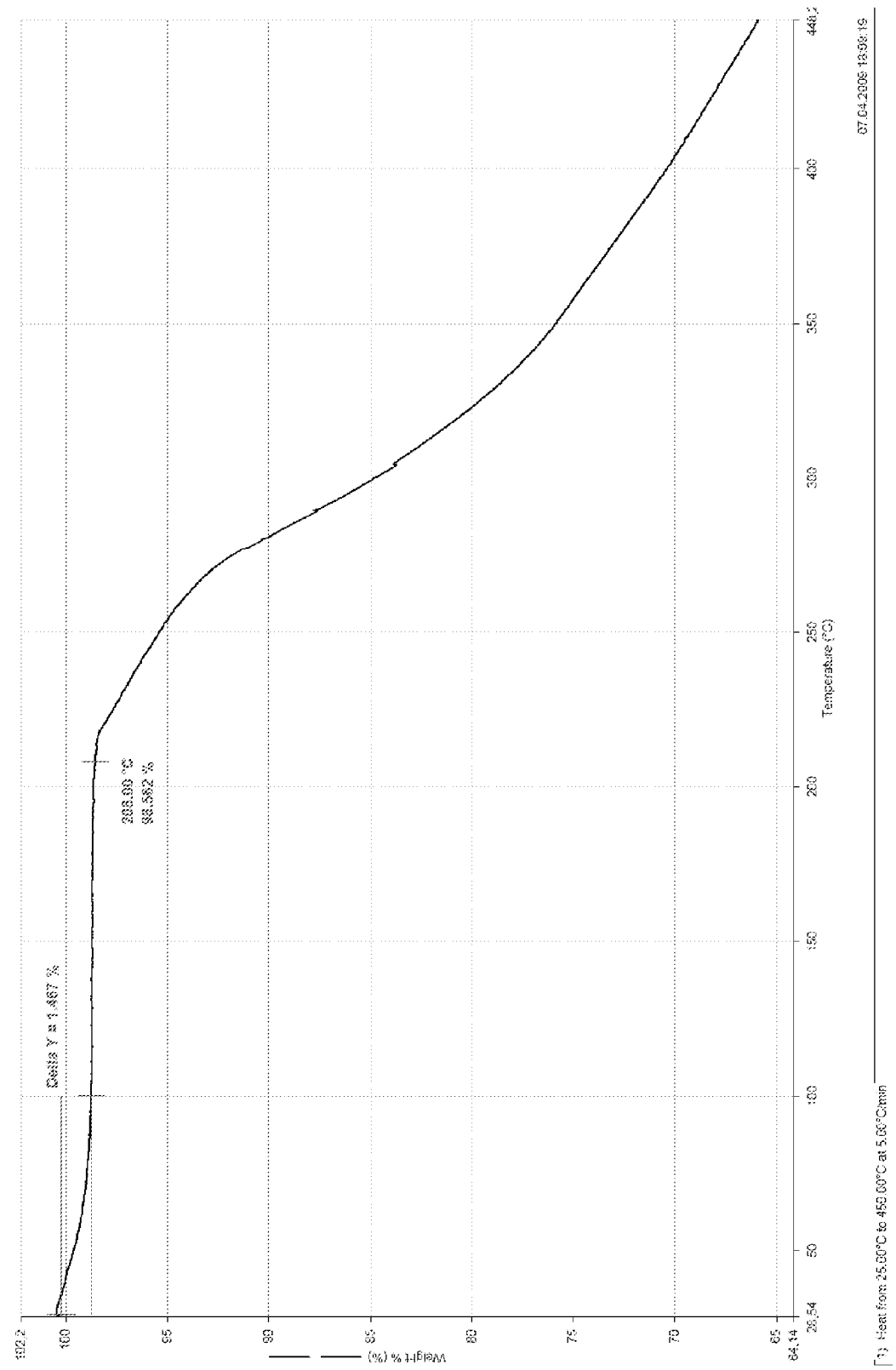
FIG. 19 depicts the TGA scan profile (Perkin-Elmer Pyris TGA1, 5 K/min, nitrogen purge gas 50 mL/min) of crystalline modification NF3 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate.

Crystalline modification NF3 is a crystalline form, most likely an anhydrate form, which is further characterized by the following physical properties:

Thermal behavior shows two exothermic events at approx. 100-130° C. and 180-190° C., followed by a melting peak at approx. 208° C., with a small mass loss of approx. 1.5 wt % up to the melting temperature. DSC profile (Perkin-Elmer Diamond DSC, 5 K/min, nitrogen purge gas 50 mL/min) and TGA profile (Perkin-Elmer Pyris TGA1, 5 K/min, nitrogen purge gas 50 mL/min) are displayed in FIGS. 18 and 19, respectively.

Figure 20:
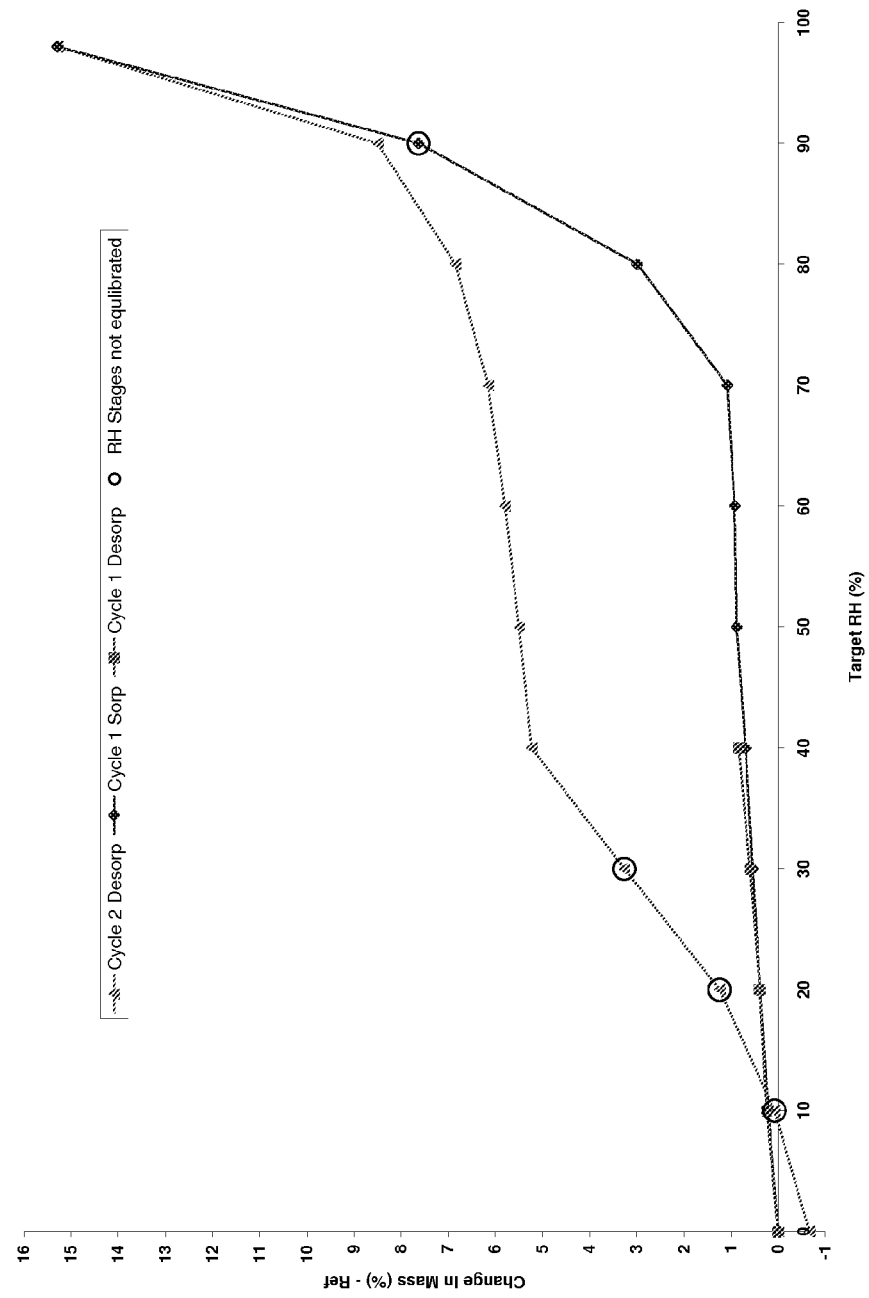
FIG. 20 depicts the Water Vapour Sorption Isotherm (25° C.) (SMS DVS Intrinsic) of crystalline modification NF3 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate.

Water Vapor Sorption behavior shows small water uptake levels upon adsorption in the range 0-70% relative humidity (RH). Pronounced water uptake levels are observed above 70% RH, which results in formation of crystalline hydrate modification NF5 (water uptake levels of approx. 5-6 wt %) at elevated relative humidity (RH). A Water Vapor Sorption isotherm [Water Vapour Sorption Isotherm (25° C.) (SMS DVS Intrinsic)] of crystalline modification NF3 is displayed in FIG. 20.

Example 8

Structural and Physico-Chemical Characterization of 6-(1-methyl-1H-pyrazol-4-yl)-2-{3-[5-(2-morpholin-4-yl-ethoxy)-pyrimidin-2-yl]-benzyl}-2H-pyridazin-3-one Dihydrogenphosphate Hydrate in its Crystalline Modification NF5

Figure 21:
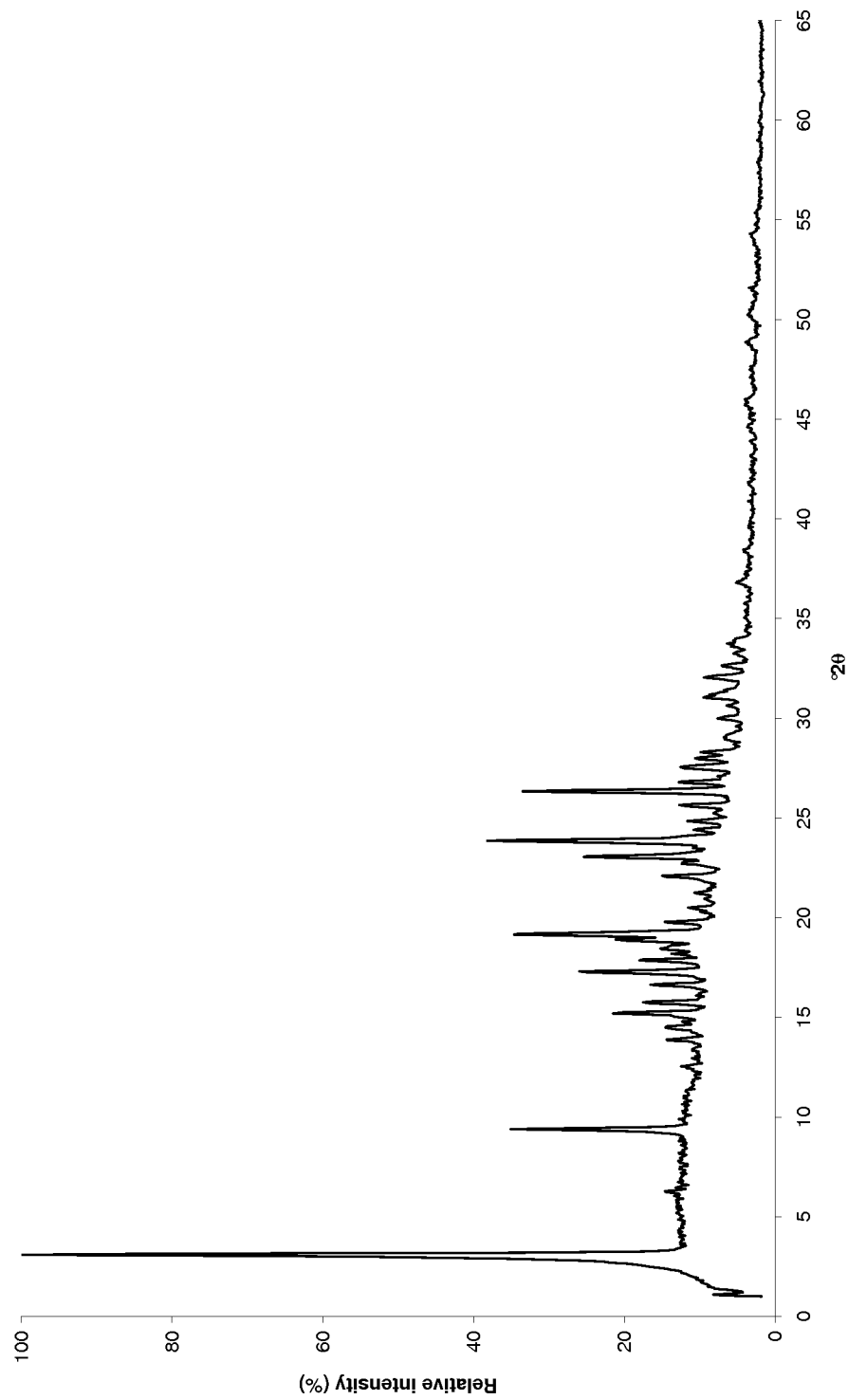
FIG. 21 depicts the powder X-ray diffractogram of crystalline modification NF5 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate.

A Powder X-Ray Diffraction (XRD) pattern of crystalline modification NF5 was obtained by standard techniques as described in European Pharmacopeia, 6$^{th}$ Edition, chapter 2.9.33. Crystalline modification NF5 is characterized by the X-ray powder diffractogram (Cu-K$\alpha_1$ radiation, λ=1.5406 Å, Stoe StadiP 611 KL diffractometer.) depicted in FIG. 21.

Crystalline modification NF5 is characterized by the following XRD data:
Powder X-Ray Diffractogram Peak List:

| Peak No. | d/Å | °2θ (Cu—K$\alpha_1$ radiation) ± 0.1° |
|---|---|---|
| 1 | 28.54 | 3.1 |
| 2 | 9.41 | 9.4 |
| 3 | 6.37 | 13.9 |
| 4 | 6.10 | 14.5 |
| 5 | 5.98 | 14.8 |
| 6 | 5.82 | 15.2 |
| 7 | 5.62 | 15.7 |
| 9 | 5.32 | 16.6 |
| 9 | 5.13 | 17.3 |
| 10 | 4.96 | 17.9 |
| 11 | 4.80 | 18.5 |
| 12 | 4.69 | 18.9 |
| 13 | 4.63 | 19.2 |
| 14 | 4.48 | 19.8 |
| 15 | 4.02 | 22.1 |
| 16 | 3.90 | 22.8 |
| 17 | 3.85 | 23.1 |
| 18 | 3.73 | 23.9 |
| 19 | 3.38 | 26.3 |
| 20 | 3.32 | 26.8 |
| 21 | 3.23 | 27.6 |

Figure 22:
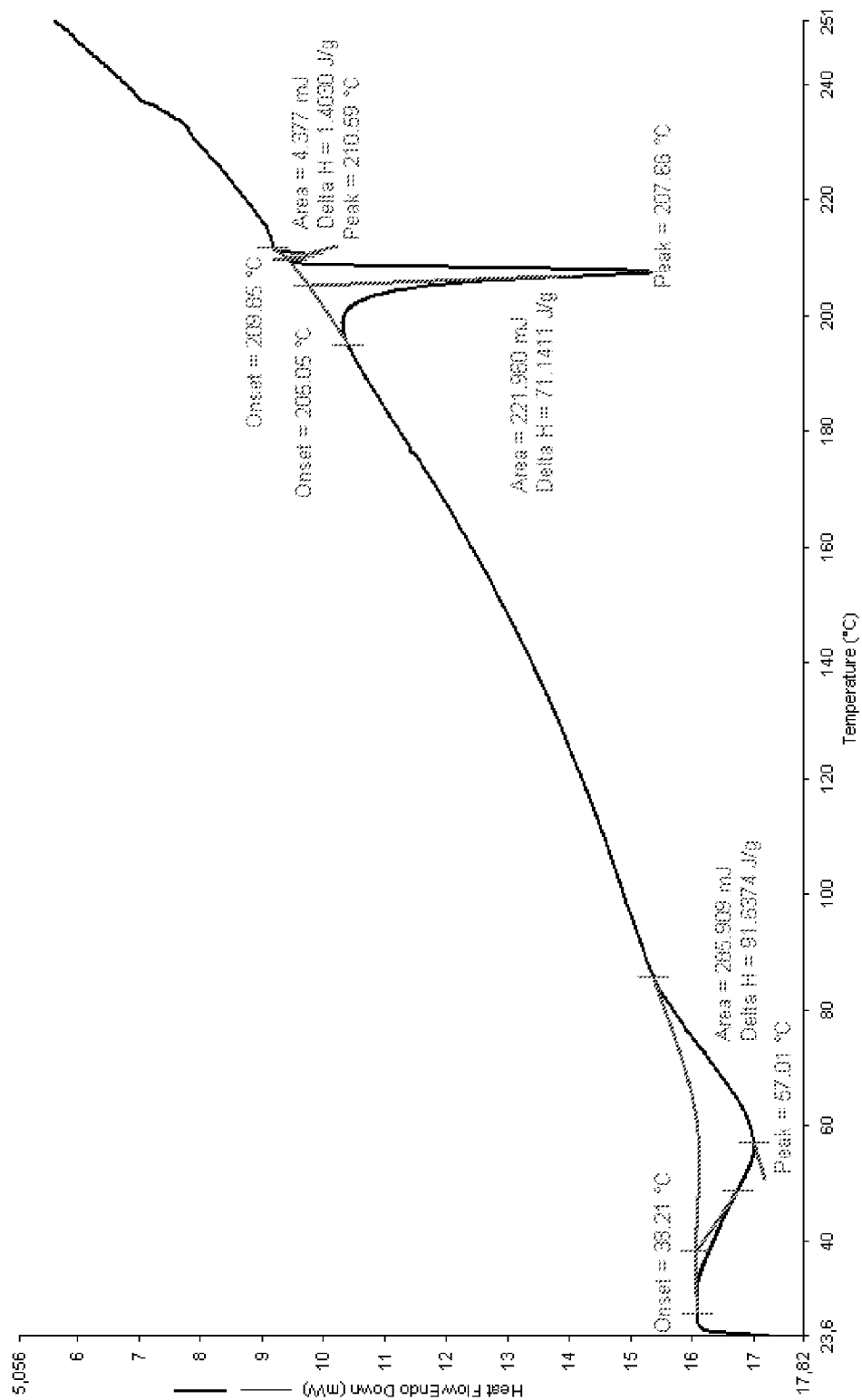
FIG. 22 depicts the DSC scan profile (Perkin-Elmer Diamond DSC, 5 K/min, nitrogen purge gas 50 mL/min) of crystalline modification NF5 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate.
Figure 23:
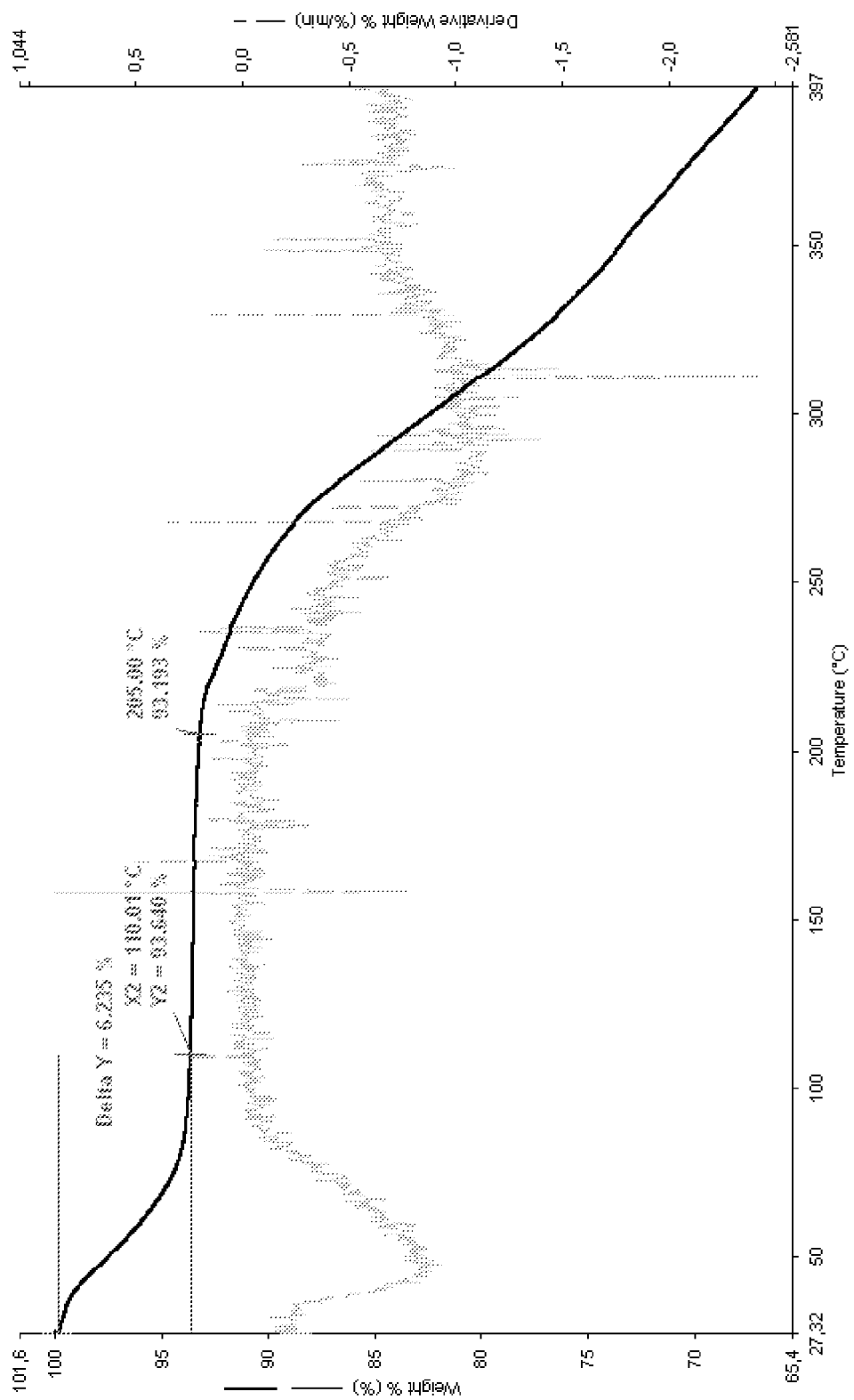
FIG. 23 depicts the TGA scan profile (Perkin-Elmer Pyris TGA1, 5 K/min, nitrogen purge gas 50 mL/min) of crystalline modification NF5 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate.

Crystalline modification NF5 is a crystalline hydrate form, which is further characterized by the following physical properties:

Thermal behavior shows dehydration of hydrate water from approx. 30-100° C. upon heating, with subsequent melting of the anhydrous form at approx. 210° C. DSC profile (Perkin-Elmer Diamond DSC, 5 K/min, nitrogen purge gas 50 mL/min) and TGA profile (Perkin-Elmer Pyris TGA1, 5 K/min, nitrogen purge gas 50 mL/min) are displayed in FIGS. 22 and 23, respectively.

Figure 24:
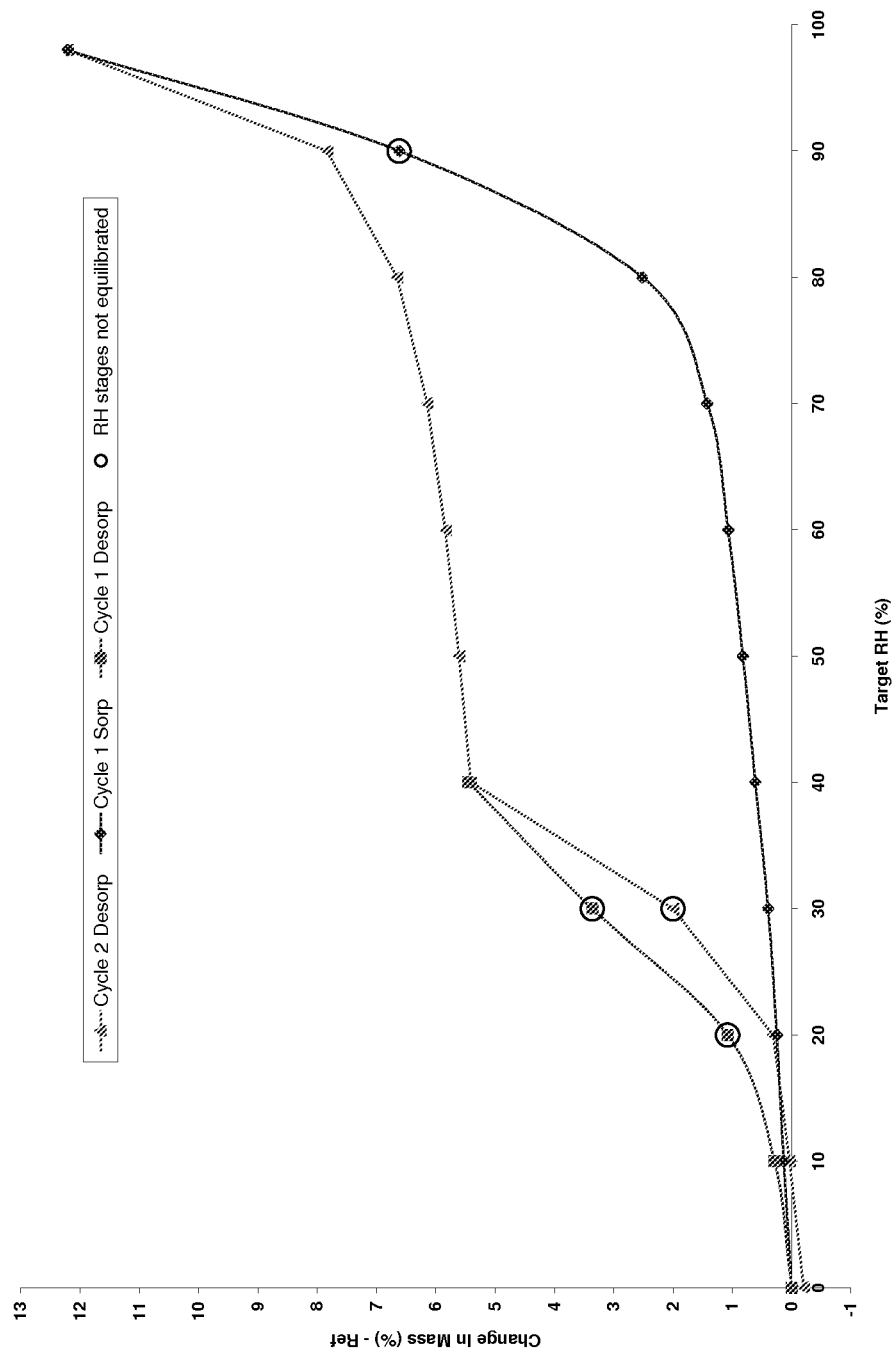
FIG. 24 depicts the Water Vapour Sorption Isotherm (25° C.) (SMS DVS Intrinsic) of crystalline modification NF5 of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate.

Water Vapor Sorption behavior shows loss of hydrate water <40% relative humidity (RH), with re-conversion to hydrate crystalline modification NF5 upon adsorption >70% RH. Water Vapor Sorption isotherm (25° C.) of Form NF5 is displayed below. Water Vapor Sorption isotherm [Water Vapour Sorption Isotherm (25° C.) (SMS DVS Intrinsic)] of crystalline modification NF5 is displayed in FIG. 24.

Example 9

Solubility Determination of 6-(1-methyl-1H-pyrazol-4-yl)-2-{3-[5-(2-morpholin-4-yl-ethoxy)-pyrimidin-2-yl]-benzyl}-2H-pyridazin-3-one Dihydrogenphosphate For solubility determination 6-(1-methyl-1H-pyrazol-4-yl)-2-{3-[5-(2-morpholin-4-yl-ethoxy)-pyrimidin-2-yl]-benzyl}-2H-pyridazin-3-one (free base) and its dihydrogenphosphate salt are weighted into a GC-Vial, 300 μL of the solvent medium are added to result in a maximal possible concentration of 10 mg/mL. The mixture is stirred at 1000 rpm on a magnetic stirring plate at ambient temperature. At the sampling point 100 μL of the respective solution/suspension are transferred to a 500 μL Eppendorff cap and are centrifuged for 5 min at 14000 rpm. The centrifugate is analysed by HPLC (dilution may be necessary before analysis).

Table 1 shows the solubility of the free base of 6-(1-methyl-1H-pyrazol-4-yl)-2-{3-[5-(2-morpholin-4-yl-ethoxy)-pyrimidin-2-yl]-benzyl}-2H-pyridazin-3-one and its corresponding dihydrogenphosphate salt in water, measured after 1 and 2 hours.

TABLE 1

| | Sample Point 1 h | | Sample Point 2 h | |
|---|---|---|---|---|
| | Solubility [mg/ml] | pH value | Solubility [mg/ml] | pH value |
| free base | 0.167 | n.d. | 0.156 | n.d. |
| dihydrogenphosphate | 9.863 | 3.91 | >10 | 3.97 |

The results clearly demonstrate the significantly higher solubility of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate in aqueous solutions compared to its free base.

Example 10

Competitive slurry conversion experiments of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate crystalline modifications A1 and NF3 in organic solvents.

Approximately 10 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate crystalline modification A1 and 10 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate crystalline modification NF3 were mixed as powder blend, and dispersed in 1 mL organic solvent in 4 mL glass vials with PTFE sealed caps. PTFE-coated stirring rods were inserted into the dispersions prior to sealing the vials. Dispersions were agitated in closed vials for 5 days, using a magnetic stirrer, at 25° C. and 50° C., respectively. Solid-state residues were filtered, and analyzed by XRD to monitor morphic form after solvent slurrying.

The results of the competitive slurry conversion experiments are compiled in Table 2.

TABLE 2

| | Mixtures A1 + NF3 (approx. 1:1, wt/wt) | |
|---|---|---|
| Slurry in | Residue 25° C., 5 d | Residue 50° C., 5 d |
| Acetone | A1 | A1 |
| Ethanol | A1 | A1 |
| 1,4-Dioxane | A1 | A1 |
| THF | A1 + very small fraction NF3 | A1 |

At both temperatures, crystalline modification A1 is obtained as only or preferred form at the end of the slurry experiments starting from binary 1:1 mixtures of forms A1 and NF3, clearly demonstrating that A1 can be considered as more stable form.

Example 11

A competitive slurry conversion experiment of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate crystalline modifications A1 and NF5 in water.

Approximately 20 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate crystalline modification A1 and 20 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate crystalline modification NF5 were mixed as powder blend, and dispersed in 0.3 mL water in a 4 mL glass vial with a PTFE sealed cap. A PTFE-coated stirring rod was inserted into the dispersion prior to sealing the vial. The dispersion was agitated in closed vial for 12 days, using a magnetic stirrer, at 25° C. The solid-state residue was filtered, and analyzed by XRD to monitor morphic form after solvent slurrying.

The result of the competitive slurry conversion experiment is compiled in Table 3.

TABLE 3

| Slurry in | Mixtures A1 + NF5 (approx. 1:1, wt/wt) Residue 25° C., 12 d |
|---|---|
| Water | NF5 + very small fractions of A1 |

The experiments shows that prolonged aqueous slurrying of modifications A1 and NF5 at 25° C. results in hydrate form NF5 as preferred form, clearly showing that NF5 is the more stable form in an aqueous dispersion system.

Example 12

A competitive slurry conversion experiment of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate crystalline modifications H1 and NF5 in water.

Approximately 20 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate crystalline modification H1 and 20 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate crystalline modification NF5 were mixed as powder blend, and dispersed in 0.3 mL water in a 4 mL glass vial with a PTFE sealed cap. A PTFE-coated stirring rod was inserted into the dispersion prior to sealing the vial. The dispersion was agitated in closed vial for 12 days, using a magnetic stirrer, at 25° C. The solid-state residue was filtered, and analyzed by XRD to monitor morphic form after solvent slurrying.

The result of the competitive slurry conversion experiment is compiled in Table 4.

TABLE 4

| Slurry in | Mixtures H1 + NF5 (approx. 1:1, wt/wt) Residue 25° C., 12 d |
|---|---|
| Water | H1 |

The experiments shows that prolonged aqueous slurrying of modifications H1 and NF5 at 25° C. results in dihydrate form H1 as preferred form, clearly showing that H1 is a stable form in an aqueous dispersion system.

Example 13

A competitive slurry conversion experiment of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate crystalline modifications H1 and NF3 in water.

Approximately 10 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate crystalline modification H1 and 10 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate crystalline modification NF3 were mixed as powder blend, and dispersed in 0.2 mL water in a 4 mL glass vial with a PTFE sealed cap. A PTFE-coated stirring rod was inserted into the dispersion prior to sealing the vial. The dispersion was agitated in closed vial for 5 days, using a magnetic stirrer, at 25° C. The solid-state residue was filtered, and analyzed by XRD to monitor morphic form after solvent slurrying.

The result of the competitive slurry conversion experiment is compiled in Table 5.

TABLE 5

| Slurry in | Mixtures H1 + NF3 (approx. 1:1, wt/wt) Residue 25° C., 5 d |
|---|---|
| Water | H1 |

The experiments shows that prolonged aqueous slurrying of modifications H1 and NF3 at 25° C. results in dihydrate form H1 as preferred form, clearly showing that H1 is a more stable form in an aqueous dispersion system.

Example 14

Kinetic solubility determinations of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate crystalline forms A1 (anhydrate) and NF3 in a mixture of water:acetone 30:70 (v:v) after 2 hours.

Approximately 70 mg of 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate crystalline modification A1 were dispersed in 1 mL of a binary mixture water:acetone (30:70, v:v) in a 5 mL Whitman Uniprep Syringeless Filter vial. The dispersion was agitated at RT for 2 hours at 450 rpm. After filtration of the dispersion after 2 hours, the filtrate is analysed by HPLC (dilution may be necessary before analysis). The solid-state residue is analysed by Powder X-Ray Diffraction (PXRD).

The results of the kinetic solubility determination in water:acetone is compiled in Table 6.

TABLE 6

| Form | Solubility water:acetone (30:70, v:v) after 2 h [mg/mL] | SS Residue |
|---|---|---|
| A1 | 18.2 | H1 |
| NF3 | 10.6 | H1 + NF5 |

Both anhydrous forms undergo conversion to dihydrate form H1 (in mixture with hydrate form NF5 in case of form NF3). The corresponding solubility levels clearly show that form NF3 exhibits a lower solubility level after 2 hours than form A1.

The invention claimed is:

1. 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate solvate.

2. 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate.

3. The compound of claim 2 in its crystalline modification A1, which is characterized by XRD peaks comprising 3.2°, 6.5°, 9.8°, and 13.1° 2θ (all ±0.1° 2θ, using Cu-Kα₁ radiation).

4. The compound of claim 2 in its crystalline modification A1, which is characterized by XRD peaks comprising 18.4°, 18.8°, 23.7°, 24.2°, 26.4°, and 28.2° 2θ (all ±0.1° 2θ, using Cu-Kα₁ radiation).

5. The compound of claim 2 in its crystalline modification A1, which is characterized by XRD peaks comprising 14.4°, 15.8°, 17.5°, 19.5°, and 21.9° 2θ (all ±0.1° 2θ, using Cu-Kα₁ radiation).

6. The compound of claim 2 in its crystalline modification A1, which is characterized by the following XRD data:

Form A1:

| Peak No. | d/Å | °2θ (Cu—Kα₁ radiation) ± 0.1° |
|---|---|---|
| 1 | 27.45 | 3.2 |
| 2 | 13.62 | 6.5 |
| 3 | 9.02 | 9.8 |
| 4 | 6.75 | 13.1 |
| 5 | 6.15 | 14.4 |
| 6 | 5.59 | 15.8 |
| 7 | 5.07 | 17.5 |
| 8 | 4.81 | 18.4 |
| 9 | 4.72 | 18.8 |
| 10 | 4.55 | 19.5 |
| 11 | 4.06 | 21.9 |
| 12 | 3.75 | 23.7 |
| 13 | 3.68 | 24.2 |
| 14 | 3.37 | 26.4 |
| 15 | 3.16 | 28.2. |

7. 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate.

8. The compound of claim 7 in its crystalline modification H1, which is characterized by XRD peaks comprising 3.1°, 9.4°, and 18.8° 2θ (all ±0.1° 2θ, using Cu-Kα₁ radiation).

9. The compound of claim 7 in its crystalline modification H1, which is characterized by XRD peaks comprising 19.1°, 22.8°, and 26.4° 2θ (all ±0.1° 2θ, using Cu-Kα₁ radiation).

10. The compound of claim 7 in its crystalline modification H1, which is characterized by XRD peaks comprising 14.4°, 15.0°, and 17.8° 2θ (all ±0.1° 2θ, using Cu-Kα₁ radiation).

11. The compound of claim 7 in its crystalline modification H1, which is characterized by XRD peaks comprising 14.7°, 18.6°, 23.2°, 23.8°, 26.8°, and 27.6° 2θ (all ±0.1° 2θ, using Cu-Kα₁ radiation).

12. The compound of claim 7 in its crystalline modification H1, which is characterized by the following XRD data:

Form H1:

| Peak No. | d/Å | °2θ (Cu—Kα₁ radiation) ± 0.1° |
|---|---|---|
| 1 | 28.42 | 3.1 |
| 2 | 9.40 | 9.4 |
| 3 | 6.13 | 14.4 |
| 4 | 6.01 | 14.7 |
| 5 | 5.89 | 15.0 |
| 6 | 4.97 | 17.8 |
| 7 | 4.77 | 18.6 |
| 8 | 4.71 | 18.8 |
| 9 | 4.64 | 19.1 |
| 10 | 3.89 | 22.8 |
| 11 | 3.83 | 23.2 |
| 12 | 3.73 | 23.8 |
| 13 | 3.38 | 26.4 |
| 14 | 3.33 | 26.8 |
| 15 | 3.22 | 27.6. |

13. 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate in its crystalline modification NF3, which is characterized by XRD peaks comprising 15.3°, 16.7°, 21.6°, and 23.1° 2θ (all ±0.1° 2θ, using Cu-Kα₁ radiation).

14. The compound of claim 13 in its crystalline modification NF3, which is characterized by the following XRD data:

Form NF3:

| Peak No. | d/Å | °2θ (Cu—Kα₁ radiation) ± 0.1° |
|---|---|---|
| 1 | 27.30 | 3.2 |
| 2 | 13.62 | 6.5 |
| 3 | 9.02 | 9.8 |
| 4 | 6.71 | 13.2 |
| 5 | 6.11 | 14.5 |
| 6 | 5.79 | 15.3 |
| 7 | 5.57 | 15.9 |
| 9 | 5.32 | 16.7 |
| 9 | 5.05 | 17.5 |
| 10 | 4.81 | 18.4 |
| 11 | 4.58 | 19.4 |
| 12 | 4.12 | 21.6 |
| 13 | 4.04 | 22.0 |
| 14 | 3.84 | 23.1 |
| 15 | 3.75 | 23.7 |
| 16 | 3.69 | 24.1 |
| 17 | 3.37 | 26.4 |
| ä18 | 3.16 | 28.3. |

15. 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate.

16. The compound of claim 15 in its crystalline modification NF5, which is characterized by XRD peaks comprising 13.9°, 15.7°, 16.6°, 17.3°, 19.8°, and 22.1° 2θ (all ±0.1° 2θ, using Cu-Kα₁ radiation).

17. The compound of claim 15 in its crystalline modification NF5, which is characterized by the following XRD data:

Form NF5:

| Peak No. | d/Å | °2θ (Cu—Kα$_1$ radiation) ± 0.1° |
|---|---|---|
| 1 | 28.54 | 3.1 |
| 2 | 9.41 | 9.4 |
| 3 | 6.37 | 13.9 |
| 4 | 6.10 | 14.5 |
| 5 | 5.98 | 14.8 |
| 6 | 5.82 | 15.2 |
| 7 | 5.62 | 15.7 |
| 9 | 5.32 | 16.6 |
| 9 | 5.13 | 17.3 |
| 10 | 4.96 | 17.9 |
| 11 | 4.80 | 18.5 |
| 12 | 4.69 | 18.9 |
| 13 | 4.63 | 19.2 |
| 14 | 4.48 | 19.8 |
| 15 | 4.02 | 22.1 |
| 16 | 3.90 | 22.8 |
| 17 | 3.85 | 23.1 |
| 18 | 3.73 | 23.9 |
| 19 | 3.38 | 26.3 |
| 20 | 3.32 | 26.8 |
| 21 | 3.23 | 27.6. |

18. A pharmaceutical composition comprising at least one compound according to claim 1 and a pharmaceutically acceptable carrier.

19. A pharmaceutical composition comprising at least one compound according to claim 2 and a pharmaceutically acceptable carrier.

20. A process for preparing crystalline modification A1 according to claim 3 comprising
   (a) dissolving or dispersing 6-(1-methyl-1H-pyrazol-4-yl)-2-{3-[5-(2-morpholin-4-yl-ethoxy)-pyrimidin-2-yl]-benzyl}-2H-pyridazin-3-one in free base form or one or more salts thereof in a solvent or a solvent mixture, optionally under stirring,
   (b) converting 6-(1-methyl-1H-pyrazol-4-yl)-2-{3-[5-(2-morpholin-4-yl-ethoxy)-pyrimidin-2-yl]-benzyl}-2H-pyridazin-3-one in free base form or one or more salts thereof into the corresponding dihydrogenphosphate salt by addition of aqueous or ethanolic phosphoric acid solution, optionally under stirring,
   (c) stirring the resulting dispersion of (b) at room temperature for one or more hours or days,
   (d) recovering precipitated 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate by filtration, optionally subsequent washing with a solvent or a solvent mixture, and optionally subsequent drying, optionally in vacuo, optionally at elevated temperature T, of 30° C. to 95° C.

21. A process for preparing crystalline modification A1 according to claim 3 comprising
   (a) dispersing 6-(1-methyl-1H-pyrazol-4-yl)-2-{3-[5-(2-morpholin-4-yl-ethoxy)-pyrimidin-2-yl]-benzyl}-2H-pyridazin-3-one in free base form or one or more salts thereof in a solvent or a solvent mixture and addition of aqueous phosphoric acid solution, optionally under stirring,
   (b) heating the resulting dispersion of (a) up to elevated temperature T1, which is 30° C. to 95° C., optionally under stirring, and cooling down the resulting solution, to 0° C. to 40° C., optionally under stirring, before diluting it with a solvent or a solvent mixture, optionally under stirring,
   (c) stirring the resulting dispersion of (b) at 0° C. to 40° C., until crystallization is complete and/or incubating it at room temperature for one or more hours or days, optionally under stirring,
   (d) recovering precipitated 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate by filtration, optionally cooling down the resulting dispersion of (c) to 0° C. to 20° C., prior to filtration optionally under stirring, optionally subsequent washing with a solvent or a solvent mixture, and optionally subsequent drying, optionally at elevated temperature T2, of 30° C. to 95° C.,
   (e) optionally, boiling the resulting dried crystals of (d) in a solvent or a solvent mixture, as dispersion, for one or more minutes, and recovering them by filtration from the hot dispersion.

22. A process for preparing crystalline modification A1 according to claim 3 comprising
   (a) dispersing 6-(1-methyl-1H-pyrazol-4-yl)-2-{3-[5-(2-morpholin-4-yl-ethoxy)-pyrimidin-2-yl]-benzyl}-2H-pyridazin-3-one in free base form or one or more salts thereof in a solvent mixture, and addition of aqueous phosphoric acid solution, optionally under stirring,
   (b) heating the resulting dispersion of (a) up to elevated temperature T1, of 30° C. to 95° C., optionally under stirring, and cooling down the resulting solution, optionally under stirring, with a defined cooling rate, of 0.1-1 K/min, optionally under stirring, until crystallization sets in,
   (c) further cooling the resulting dispersion of (b) to −20° C. to 0° C., optionally under stirring, with a defined cooling rate, of 0.1-1 K/min, optionally under stirring,
   (d) stirring the resulting dispersion of step (c) at −20° C. to 40° C., until crystallization is complete,
   (e) recovering crystallized 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate by filtration, optionally subsequent washing with a solvent or a solvent mixture, and optionally subsequent drying, optionally at elevated temperature T2, of from 30° C. to 95° C.

23. A process for preparing crystalline modification H1 according to claim 8 comprising
   (a) spreading 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate crystalline modification A1 onto a bordered surface of a container, and subsequently incubating it in a sealed desiccator over water or an aqueous solvent mixture for one or more days or weeks.

24. A process for preparing crystalline modification H1 according to claim 10 comprising
   (a) dispersing 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate crystalline modification A1 in a mixture of two or more solvents, optionally under stirring, and stirring the resulting dispersion at elevated temperature T1, of 30° C. to 95° C., for one or more days or weeks,
   (b) recovering precipitated 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate dihydrate by filtration, optionally subsequent washing with a solvent or a solvent mixture, and optionally subsequent drying, optionally at elevated temperature T2, of 30° C. to 95° C.

25. A process for preparing crystalline modification NF3 according to claim 13, comprising
- (a) dispersing or dissolving 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate crystalline modification A1 in a mixture of two or more solvents, optionally under stirring, and subsequently evaporating the mixture of two or more solvents at room temperature or elevated temperature T1, of 30° C. to 95° C., until crystallization occurs,
- (b) recovering precipitated 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate by filtration, optionally subsequent washing with a solvent or a solvent mixture, and optionally subsequent drying, optionally at elevated temperature T2, of 30° C. to 95° C.

26. A process for preparing crystalline modification NF5 according to claim 16, comprising
- (a) dissolving 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate anhydrate crystalline modification A1 into a binary solvent mixture, and evaporating the solvent mixture at elevated temperature, of 40-80° C., under vacuum until a precipitate is obtained,
- (b) optionally further spreading the precipitate obtained from (a) as a powder onto a bordered surface of a container, and subsequently incubating it in a sealed desiccator over water or an aqueous salt solution with defined relative humidity (RH), of 80%-100% RH, for one or more days or weeks.

27. A process for preparing crystalline modification NF5 according to claim 16, comprising
- (a) spreading 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate crystalline form NF3 as a powder onto a bordered surface of a container, and subsequently incubating in a sealed desiccator over water or an aqueous salt solution with defined relative humidity (RH), of 80-100% RH, for one or more days or weeks.

28. The solvate of claim 1 wherein the solvate is 6-(1-methyl-1H-pyrazol-4-yl)-2-{3-[5-(2-morpholin-4-yl-ethoxy)-pyrimidin-2-yl]-benzyl}-2H-pyridazin-3-one dihydrogenphosphate hydrate.

29. The process of claim 20 wherein at least one of the following conditions are met: the solvent or a solvent mixture is 2-propanole or chloroform, or wherein the elevated temperature T is 70° C.

30. The process of claim 21 wherein at least one of the following conditions are met: the solvent or a solvent mixture of (a) is water, the solvent or a solvent mixture of (b) or (d) is acetone, the elevated temperature T1 is 50° C., the temperature of the solution after cooling down is 20° C., the temperature of the resulting dispersion of (b) is cooled to 10° C., the temperature of the solution after cooling down the resulting dispersion of (c) is 5° C., the drying of the precipitated compound of (d) is done in vacuo, the solvent or a solvent mixture in which the crystals of (d) are boiled in is ethanol, the elevated temperature T2 is 70° C., or wherein the one or more minutes that the crystals of (d) are boiled is 30 minutes.

31. The process of claim 22 wherein at least one of the following conditions are met: the elevated temperature T1 is 55° C., the temperature of the solution after cooling down is 0° C. to 50° C., the cooling rate of resulting dispersion of (a) is 0.1-0.3 K/min, cooling the resulting dispersion of (b), temperature of the resulting dispersion of (b) is cooled to 10° C., cooling rate of the resulting dispersion of (b) is 0.1-0.3 K/min, the stirring the resulting dispersion of (c) at −20° C. to 40° C. is at 10° C., the solvent or a solvent mixture of (e) is acetone, the drying of the precipitated compound of (d) is done in vacuo, or wherein the elevated temperature T2 of 30° C. to 95° C. is 70° C.

32. The process of claim 23 wherein the container is a Petri dish.

33. The process of claim 24 wherein at least one of the following conditions are met: the mixture of two or more solvents is a binary mixture, the elevated temperature T1 of 30° C. to 95° C. is 50° C., the drying of the precipitated compound is done in vacuo, or wherein the elevated temperature T2, of 30° C. to 95° C. is 70° C.

34. The process of claim 25 wherein at least one of the following conditions are met: wherein the mixture of two or more solvents is a binary mixture, the solvents of the mixture of two or more solvents are selected from the group consisting of water, methanol, ethanol, 2-propanol, acetone, TFH, acetonitrile and 1,4-dioxane; elevated temperature T1, of 30° C. to 95° C. is 50° C., the drying of the precipitated compound is done in vacuo, or wherein the elevated temperature T2, of 30° C. to 95° C. is 70° C.

35. The process of claim 26 wherein at least one of the following conditions are met: the binary solvent mixture is water and methanol, the binary solvent mixture is in a ratio of 1:1, the elevated temperature, of 40° C. to 80° C. is 60° C., the container is a Petri dish, or wherein the relative humidity (RH), of 80%-100% is 90% to 100%.

36. The process of claim 27 wherein at least one of the following conditions are met: the container is a Petri dish, or wherein the relative humidity (RH), of 80%-100% is 90% to 100%.

37. A method for treating a condition, which is caused, mediated and/or propagated by the inhibition of Met-kinase, comprising administering to a subject in need thereof an effective amount of a compound according to claim 1.

38. A pharmaceutical composition comprising at least one compound according to claim 7 and a pharmaceutically acceptable carrier.

39. A pharmaceutical composition comprising at least one compound according to claim 13 and a pharmaceutically acceptable carrier.

40. A pharmaceutical composition comprising at least one compound according to claim 15 and a pharmaceutically acceptable carrier.

* * * * *